United States Patent [19]

Sarvazyan et al.

[11] Patent Number: 5,524,636
[45] Date of Patent: Jun. 11, 1996

[54] METHOD AND APPARATUS FOR ELASTICITY IMAGING

[75] Inventors: Armen P. Sarvazyan; Andrei R. Skovoroda, both of Pushchino, U.S.S.R.

[73] Assignee: Artann Corporation dba Artann Laboratories, East Brunswick, N.J.

[21] Appl. No.: 994,109

[22] Filed: Dec. 21, 1992

[51] Int. Cl.⁶ ........................................... A61B 8/12
[52] U.S. Cl. .................. 128/774; 188/660.001; 73/787; 73/818
[58] Field of Search ............... 73/818, 788, 789, 73/790, 794, 795, 796, 798; 364/413.13, 508, 556; 128/774, 660.01, 660.07, 661.07

[56] References Cited

U.S. PATENT DOCUMENTS

| | | | |
|---|---|---|---|
| 4,004,457 | 1/1977 | Eide et al. | 73/94 |
| 4,102,180 | 7/1978 | Deverakonda et al. | 73/794 |
| 4,140,008 | 2/1979 | Golembeck et al. | 73/78 |
| 4,144,877 | 3/1979 | Frei et al. | 128/2 S |
| 4,250,894 | 2/1981 | Frei et al. | 128/774 |
| 4,580,574 | 4/1986 | Gavish | 128/774 |
| 4,802,487 | 2/1989 | Martin et al. | 128/662.06 |
| 4,860,761 | 8/1989 | Yamasawa et al. | 128/686 |
| 4,865,041 | 9/1989 | Hassler et al. | 128/660.03 |
| 4,869,261 | 9/1989 | Penáz | 128/667 |
| 4,947,851 | 8/1990 | Sarvazyan et al. | 128/660.02 |
| 4,976,272 | 12/1990 | Bazin et al. | 128/774 |
| 5,024,234 | 6/1991 | Leary et al. | 128/663.01 |
| 5,031,626 | 7/1991 | Hassler et al. | 128/660.03 |
| 5,080,101 | 1/1992 | Dory | 128/660.03 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 128/660.02 |
| 5,143,070 | 9/1992 | Ophir et al. | 128/660.01 |
| 5,178,147 | 1/1993 | Ophir et al. | 128/660.01 |
| 5,265,612 | 11/1993 | Sarvazyan et al. | 128/660.01 |
| 5,278,776 | 1/1994 | Fisher et al. | 128/774 |
| 5,293,870 | 3/1994 | Ophir et al. | 128/660.01 |

FOREIGN PATENT DOCUMENTS

3900561  7/1990  Germany ..................... 128/774

OTHER PUBLICATIONS

R. M. Lerner et al., *Sono-Elasticity: Medical Elasticity Images Derived From Ultrasound Signals in Mechanically Vibrated Targets,* Acoustical Imaging, vol. 16, 317 (1988).

L. S. Wilson et al., *Ultrasonic Measurement of Small Displacements and Deformations of Tissue,* Ultrasonic Imaging 4, 71–82 (1982).

Kumasaka, Glen, *Diagnostic Considerations in Transrectal Ultrasonic Imaging of the Prostate Gland,* The Use of Transrectal Ultrasound in the Diagnosis and Management of Prostate Cancer, pp. 57–71, 1987.

Watanabe, Hiroki, *Historical Perspectives on the Use of Transrectal Sonography of the Prostate,* The Use of Transrectal Ultrasound in the Diagnosis and Management of Prostate Cancer, pp. 5–13, 1987.

Huben, Robert, *The U.S.A. Experience: Diagnosis and Follow-up of Prostate Malignancy By Transrectal Ultrasound,* The Use of Transrectal Ultrasound in the Diagnosis and Management of Prostate Cancer, pp. 153–159, 1987.

McLeary, Richard, *Future Developments in Ultrasonic Imaging of the Prostate,* The Use of Transrectal Ultrasound in the Diagnosis and Management of Prostate Cancer, pp. 209–211, 1987.

(List continued on next page.)

Primary Examiner—Angela D. Sykes
Assistant Examiner—Robert L. Nasses, Jr.
Attorney, Agent, or Firm—Westman, Champlin & Kelly

[57] ABSTRACT

An apparatus and method for imaging a portion of the body tissue comprises support for a portion of the tissue, and a force applying member that tends to deform the tissue relative to a reference position, while at the same time a pressure pattern distribution is generated indicating areas of greater pressure which are a function of the amount of deformation and localized portions of the tissue being deformed.

38 Claims, 27 Drawing Sheets

OTHER PUBLICATIONS

Yamakoshi, Yoshiki et al., *Ultrasonic Imaging of Internal Vibration of Soft Tissue under Forced Vibration*, IEEE Transactions on Ultrasonics, Ferroelectrics and Frequency Control. vol. 37, No. 2, pp. 45–53, Mar. 1990.

Ophir, J. et al., *A Transaxial Compression Technique (Tact) for Localized Pulse-Echo Estimation of Sound Speed in Biological Tissues*, Ultrasonic Imaging 12, 35–46 (1990).

Ophir, J. et al., *Elastography: A Quantitative Method for Imaging the Elasticity of Biological Tissues*, Ultrasonic Imaging 13, 111–134 (1991).

Tanouchi, J. et al., *Visualization of Local Elasticity of Artery to Evaluate Arteriosclerosis with Digital Subtraction Echography (DSE) Preliminary Study*, pp. 190–191.

Ishihara, K., *High–Speed Digital Subtraction Echography: Principle and Preliminary Application to Arteriosclerosis, Arrhythmia and Blood Flow Visualization*, 1990 Ultrasonics Symposium, pp. 1473–1476.

Gentle, C. R., *Mammobarography: A Possible Method of Mass Breast Screening*, Journal Biomed. Eng. 1988, vol. 10, Apr., p. 124.

Krouskop, T. A. et al., *A Pulsed Doppler Ultrasonic System for Making Noninvasive Measurements of the Mechanical Properties of Soft Tissue*, Journal of Rehabilitation Research and Development vol. 24, No. 2, 1987, pp. 1–8.

Martin, June, *Transrectal Ultrasound: A New Screening Tool for Prostate Cancer*, American Journal of Nursing, Feb. 1991, p. 69.

Chodak, Gerald, *Transrectal Ultrasonography: Is it Ready for Routine Use?*, Jama, May 13, 1988, vol. 259, No. 18, pp. 2744–2745.

*Diagnostic and Therpeutic Technology Assessment (DATTA)*, Jama, May 13, 1988, vol. 259, No. 16, pp. 2757–2758.

Pipe, James et al., *Method for Measuring Three-Dimensional Motion with Tagged MR Imaging*, Radiology 1991; 181:591–595.

Lerner, Robert et al., *"Sonoelasticity" Images Derived From Ultrasound Signals in Mechanically Vibrated Tissues*, Ultrasound in Med. & Biol. vol. 16, No. 3, 1990, pp. 231–239.

Parker, K. J. et al., *Tissue Response to Mechanical Vibrations for "Sonoelasticity Imaging"*, Ultrasound in Med. & Biol., vol. 16, No. 3, 1990, pp. 241–246.

Yamashita et al., *Tissue Characterization from Ultrasonic Imaging of Movement and Deformation*, 1990 Ultrasonics Symposium, pp. 1371–1375.

Publication: *Acoustic Images*, Issue 4, Summer 1991.

Publication: *Acoustic Images*, Issue 5, Winter 1991.

Tristam et al., *Application of Fourier Analysis to Clinical Study of Patterns of Tissue Movement*, Ultrasound in Med. & Biol. vol. 14, No. 8, pp. 695–707, 1988.

Tristam et al., *Ultrasonic Study of In Vivo Kinetic Characteristics of Human Tissues*, Ultrasound in Med. & Biol. vol. 12, No. 12, pp. 927–937, 1986.

Dickinson et al., *Measurement of Soft Tissue Motion Using Correlation Between A-Scans*, Ultrasound in Med. & Biol. vol. 8, p. 263, 1982.

*Diagnositc and Therpeutic Technology Assessment (DATTA)*, Jama, Mar. 16, 1990, vol. 263, No. 11, pp. 1563–1568.

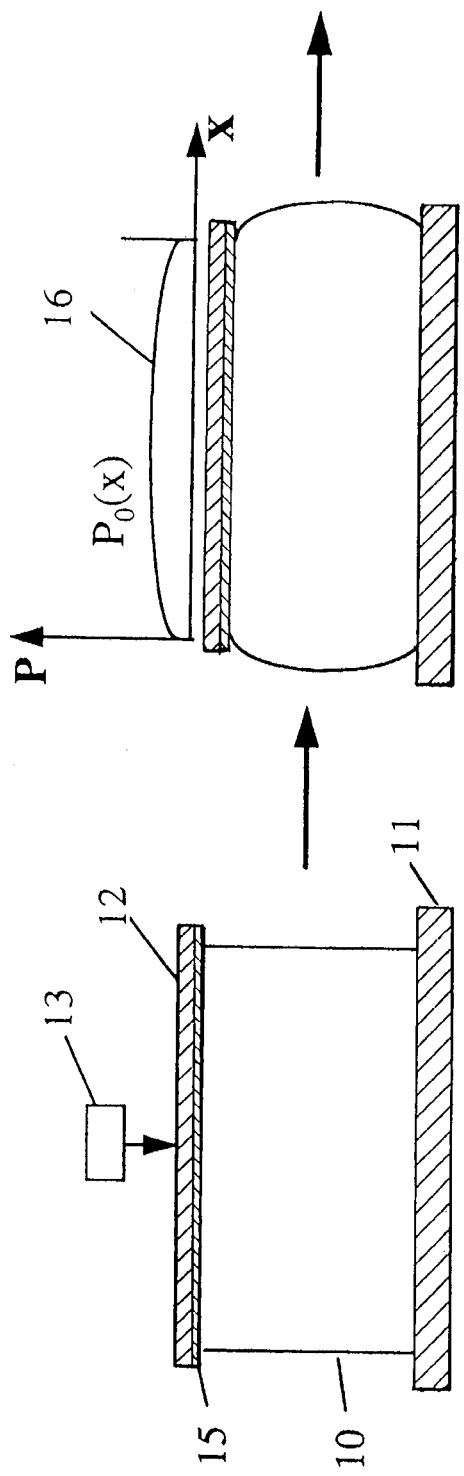
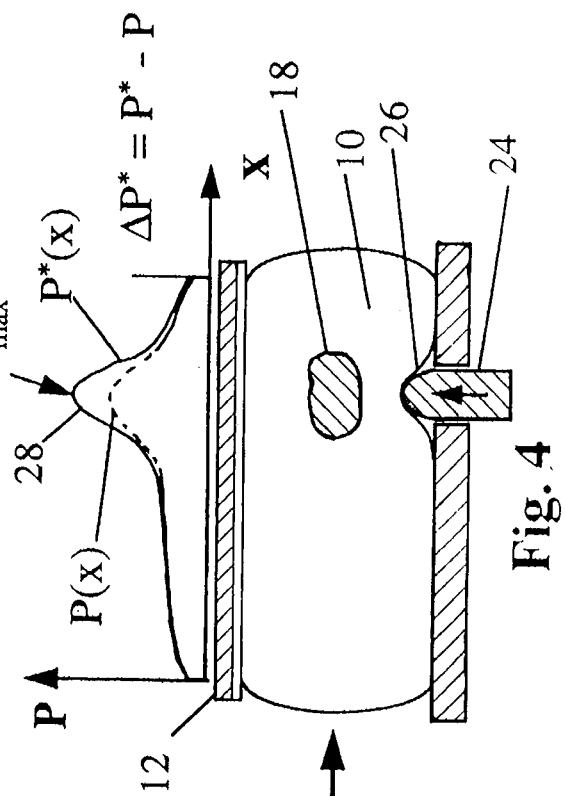
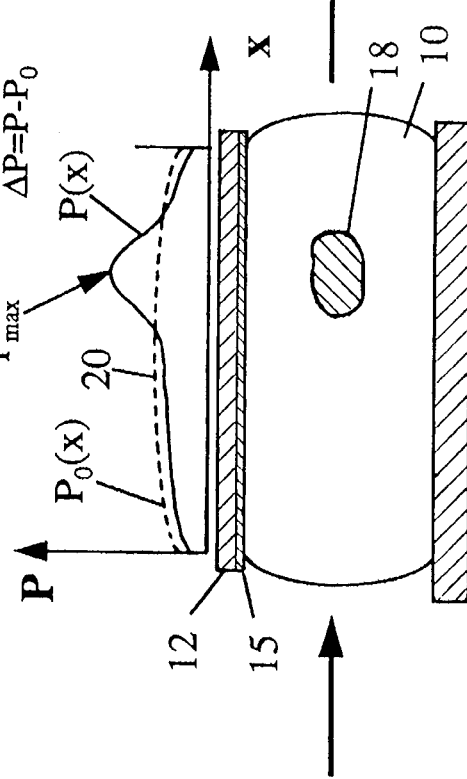
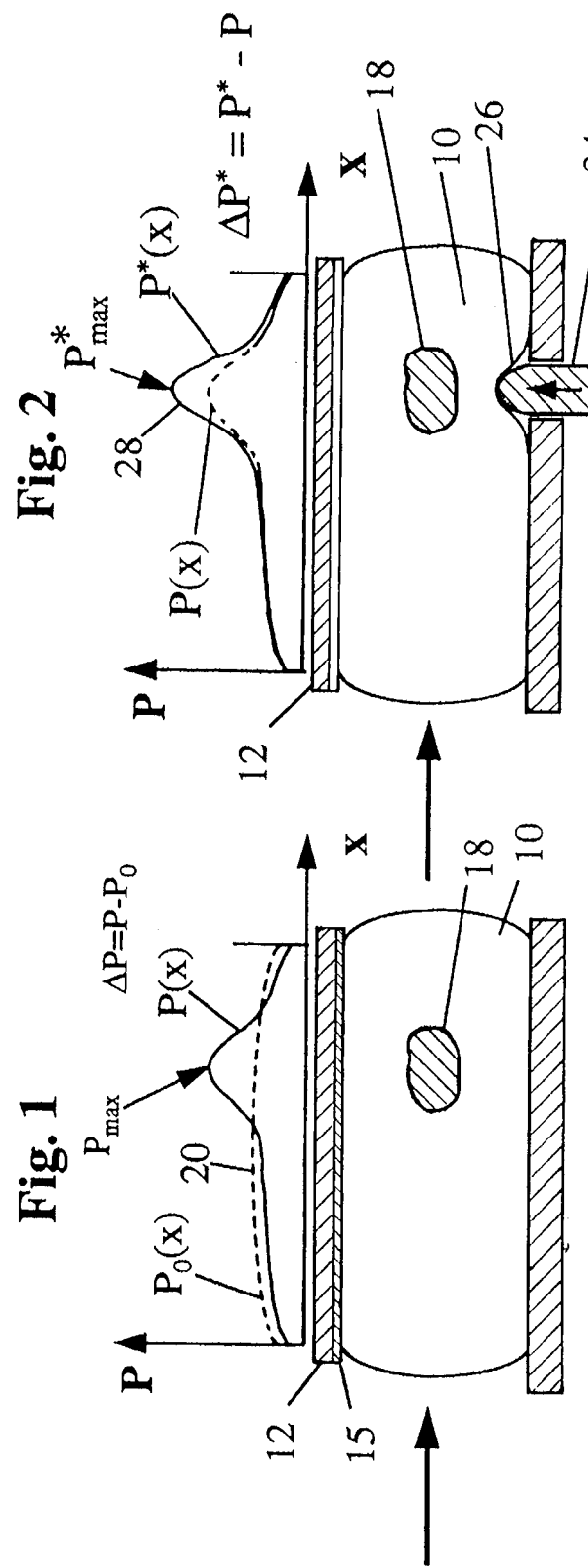
Fig. 1
Fig. 2
Fig. 3
Fig. 4

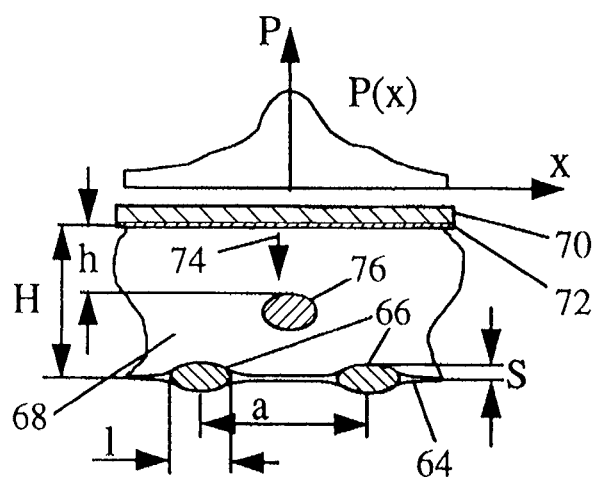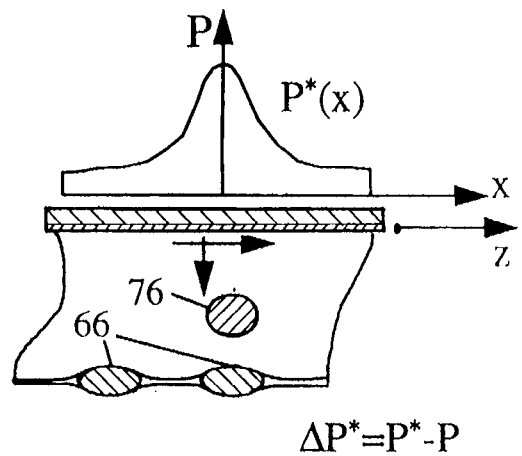
Fig. 13A  Fig. 13B
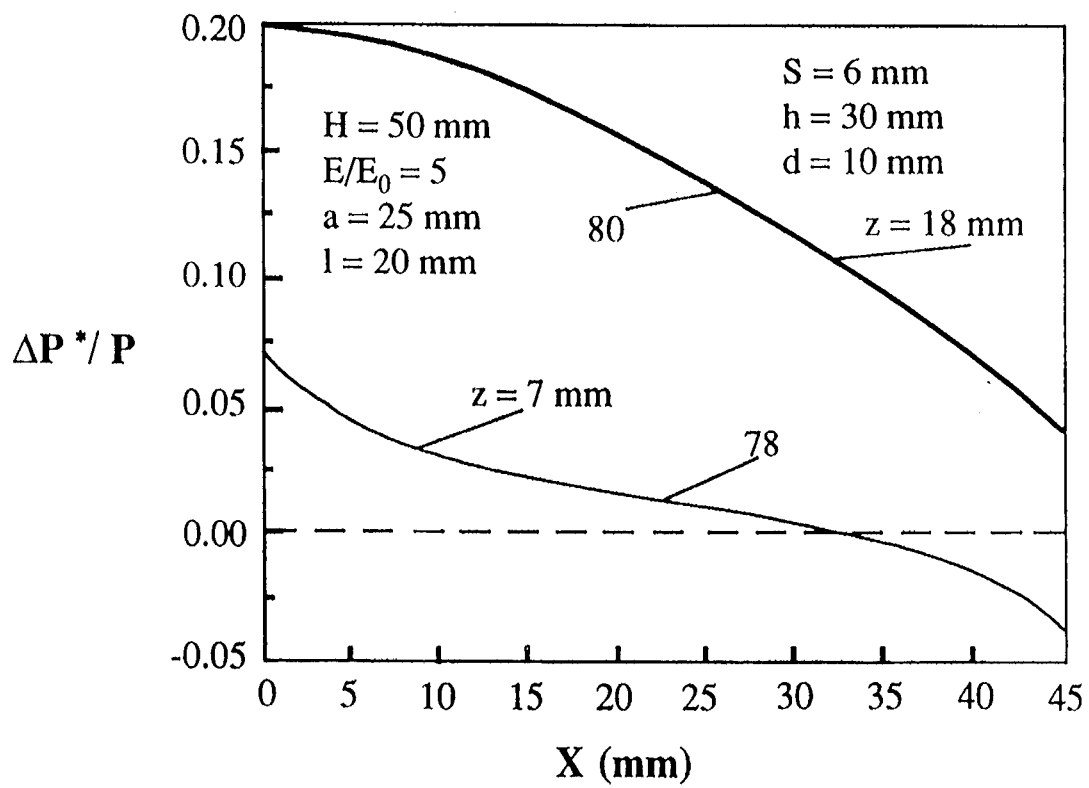
Fig. 13C

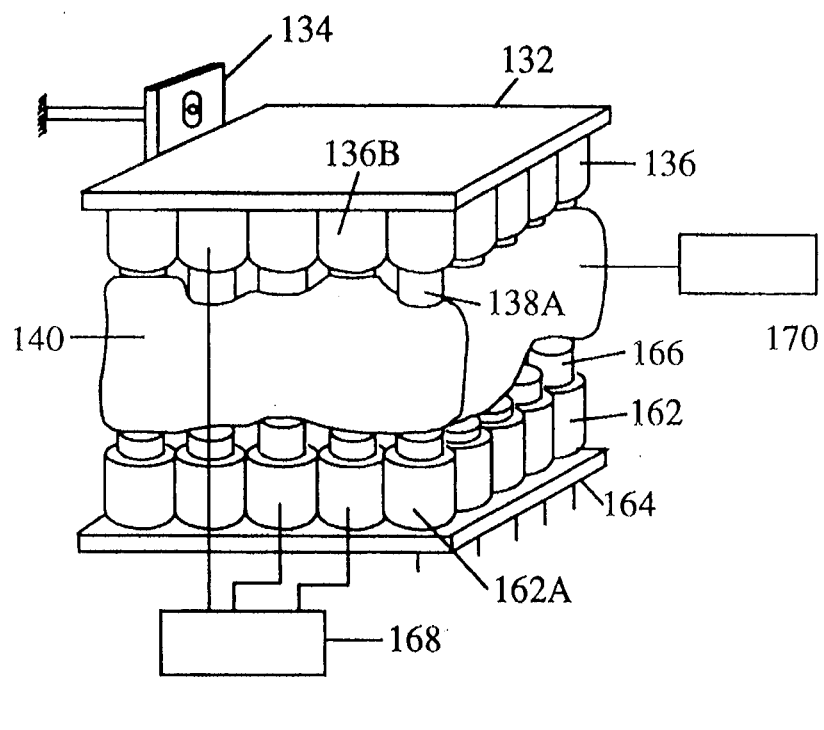
Fig. 18A
Fig. 18
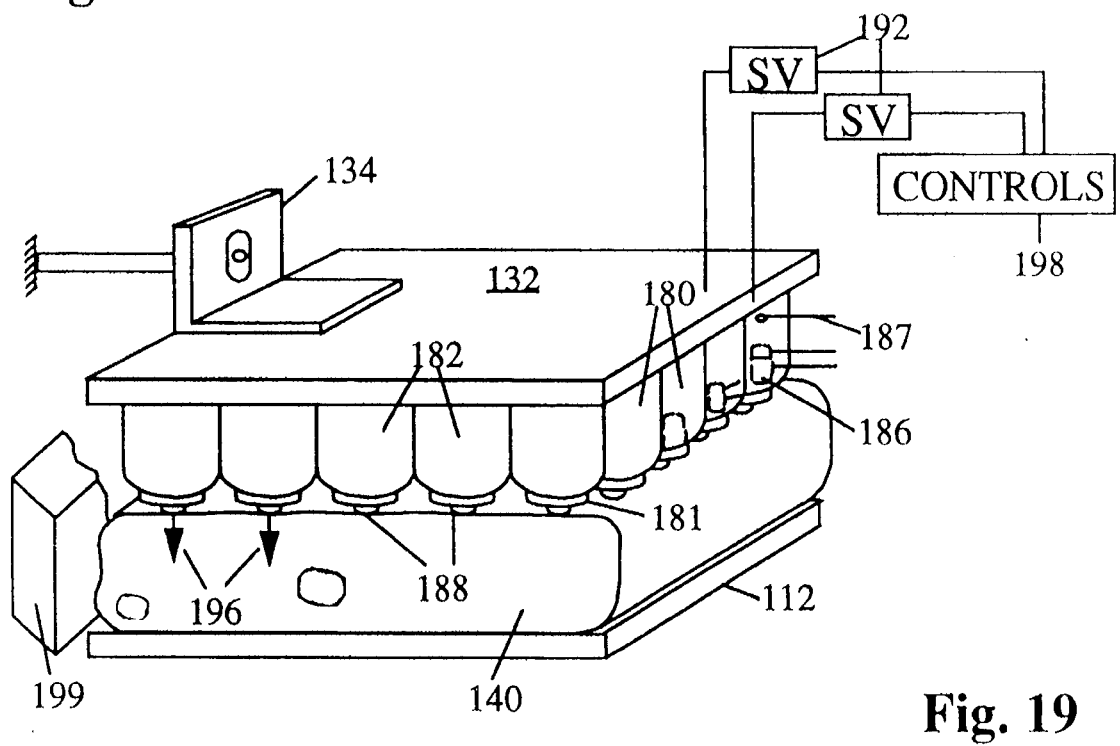
Fig. 19

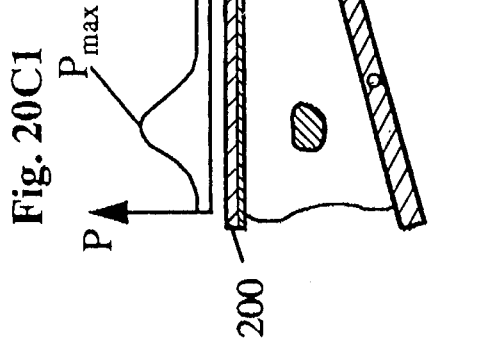
Fig. 20A1  Fig. 20A
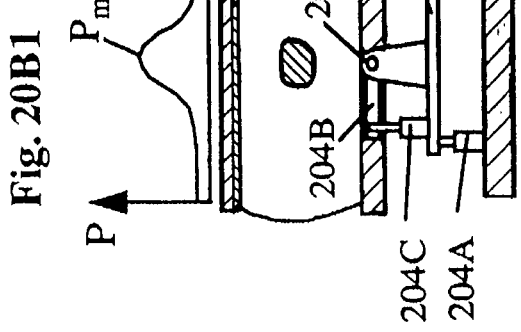
Fig. 20B1  Fig. 20B
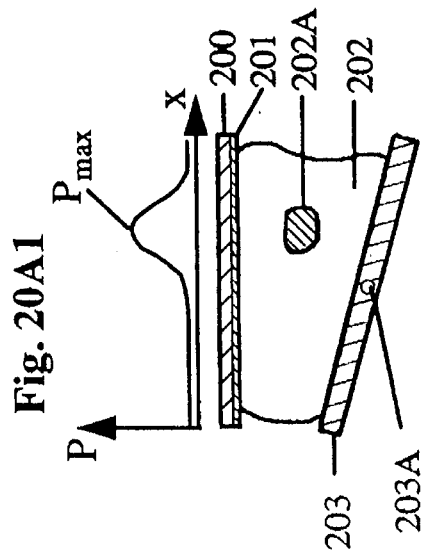
Fig. 20C1  Fig. 20C
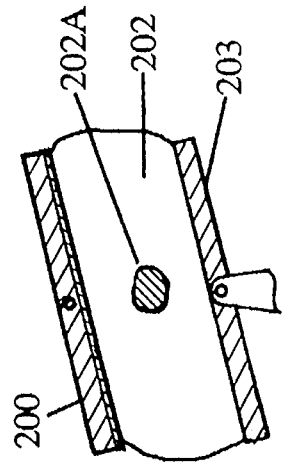
Fig. 21A
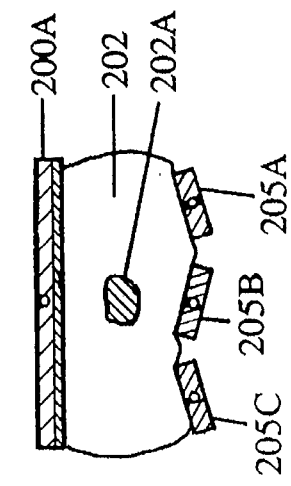
Fig. 21B
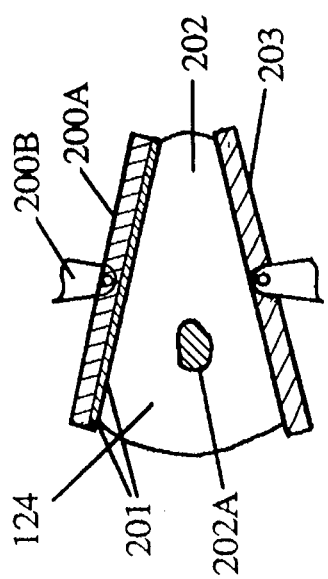
Fig. 21C $E_A > E_0 \Rightarrow \varepsilon_A < \varepsilon_0$
$E_B < E_0 \Rightarrow \varepsilon_B > \varepsilon_0$

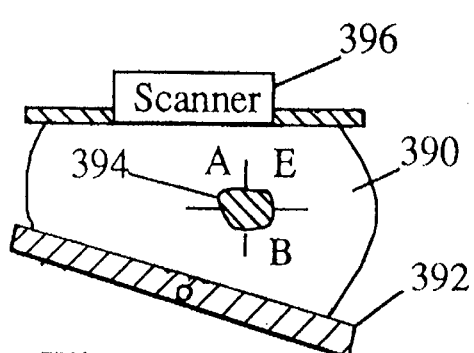
Fig. 38A
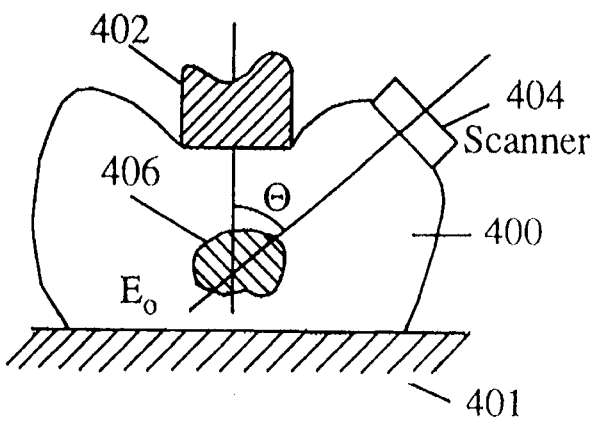
Fig. 38B
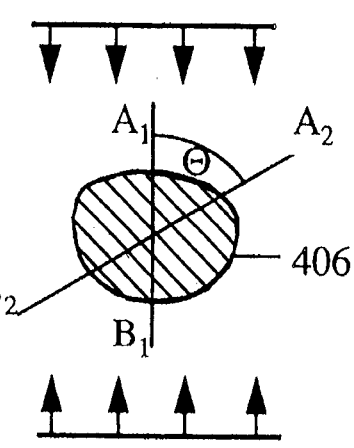
Fig. 38C
Fig. 38D
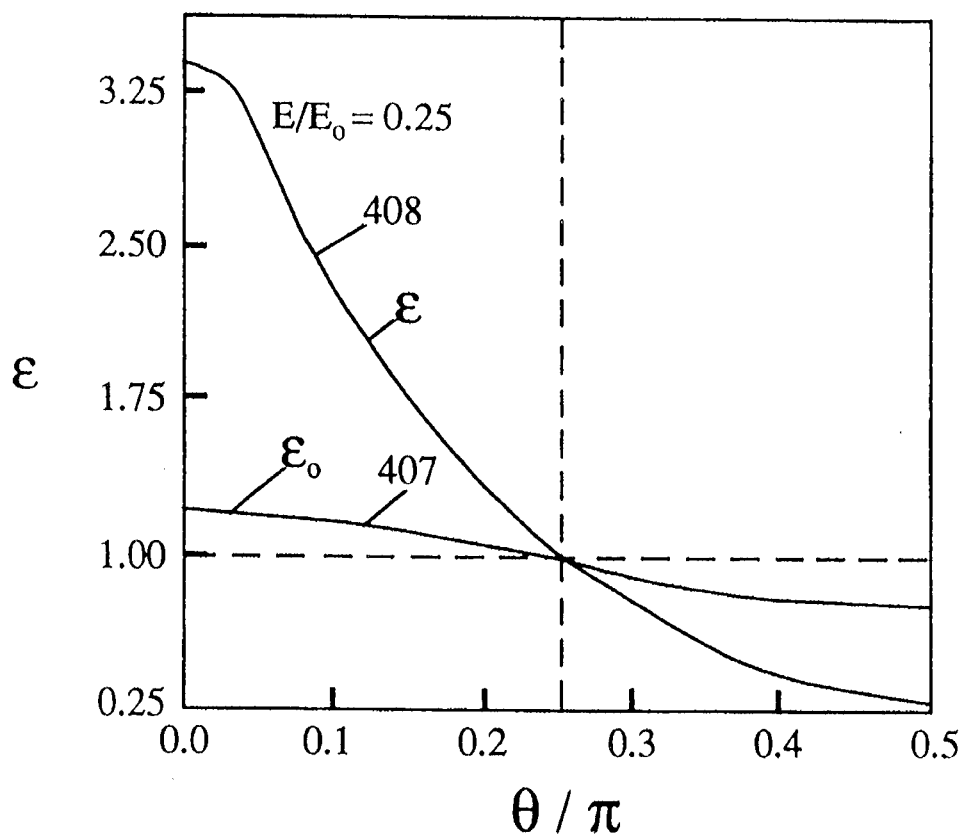

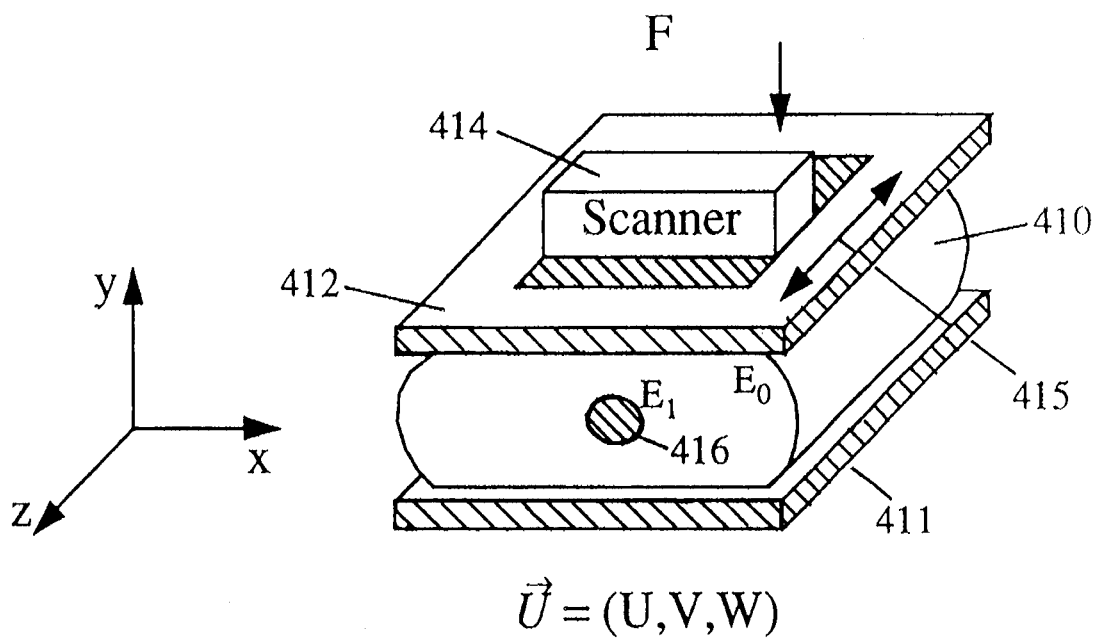
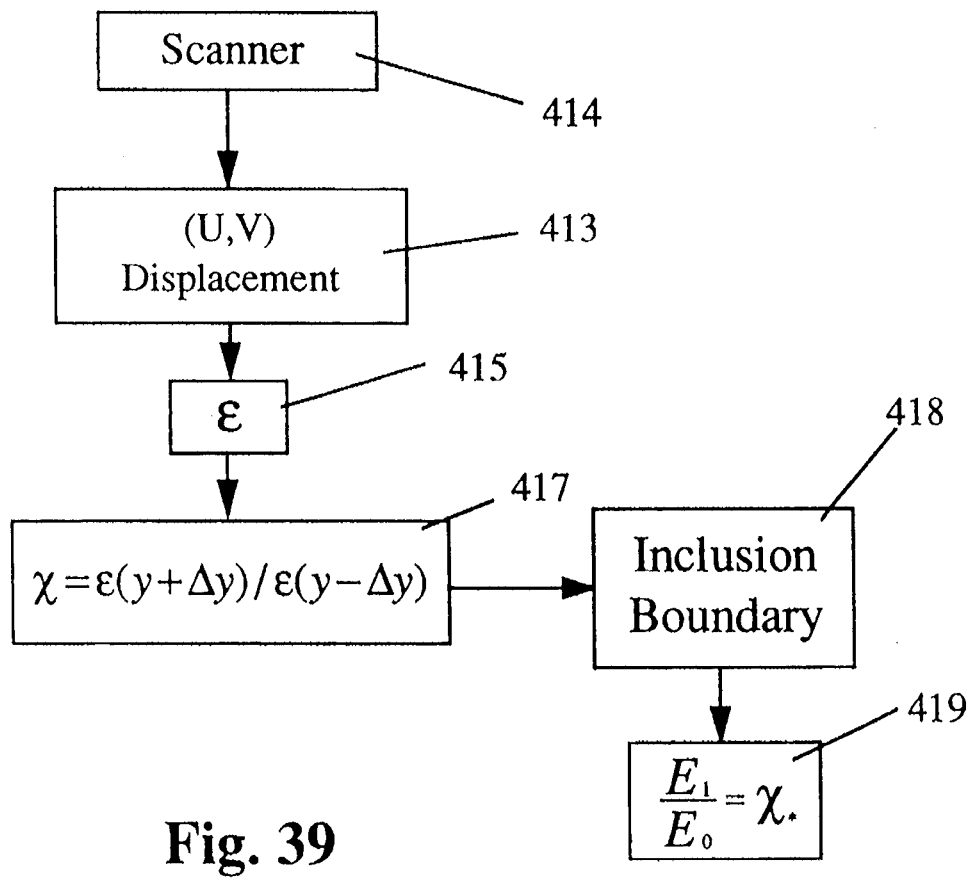
Fig. 39

$$\frac{E_1}{E_0} = \chi\big|_Q$$

$$(n_x, n_y, n_z)\big|_Q = (\pm\tfrac{1}{\sqrt{2}}, \pm\tfrac{1}{\sqrt{2}}, 0)$$

METHOD AND APPARATUS FOR ELASTICITY IMAGING

CROSS REFERENCE TO RELATED APPLICATION

References is hereby made to co-pending application Ser. No. 07/823,155, filed Jan. 21, 1992 and entitled METHOD AND DEVICE FOR MECHANICAL TOMOGRAPHY OF TISSUE.

BACKGROUND OF THE INVENTION

The present invention relates to an apparatus for determining tissue elasticity in various parts of the body and using such information as a diagnostic tool in the detection of abnormalities of tissue, such as those caused by cancer or other lesions. The "hardness" of tumors can be quantified in terms of the surrounding tissue elastic properties.

Diagnosing early formation of tumors or lesions, particularly those caused by cancer, has been a problem that has been attempted to be solved using various techniques, such as ultrasonic imaging, nuclear magnetic resonance imaging, x-rays, and the like. Each of these techniques have limitations, including the application of radiation to the body, which may be harmful to the body being tested.

One approach attempts to determine the relative stiffness or elasticity of tissue by applying ultrasound imaging techniques while vibrating the tissue at low frequencies. See, e.g., R. M. Lerner et al., *Sono-Elasticity: Medical Elasticity Images Derived From Ultrasound Signals in Mechanically Vibrated Targets*, Acoustical Imaging, Vol. 16, 317 (1988), Robert M. Lerner et al., *"Sonoelasticity" Images Derived from Ultrasound Signals in Mechanically Vibrated Tissues*, Ultrasound in Med. & Biol. Vol. 16, No. 3, 231 (1990) and K. J. Parker et al., *Tissue Response to Mechanical Vibrations for "Sonoelasticity Imaging"*, Ultrasound in Med. & Biol. Vol 16, No. 3, 241 (1990).

A variety of other methods have been proposed for measuring the mechanical characteristics, e.g., elasticity, inside soft tissues. One method includes using an ultrasonic wave as a probing wave to observe the mechanical responses of tissues due to cardiac pulsation. The mechanical responses are observed using the ultrasonic wave and then information regarding the mechanical characteristics are estimated on patterns of small movements in the tissue in response to cardiac pulsation. See R. J. Dickinson and C. R. Hill, *Measurement of Soft Tissue Motion Using Correlation Between A-Scans*, Ultrasound in Med. and Biol. Vol. 8, 263 (1982) and M. Tristam et al., *Ultrasonic Study of In Vivo Kinetic Characteristics of Human Tissues*, Ultrasound in Med. and Biol. Vol. 12, 927 (1986). The technique uses Fourier analysis to objectively differentiate different tissue types in pathologies based on numerical features of the time-course of a correlation coefficient between pairs of A-Scans recorded with a particular time separation. Tissue oscillations resulting from ventricular contraction and pressure pulses in the descending aorta are measured to derive patterns of movement. Fourier series transformation is used to analyze the data to quantitate the kinetic behavior of the tissue in vivo. M. Tristam et al., *Application of Fourier Analysis to Clinical Study of Patterns of Tissue Movement*, Ultrasound in Med. and Biol. Vol. 14, 695 (1988).

Another method for estimating the mechanical properties of desired points inside the tissue has been proposed in which low-frequency vibration is applied to the surface and the wave velocity inside the tissue is measured by using the simultaneously transmitted ultrasonic waves. The difference of velocity near the measuring point allows one to derive the elastic property of the tissue. See T. A. Krouskop et al., *A Pulsed Doppler Ultrasonic System for Making Non-Invasive Measurement of Mechanical Properties of Soft Tissue*, 24 J. Rehab. Res. Dev. Vol. 24, 1 (1987).

Another method of evaluating the elasticity of tissue includes applying low-frequency vibration (e.g., several hundred Hz) to the surface while measuring both the amplitude and phase of internal vibration based on Doppler frequency modulation of simultaneously transmitted probing ultrasonic waves. The amplitude and phase maps are used to observe information that relates to the viscoelastic properties of the tissues. Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, Page 45 (1990).

In another method, the wave forms of liver dynamics caused by aortic pulsation and vessel diameter variations are observed by a signal processing technique for analyzing radio frequency M-mode signal patterns of movement (in the liver) in response to the arterial pulsation. The wave forms are used to determine tissue characteristics (displacement, velocity, and strain) as a function of time in small deformations in tissue due to the arterial pulsation. Wilson and Robinson, *Ultrasonic Measurement of Small Displacements and Deformations of Tissue*, Ultrasonic Imaging Vol. 4 (1982) 71–82.

Another method recently proposed for measuring and imaging tissue elasticity is described in Ophir et al., U.S. Pat. No. 5,107,837. This method includes emitting ultrasonic waves along a path into the tissue and detecting an echo sequence resulting from the ultrasonic wave pulse. The tissue is then compressed (or alternatively uncompressed from a compressed state) along the path and during such compressing, a second pulse of ultrasonic waves are sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions. This technique is further described in Ophir et al., *Elastography: A Quantitative Method for Imaging the Elasticity of Biological Tissues*, Ultrasonic Imaging 13, 111 (1991). See also J. Ophir et al., *A Transaxial Compression Technique (TACT) For Localized Pulse-Echo Estimation of Sound Speed in Biological Tissues*, Ultrasonic Imaging 12, 35 (1990).

It is desirable to have the capability to investigate tissue elasticity changes, which may indicate precursors of tumors or actual tumors without subjecting the patient to radiation. There is also a need for equipment that is easy to use and which requires relatively low capital investment. It also would be desirable to use currently available non-invasive imaging modalities, such as ultrasound, magnetic resonance imaging (MRI), computer aided tomograph (CAT) scanning, and the like.

SUMMARY OF THE INVENTION

The present invention relates to a system of devices which will deform tissue to permit a method of analyzing the elasticity of such deformed tissue using noninvasive techniques. The apparatus includes devices for applying a pressure to living tissue which causes deformation and permits determining the presence and location of tissue that has different elastic characteristics from surrounding tissue. The method of identifying a region of the tissue having a different elasticity than the surrounding tissue includes causing a mechanical deformation of a tissue portion and determining patterns of at least one of the properties of stress and strain in the deformed tissue portions to identify the presence and location of the differing elasticity regions of tissue.

A pattern of stress or strain in a limited area of tissue, together with the geometrical relationship of this limited area to a support member, a deformation member and neighboring anatomical features of that tissue, provides a way of postulating boundary conditions and calculating stress and strain patterns in the region of interest. The obtained relationship contains information about elastic modulus in the region of interest.

The apparatus utilizes various deformation techniques, such as direct pressure heads, moving "fingers" that simulate palpation of tissue, rollers that will roll across a surface of the tissue to be analyzed, and pads, and also may include internal sources of stress or strain such as changes in pressures caused by the variations in blood pressure as well as in muscle contraction.

Various imaging modalities, such as ultrasound, CAT scan, magnetic resonance imaging, and similar techniques that are presently available (or which may be developed for examining internal structures of tissue without invasion of the tissue) can be used in conjunction with the deformation techniques applied to the tissue for analyzing elasticity of the tissue.

As will be shown, various programs can be used for deformation sequences so that automatic changing or cycling of small areas of compression will occur, at the same time that the imaging modalities are operating. In this way, computerized imaging can be used for evaluating stress and strain patterns in the imaged tissue, calculating relative elasticities of the regions of interest and then projecting three-dimensional representation of an area of tissue with the different elastic properties indicated on a screen.

Intracavity elasticity can be analyzed with internal probes inserted into bodily cavities. The deformation of bodily conduits can be examined by using a force sensor array positioned annularly around a central fluid-containing system. By using a rubber-type jacket under the force sensors, pressure variations can be exerted on the internal walls of bodily conduits while the stress pattern can be determined and changes in the elasticity characteristics of the tissue around the conduit can be calculated. Thus, this unit eases the analysis of tumors being formed in the vicinity of the colon, particularly prostate tumors. In addition, the unit can be used as an intrauterine device to determine formations of lesions or the effect of scarring.

While various devices are illustrated for causing deformation of tissue from the exterior, other such devices can be used. The orientation of the devices as well as the pressure exerted, the size of the area being loaded, and other factors can be varied to suit existing conditions based on continuing examinations.

BRIEF DESCRIPTION OF THE DRAWINGS

FIG. 1 is a schematic representation of a model of soft "tissue" illustrating a device for loading incorporating pressure sensors used in the present invention;

FIG. 2 is the device of FIG. 1 after loading the tissue, and illustrating a typical pressure curve across a surface of the tissue;

FIG. 3 is similar to the tissue compression in FIG. 2, with the effect of a presence of a tumor in the tissue illustrated;

FIG. 4 is an illustration of the structure shown in FIG. 3, with a piston deforming tissue from a side opposite from the pressure plate;

FIG. 13A is a graphical representation of tissue positioned over underlying objects such as ribs, and being loaded in accordance with the present invention;

FIG. 13B is an illustration similar to that shown in FIG. 13A with the outer surface of the tissue shifted relative to the supporting ribs;

FIG. 13C is a graphical representation of the changes in pressure profile after a shift of the outer surface of the tissue has been made as shown in FIG. 13B;

FIG. 14A is a graphical representation of the moved stress curve in a X-axis direction with a hardened area or tumor being moved by the roller of FIG. 14;

FIG. 18 is a modification of the device of FIG. 17 showing actuators on both the top and bottom, wherein the actuators have force sensors directly thereon;

FIG. 18A is an illustration of pressure sensors on the end of an actuator rod;

FIG. 19 is a representation of a typical arrangement that uses stepped or smaller diameter end pistons;

FIGS. 20A, 20B and 20C are representations of the device utilizing a pivoting support plate relative to a fixed pressure sensor array;

FIGS. 20A-1, 20B-1 and 20C-1 are graphical representations of a moving of the typical stress-related curve relationship of the tissue along a horizontal line illustrating the effect of a moved hardened lump on an image of the tissue cross section of FIGS. 20A, 20B and 20C respectively;

FIGS. 21A, 21B and 21C are variations of the structures shown in FIG. 20 with pivoting or movable plates on both the top and bottom of the section of tissue being analyzed with FIG. 21B being an illustration wherein at least one of the plates can be made up of several sections which are provided for deformation of the tissue in a different configuration;

FIG. 38A is a schematic representation of a scanner located on the tissue with a compression plate supporting the tissue in an off-axis manner;

FIG. 38B is a schematic representation and cross-section of a tissue block with tumor therein under a compressive load with a scanner on a side of the tissue at an angle relative to the compression device;

FIG. 38C is a schematic representation of tissue under the loading shown in FIG. 38B with the compressed tissue shown in phantom with angular strain parameters illustrated;

FIG. 38D is a graphical representation of the relative deformation of tumorous tissue relative to surrounding tissue observed as a function of the angle θ of a scanning axis relative to a compressive axis as shown in FIG. 38C;

FIG. 39 is a schematic representation in perspective of a tissue block under compression between force applying plates similar to those in FIG. 36 and with a scanner transversely movable across an upper plate, and including a box diagram flow chart for determining the ratio of modulus of elasticities based on calculating inclusion boundaries;

DETAILED DESCRIPTION OF THE PREFERRED EMBODIMENTS

Figure 5:
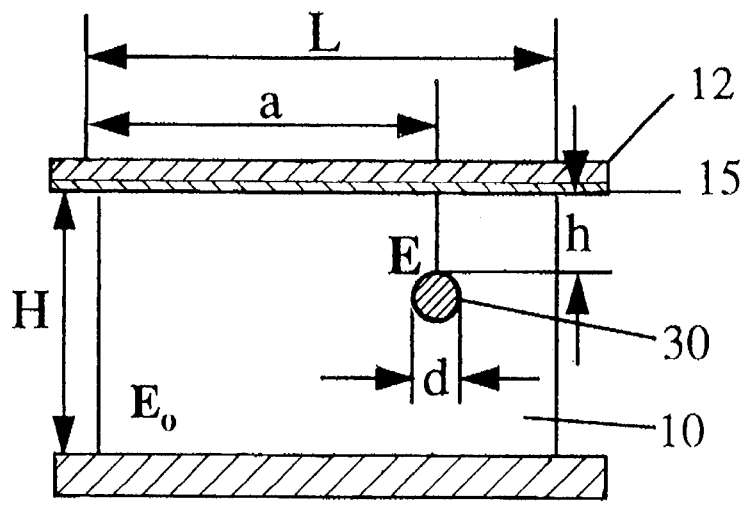
FIG. 5 is a schematic illustration of loading parameters for a model tissue being examined and a tumor in such tissue.

Pressure patterns together with initial boundary conditions can enable one to reconstruct internal structures in underlying tissue and evaluating relative hardness and softness of tissue in localized areas. The present invention expands on teachings of how tissue abnormalities can be detected and, as will be shown, the present invention recognizes that the displacements of localized areas inside of tissue and the stress pattern in the tissue are inter-related and that this relationship forms the basis for a method of detecting and quantifying tissue abnormalities based on elasticity difference evaluation. The method of analysis of the present invention is widely applicable and may be used as with pressure sensing arrays, in combination or separately, with virtually any type of imaging (e.g., ultrasound (US), magnetic resonance imaging (MRI), computer aided tomography (CAT)), or other types of information input.

When calculating the mechanical properties of tissues, calculations are based on a model of the tissue as being linearly elastic and incompressible media. Such an approach is a first approximation which is sufficient to solve all questions arising in mechanical elasticity imaging. In a case where an exact solution is to be obtained without considering the object as linearly elastic, one can also use non-linear solutions which are more elaborate but will add improvement in the solution. See, Green A. E., Adkins J. E., *Large Elastic Deformations,* Clarendon Press, Oxford, 1970. However, this does not alter qualitatively the answers obtained under the linear elastic model. In the case of local inclusions, the result of the imprint of this inclusion into the stress-strain state of the surrounding body is expressed very strongly in a three dimensional manner. Therefore characterizing an inclusion such as a lump in a breast, using a one dimensional model (see Ophir et al., U.S. Pat. No. 5,107,837) to characterize the strain in the inclusion and tissue is extremely deficient.

Accordingly, the graphical representations discussed in this detailed description are based on calculations from the general equations presented below. The following equations are general equations for three dimensional linear theory of elasticity for incompressible media like tissues or another water based system that is a system having a Poisson's ratio of 0.5, as shown below.

These are equations of dynamic equilibrium:

$$\frac{\partial \sigma_{xx}}{\partial x} + \frac{\partial \sigma_{xy}}{\partial y} + \frac{\partial \sigma_{xz}}{\partial z} = \rho \frac{\partial^2 U}{\partial t^2} \quad (1)$$

$$\frac{\partial \sigma_{xy}}{\partial x} + \frac{\partial \sigma_{yy}}{\partial y} + \frac{\partial \sigma_{yz}}{\partial z} = \rho \frac{\partial^2 V}{\partial t^2}$$

$$\frac{\partial \sigma_{xz}}{\partial x} + \frac{\partial \sigma_{zz}}{\partial y} + \frac{\partial \sigma_{zz}}{\partial z} = \rho \frac{\partial^2 W}{\partial t^2}$$

Where:
U, V, W are components of displacement (strain) (three axes)
ρ is density of media
$\sigma_{ij}$ are components of stress tensor (stress).

We must next relate the pattern of stresses to a pattern of strain. This relationship for incompressible media (e.g. tissues or other water based systems) is given by the following equations.

$$\begin{cases} \sigma_{xx} = P + 2\mu E_{xx} & \sigma_{yy} = P + 2\mu E_{yy} & \sigma_{zz} = P + 2\mu E_{zz} \\ \sigma_{xy} = 2\mu E_{xy} & \sigma_{xz} = 2\mu E_{xz} & \sigma_{yz} = 2\mu E_{yz} \end{cases}$$

Where:

$$\mu = \frac{E}{2(1+\nu)}$$

$\nu = 0.5$ – Poisson's ratio, where $E$ = Young's Modulus $$E_{xx} = \frac{\partial U}{\partial x}$$

$$E_{yy} = \frac{\partial V}{\partial y}$$

$$E_{zz} = \frac{\partial W}{\partial z}$$

$$E_{xy} = \frac{1}{2}\left(\frac{\partial U}{\partial y} + \frac{\partial V}{\partial x}\right)$$

$$E_{xz} = \frac{1}{2}\left(\frac{\partial U}{\partial x} + \frac{\partial W}{\partial z}\right)$$

$$E_{yz} = \frac{1}{2}\left(\frac{\partial V}{\partial z} + \frac{\partial W}{\partial y}\right)$$

By combining equations (1) and (2), we can obtain three equations containing only three unknowns, U, V, W, which are components of displacement plus the unknown pressure P.

In addition we have the equation of incompressibility which shows that divergence of vector of displacement equals zero.

$$\frac{\partial U}{\partial x} + \frac{\partial V}{\partial y} + \frac{\partial W}{\partial z} = E_{xx} + E_{yy} + E_{zz} = 0$$

This last equation represents the condition that when force is applied to the soft tissue because Poisson's ratio is 0.5, all the deformation of tissue is related to changes of the shape of the soft tissue but not the volume.

Bulk compressional modulus in tissue is many orders of magnitude higher than shear elasticity modulus as defined by Poisson's ratio of 0.5.

After taking into account boundary conditions, boundary problem for a system of equations in partial derivatives can be obtained. The technique of solving such boundary problems is well developed and can be used for the obtaining the solution required for elasticity imaging. See Samarski A. A., Nikolaev E. S., *The Methods of Solving of Equations in Finite Differences,* M., Nauka, 1978.

The characteristics of living tissue not only involve elasticity as discussed, but also viscosity. Thus, the tissue is a viscoelastic material that requires description in both viscous and elastic components. Viscosity affects the information received because with a viscoelastic tissue, there is a time delay between force application and any displacement that occurs. In a dynamic mode where force is applied in time, the development of stresses in time provides the information on viscosity.

In case of viscoelastic media, the components of stress tensor in equation (2) should have following additional terms for shear viscosity, $\mu^*$ $$2\mu^* \frac{\partial E_{ij}}{\partial t}$$

The shear modulus and Young's modulus of soft tissue are different by a factor of 3, because Poisson's ratio is 0.5. While either modulus can be used for examination of the tissue, Young's modulus is used in the description of the present invention.

In the case of harmonic disturbances, temporal dependence can be easily removed from these equations and the system of the differential equations for amplitudes will be obtained.

FIG. 1 illustrates a portion of a soft tissue 10 that is supported on a thick surface 11 and which supports a flat rigid plate 12 capable of exerting pressure thereon from a force generator 13. A series of individual pressure sensors indicated at 15 are provided on the bottom surface of the plate 12 to sense pressure in an array across the surface of the tissue block 10.

FIG. 2 represents a pressure (P) profile of homogeneous tissue when deformed. FIG. 3 illustrates a homogeneous tissue pressure profile in the dotted line and in the solid line the profile of the tissue having an inclusion 18. The difference between these two pressure profiles shown in FIG. 3 contains information on the presence, location, and relative elasticity of inclusion 18 in respect to surrounding tissue 10. The strain pattern on the surface of the tissue 10 as shown in FIG. 3 is in this case represented in the form of pressure profile P(x). This strain pattern depends on the presence of an inclusion 18, as well as on the dimension of the tissue portion, neighboring anatomical features of that tissue, such as presence of a bone, and on the geometrical relationship of the tissue portion 10, support member 11 and deformation member 12. Therefore, not the strain profile P(x) itself, but the difference between the measured profile P(x) and the profile $P_0(x)$, shown by the dotted line, theoretically calculated for a homogenous model of that tissue under the same boundary conditions using the equations and techniques for determining boundary conditions outlined above contains direct information on the inclusion.

FIG. 4 schematically illustrates how the present invention enhances the amplitude of the pressure profile and, thus, improves detection of an inclusion. In this instance, the tissue 10 is supported on a base 11, and a schematically shown piston or block 24 which also is called a "finger" as used in palpation, is provided on the base and is caused to protrude into the tissue and compress the tissue in a localized area indicated at 26 directly below the tumor 18.

The represented pressure profile schematically disposed on the top of the pressure plate 12 (which is displaced the same as that previously explained) represents the data provided by the pressure sensors 15. P(x) is represented as a dashed line and is the profile substantially as that shown in FIG. 3. P*(x), indicated by line 28, represents the pressure profile resulting from the presence of the piston 24 directly under the tumor. The piston 24 acts like a probe to cause extra compression in the desired region (e.g., tumor 18) in addition to the general compression of the tissue block 10 between plate 12 and surface 11. This results in a substantial increase in the pressure profile P*(x) which reaches a maximum at $P^*_{max}$ directly over the tumor. By comparing the respective pressure profiles P(x) and P*(x), one can recognize that a much greater amplitude of the pressure profile can be obtained from the pressure sensors (to indicate an abnormality) when a probe (e.g., piston 24) or other extra compressive force is directed in the region of a tumor. In this case, a change in the pressure profile amplitude because of the piston 24 is represented as $\Delta P^* = P^* - P$.

Therefore, one aspect or embodiment of the present invention is to provide an amplification of the pressure signals by using a probing piston on a side opposite from the pressure sensor to cause extra deformation in a region where a tumor occurs. Moreover, by using a number of pistons in an array, and altering the pressures or displacements caused by the pistons, location of a tumor can be more readily determined because of the larger amplitude pressure signal in the area of an inclusion caused by these extra compressive forces.

The following FIGS. 5–13 are schematic examples to illustrate the applicability of the theory to the methods and devices disclosed, and to show the range of variables and measured parameters available for calculating meaningful values for quantitative analysis and evaluation. The illustrations of tissue are not meant to represent any particular portion of a human body. Clinically, the illustrations of FIGS. 1–22 are closely applicable to examining tumor characteristics in breast tissue.

Figure 5A:
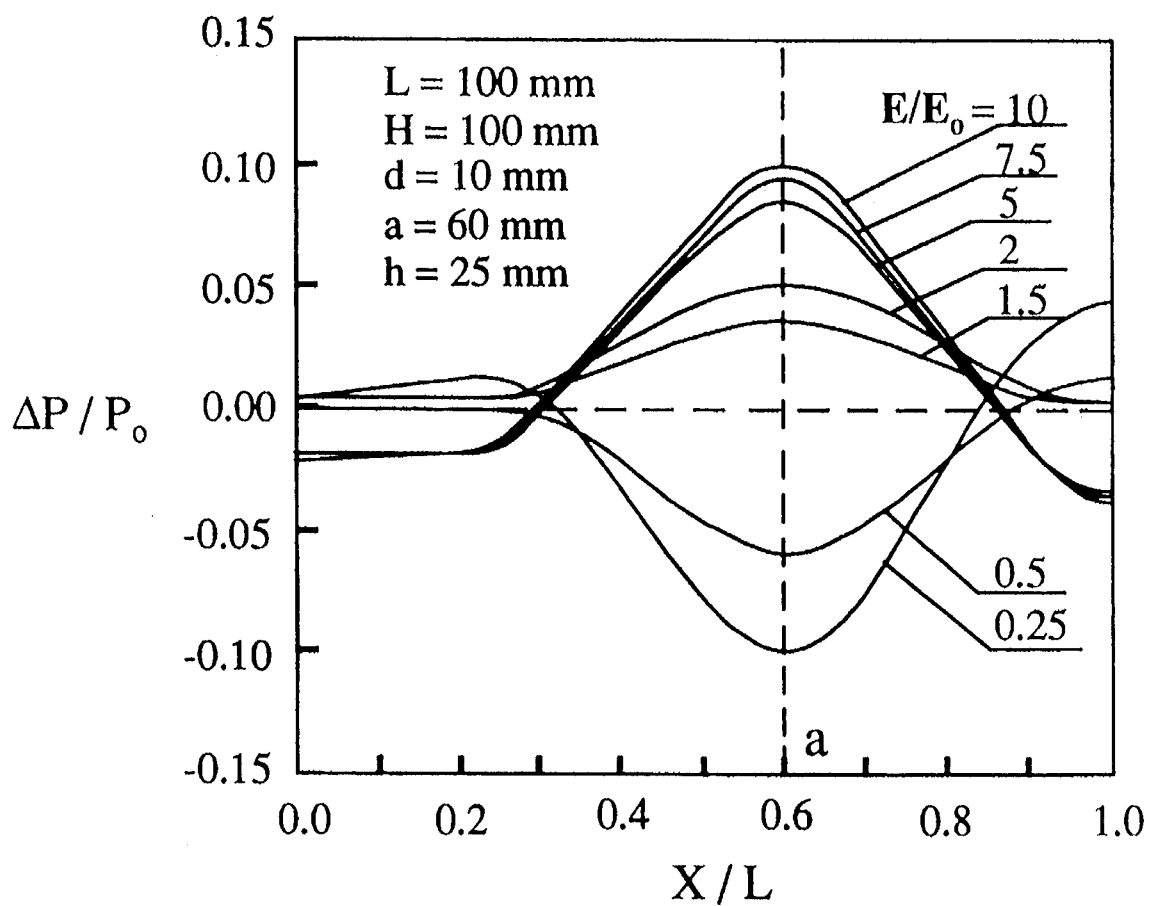
FIG. 5A is a plot of calculated pressure relationships across the surface at differing ratios of moduli of elasticity ratio between surrounding tissue and a tumor.

In FIG. 5, a schematic representation illustrates tissue having a tumor therein of a certain size and location. The graph of FIG. 5A illustrates a particular calculated differential pressure ratio as a function of the distance along the horizontal axis on the surface of the tissue. The graph is based on the dimensions shown in FIG. 5 having certain values, such as those listed in FIG. 5A. The symbol (E) represents the elasticity modulus (Young's modulus) of the tumor and ($E_o$) represents the elasticity modulus (Young's modulus) of the surrounding tissue. A ratio of these two moduli of elasticity ($E/E_o$) provides an indication of the hardness of the tumor relative to the surrounding tissue.

It is known that the Young's or shear elasticity modulus of a tumor varies significantly from the modulus of elasticity for surrounding tissue. For example, solid lumps may have an elasticity modulus of 10 times the elasticity modulus of normal glandular tissue, or relaxed muscle. However, in early stages of tissue differentiation, the elasticity modulus of tumors may not be substantially different from that of normal tissue. FIGS. 5 and 5A illustrate that the differential pressure profile ratio, namely ($\Delta P/P_o$), (a change in amplitude of the pressure sensed at occlusions divided by the pressure in that region of normal tissue) in the region surrounding the tumor is quite sensitive to changes in the elasticity modulus ratio ($E/E_o$).

In FIG. 5, a "block" of tissue 10 has a height H from a base to the contact point with the pressure sensors 15, and has a length L extending along the "X" direction (i.e., horizontal axis). A tumor 30 is positioned in the tissue 10, and is located a distance below the loading plate 12 equal to (h) and it has a diameter (d). Tumor 30 is located along the horizontal axis at a distance (a) from a left edge of the tissue 10.

FIG. 5A is a graph illustrating the differential pressure ratio ($\Delta P/P_o$) (values shown on the vertical axis), as a function of the distance along the X axis from the left edge of the tissue 10 to the right. The position of the tumor 30 at (a) is indicated by a vertical dotted line in FIG. 5A. Several plots of ($\Delta P/P_o$) as a function of (X/L) are shown, each corresponding to a given ratio of moduli of elasticity ($E/E_o$), which indicates the relative hardness between a tumor and normal tissue.

With the parameters having the values shown in FIG. 5A, the plots illustrate that a tumor/tissue combination having an elasticity moduli ratio ($E/E_o$) of only 1.5, i.e., the tumor having a modulus of elasticity of 1.5 times that of the surrounding tissue, a detectable change in the pressure signal is observed for the region surrounding the tumor. This means that even tumors that are not much harder than surrounding tissue can be detected quite easily. It is known that a tumor in a breast, for example, can be detected by a palpation (which is the only technique available for evaluating elasticity), but palpation is reliable only when the tumor has progressed so its Young's modulus is more than five to ten times larger than that of surrounding tissue. The differential pressure signal ($\Delta P/P_o$) shows a more pronounced effect near the tumor when the elasticity moduli ratio ($E/E_o$) is 2 or 5 or more. However, in this case when the elasticity moduli ratio is greater than 7.5 (e.g., 10), there is not a substantial increase in the differential pressure profile above that shown for $E/E_o = 7.5$.

When tumors or inclusions are softer than the surrounding tissue, e.g., the ratio ($E/E_o$) is 0.5, a substantial difference in the differential pressure profile ($\Delta P/P_o$) in the region of the tumor is readily observable. More pronounced effect occurs when the ratio ($E/E_o$) is 0.25. Accordingly, by observing a relatively small change in the pressure profile (only 2–10%), one can detect tumors that have a relatively small change in the modulus of elasticity. This clinically significant data is obtained by using a pressure sensor array extending across the surface of the tissue and external to the tissue that measures a pressure profile response during compression of the tissue as it is described in the co-pending application Ser. No. 07/823,155.

Figure 6:
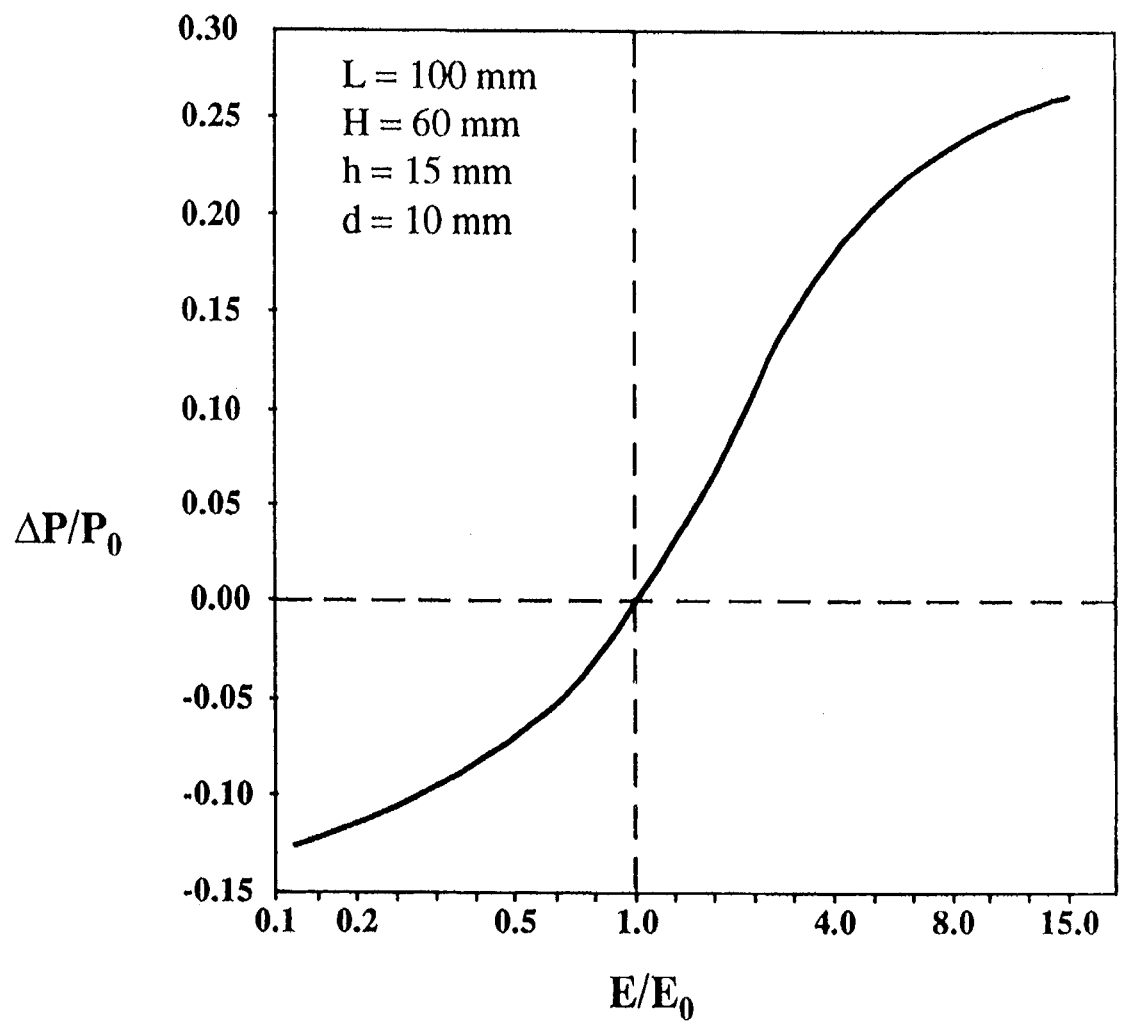
FIG. 6 is a graphical representation of the calculated relationship between pressure ratios and moduli of elasticity ratios for a loading structure shown in FIG. 5.

FIG. 6 illustrates the changes in pressure sensed as a function of the change in the elasticity modulus ratio ($E/E_o$).

Similar to the illustration on FIGS. 5 and 5A, FIG. 6 shows that easily achievable resolution of a few percent in the pressure profile ratio ($\Delta P/P_o$) can enable one to detect inclusions differing from the surrounding tissue in hardness to an extent which does not permit palpatory detection. The graph is based on a tissue block 10 having the parameters such as indicated on FIG. 6. The values on the horizontal axis ($E/E_o$) are provided on a logarithmic basis to facilitate comparison purposes.

Figure 7:
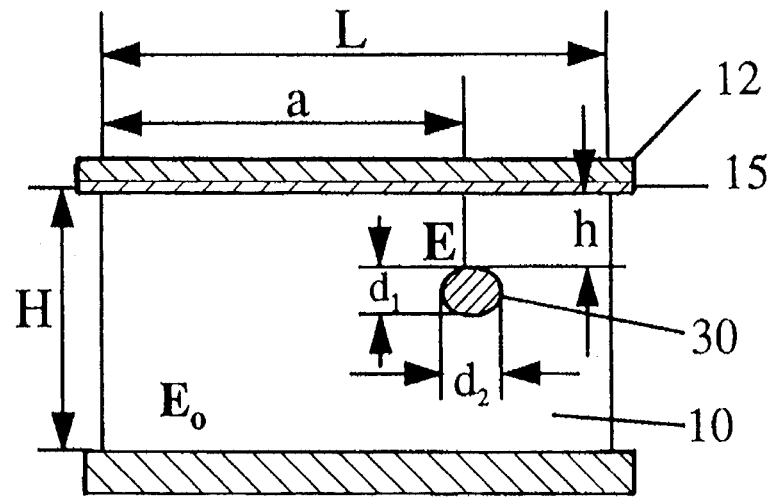
FIG. 7 is a schematic representation similar to that shown in FIG. 5 with certain loading parameters illustrated.
Figure 7A:
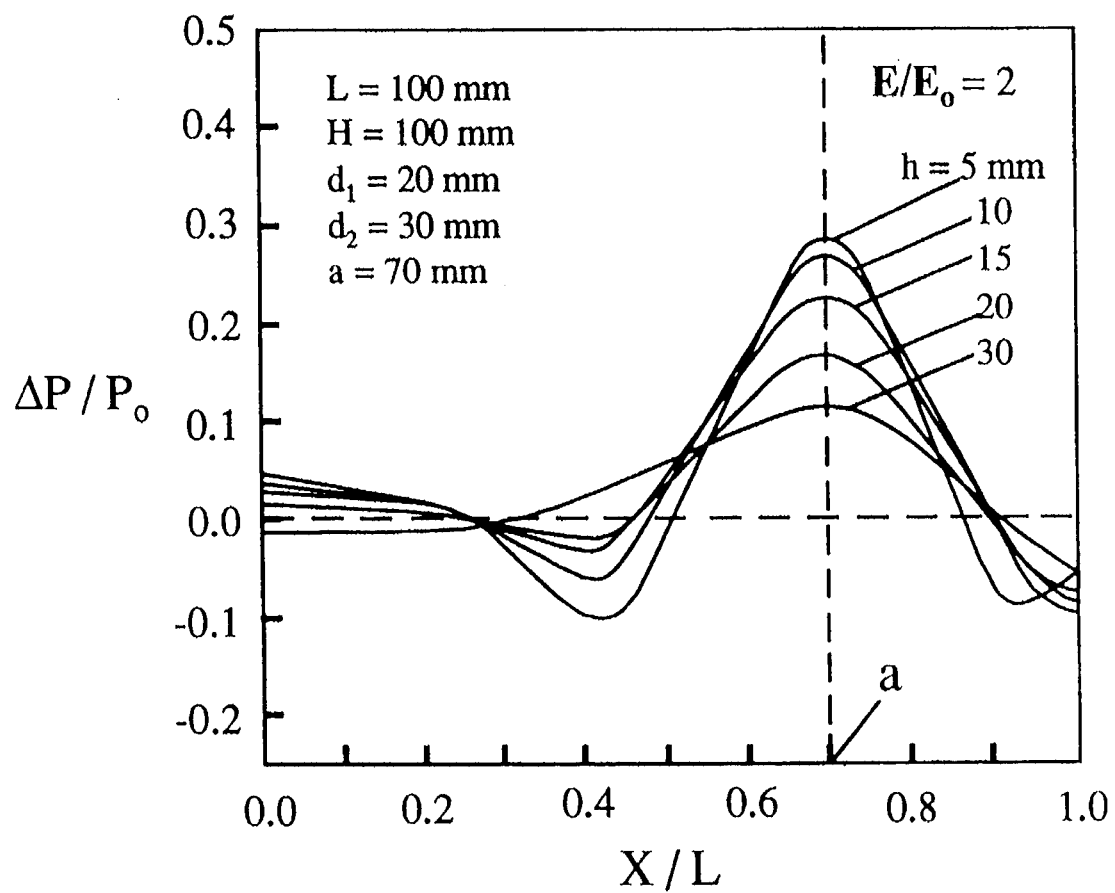
FIG. 7A is a graphical representation of the calculated pressure relationships across the surface at differing depths of a tumor in tissue shown at FIG. 7.

FIGS. 7 and 7A illustrate that the capability to detect a tumor within a block of tissue depends on the distance of the tumor from the tissue surface (skin) and pressure sensors. As seen in FIG. 7, the block of tissue 10 has a tumor 30 located therein and, in this instance, the vertical height of the tumor is represented as d1 and the lateral width of tumor is represented as d2. The parameter (a) represents the tumor's distance from its position from the left side of the tissue block. A set of values for the dimensions shown in FIG. 7 are listed on in FIG. 7A. FIG. 7A shows the calculated plot of the pressure profile ratio ($\Delta P/P_o$) (the change in pressure of tumorous tissue relative to normal tissue divided by the pressure sensed with no tumor) as a function of (X/L) along the X axis. This graph illustrates that a substantial change in the pressure profile ratio ($\Delta P/P_o$) of about 0.3 is observed when the tumor is a small distance (h=5 or 10 mm) from the tissue surface and that a smaller change in pressure profile ratio occurs when the tumor is far from the surface (e.g., h=30 mm). However, even when the tumor is deep (h=30 mm), the pressure profile ratio change is still readily discernible (with ($\Delta P/P_o$) about 0.1 which is quite measurable) to indicate a tissue abnormality at about X/L=0.70. The ratio of ($E/E_o$) is taken to be equal to 2.

Figure 8:
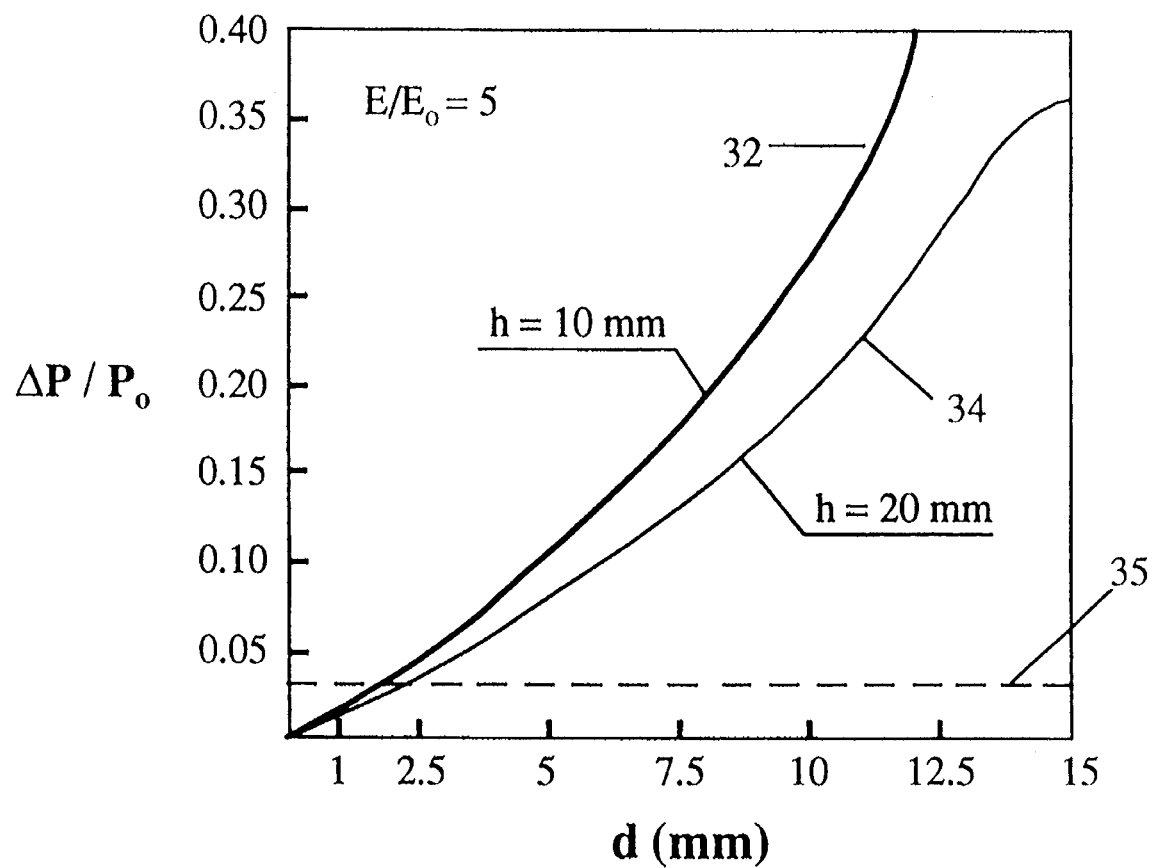
FIG. 8 is a graphical representation of calculated pressure relationships relative to the diameter of a tumor being sensed at differing depth of the tumor as shown in FIG. 5.

FIG. 8 illustrates the effect on the ability to ascertain a change in pressure with the sensors 15 as a function of the change in the diameter d of the tumor. As seen in FIG. 8, the elasticity moduli ratio ($E/E_o$) is equal to five, and the graph shows a plot of ($\Delta P/P_o$) versus d for a tumor with h=10 mm (indicated by line 32) and a tumor with h=20 mm (indicated by line 34). The pressure ratio ($\Delta P/P_o$) at the point of surface above the tumor, is indicated along the vertical axis, while the diameter of the tumor d is indicated along the horizontal axis.

The reference line indicated as 35 is more or less the base line for sensitivity of the ratio ($\Delta P/P_o$) measurement that can be easily obtained with existing pressure sensors. An error of about one percent in pressure sensors is quite common, even with very miniature sensors, and the base line 35 represents a change of about three percent, which will give a clear indication of the presence of a tumor in normal tissue having a diameter (d) in the range of one to two millimeters. FIG. 8 indicates that, the larger the tumor, one observes greater change in the pressure ratio.

In the case of breast tumors, palpation typically reveals tumors only larger than 5–10 mm in diameter. Detection of breast tumors with diameters of about 1–2 mm is a crucial point for providing early diagnostics of breast cancer.

Figure 9:
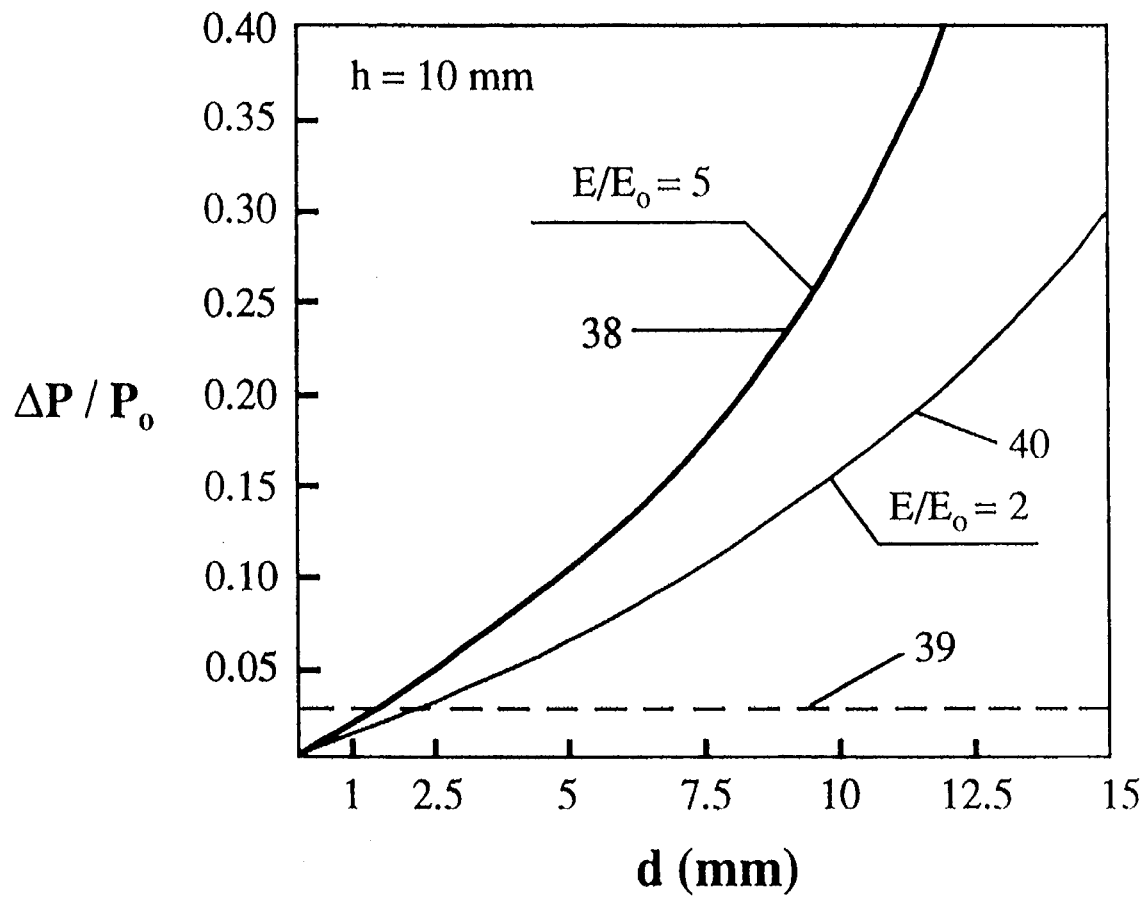
FIG. 9 is a graphical representation of the calculated pressure relationships relative to the diameter of a tumor, at differing ratios of moduli of elasticity between the surrounding tissue and the tumor.

FIG. 9 again illustrates the change in the pressure profile ratio ($\Delta P/P_o$) at the point of surface above the tumor as a function of the diameter (d) of the tumor. However, this time, the depth (h) of the tumor below the sensors 15 is set at 10 mm and a plot is provided for the case when the elasticity moduli ratio ($E/E_o$) equals 5 (indicated by line 38) and when ($E/E_o$) equals 2 (indicated by dashed line 40). As expected, the greater the difference in the elasticity modulus between the tumor and surrounding tissue, (a larger ratio ($E/E_o$)), the more substantial change in the pressure profile ratio ($\Delta P/P_o$) for a given diameter tumor and the more easily the tumor will be detected. Taking the ratio ($\Delta P/P_o$) as an indication of sensitivity, one can observe line ($E/E_o$=5) crossing a threshold level of sensitivity (indicated by the dashed line at 39) indicating that detection of a tumor in the range of 1 mm can be made. When an elasticity modulus ratio is 2 (line 40), one can observe that a tumor of 2.5 mm in diameter (d) could be detected while it is well known that palpation permits detection of tumors in the range of 8 mm to 10 mm, but not smaller. The graph in FIG. 9 shows quantitatively how the detection device (pressure sensors) becomes substantially more sensitive (on a relative basis, i.e., a larger change in the pressure profile ratio ($\Delta P/P_o$) is observed) as the elasticity moduli ratio ($E/E_o$) of the tumorous tissue relative to the normal tissue increases.

Figure 10:
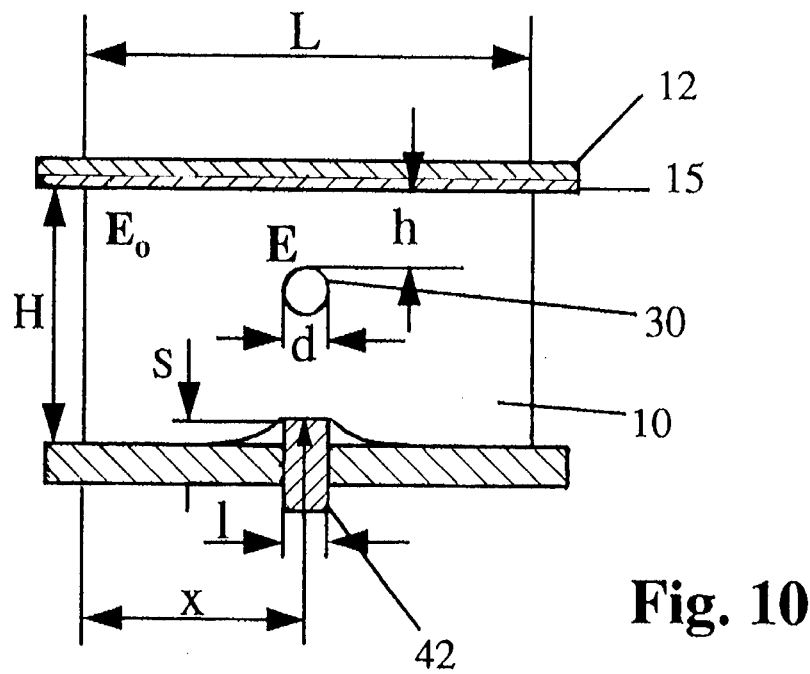
FIG. 10 is a schematic representation of a block of tissue having a tumor therein with a "finger" inserted from a side opposite from a loading plate.
Figure 10A:
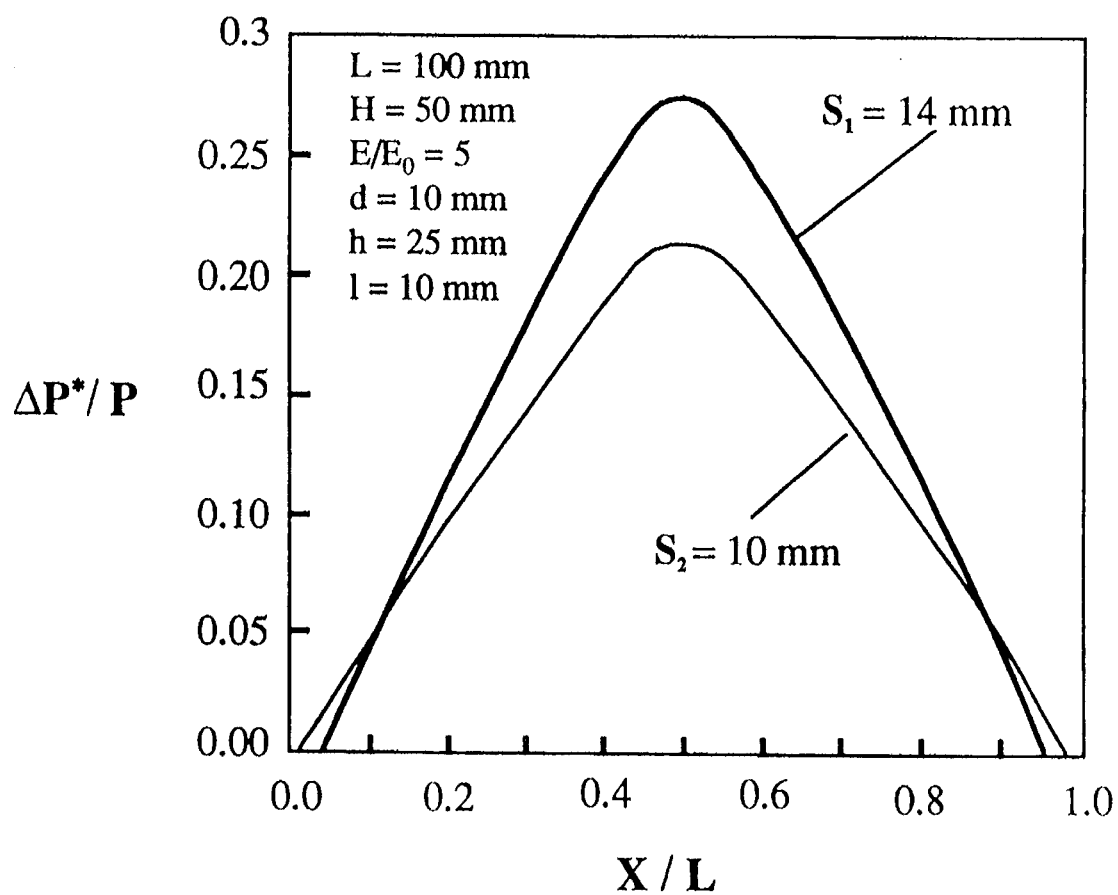
FIG. 10A is a graphical representation related to FIG. 10 illustrating an increase of the resolution of the pressure relationship across the surface relative to position at two different depths of the probe illustrated in FIG. 10.

FIGS. 10 and 10A illustrate the effects of measuring the pressure profile on tissue having an inclusion while providing a "finger" probe or a piston from an opposite side from the main support 12. The sensor array 15 is again in place on the support 12, and the tissue block 10 has tumor 30 located therein. The dimensional notations are the same as those previously used. In this form of the invention, however, a finger probe 42 is applied through the base support into the tissue block 10 as shown, and the penetration distance is labeled as (S). The finger probe is illustrated as being directly below the tumor 30, which has a diameter of (d). FIGS. 10 and 10A provide an example of the sensitivity on the pressure sensors when a finger probe or piston has been applied from an opposite side from the pressure sensing array 15. Taking standard dimensions as shown in FIG. 10A, and with an elasticity moduli ratio ($E/E_o$) of 5, and the diameter of the finger probe (1) as 10 mm, the graph reflects the differences in pressure sensed along the X axis.

In the graph of FIG. 10A, the horizontal axis is X/L, and the vertical axis is $\Delta P^*/P$. The plotted curve represents the pressure profile ratio ($\Delta P^*/P$) as a function of distance along a horizontal axis. When the finger probe or piston 42 has penetrated 10 mm (S=10), the graph is represented by dotted lines, and when the probe has penetrated to S=14 mm, the graph represented by a solid line. This graph illustrates that the use of a finger probe, which simulates a probing human finger applied to tissue, accentuates the pressure profile differential in the location of the tumor, making the tumor even easier to detect than without the probe. The graph also illustrates that the greater the penetration (S=14 mm), the greater the pressure profile change (i.e., sensitivity), particularly near the center of the tumor.

Figure 11:
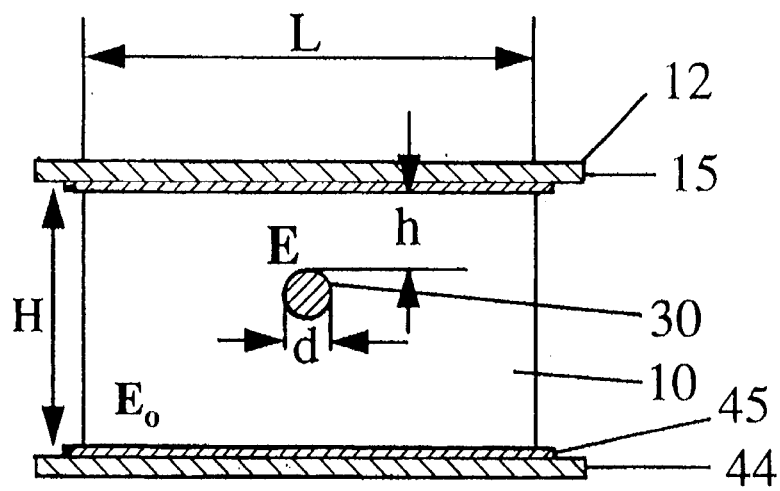
FIG. 11 is a graphical representation of a portion of tissue with pressure sensors on each of the loading plates.
Figure 11A:
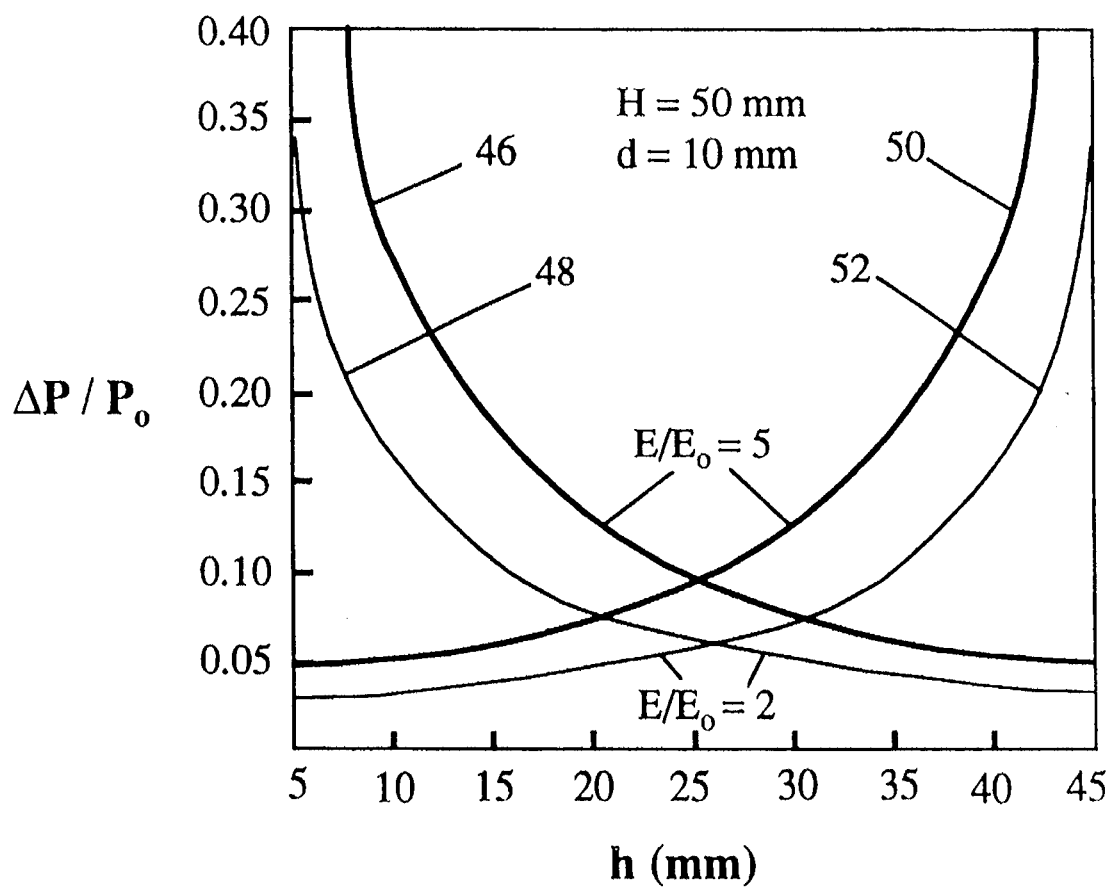
FIG. 11A is a graphical representation of the pressure relationships and sensitivity relative to the distance of a tumor from the sensors being used at differing ratios of moduli of elasticity between the surrounding tissue and the tumor.

FIGS. 11 and 11A illustrate that pressure profile sensitivity can be enhanced by having pressure sensor arrays on both sides of the tissue block. For example, the plate 12 and pressure array 15 would be on top of tissue block 10, and a second plate 44 having a pressure array 45 thereon is below and supporting tissue block 10. As in the previous illustrations and examples, the block of tissue 10 with the tumor 30 therein will be compressed a desired amount. The dimensional notations are also as shown before. The graph of FIG. 11A illustrates the pressure profile ratio ($\Delta P/P_o$) at the point of surface above the tumor (i.e., sensitivity) change as a function of the height h, which is the distance from the top of the tumor 30 to the upper pressure array 15. The height H of the tissue block is a nominal 50 mm and the tumor has a diameter (d) of 10 mm.

Calculated values show a decrease in the sensitivity of pressure changes measured by the top pressure array 15 as h increases (from 5 to 45 mm). Plots 46 and 48 illustrate a decrease in measuring pressure sensitivity the further the tumor is away from the upper pressure array 15. Similarly, the plots 50 and 52, respectively, show the increase in sensitivity for detection of a tumor at the bottom pressure arrays 45 when the tumor is closer to the pressure array 45. For the bottom sensor array plots 50 and 52, the elasticity moduli ratio ($E/E_o$) is 5 for line 50 and the elasticity moduli ratio is 2 for line 52. Accordingly, when the sensitivity of a single pressure array decreases because the tumor is far from the tissue block surface, one can compensate by adding a second pressure sensor array so that a pressure sensor array is on each side of the tissue block being sensed.

Figure 12:
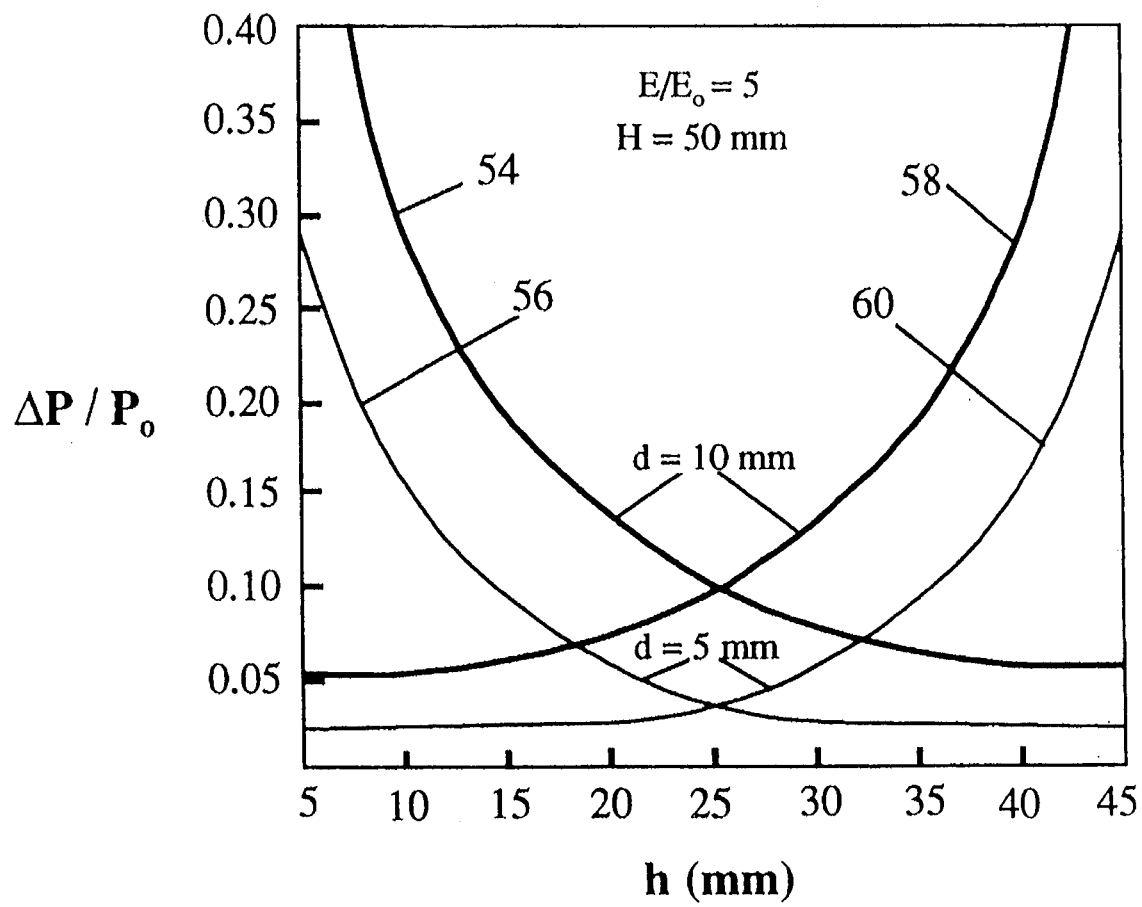
FIG. 12 is a graphical representation illustrating the sensitivity to the depth of a tumor as related to the size of the tumor as shown in FIG. 11.

FIG. 12 illustrates essentially the same conditions as shown in FIGS. 11 and 11A. However, FIG. 12 illustrates this effect for a single elasticity moduli ratio ($E/E_o=5$) but with two different tumor diameters (d=10 mm and d=5 mm). In FIG. 12, the curve corresponding to the pressure sensed by the pressure sensing array 15 is illustrated by curves 54 and 56, and it shows the pressure sensed decreasing as h (the distance between the tumor and array 15) increases. The curve 56 illustrates this relationship with the tumor having a diameter (d) of 5 mm and curve 54 corresponds to the tumor having a diameter (d) of 10 mm.

Curve 58 illustrates the sensitivity of the bottom pressure sensing array 45 (FIG. 11) with a diameter of the tumor at 10 mm and the curve 60 illustrates the sensitivity at the array 45 with the tumor having a diameter of 5 mm. As expected, FIG. 12 shows that a greater pressure change is sensed for larger diameter tumors. Moreover, as the distance of the tumor from the upper array 15 increases resulting in lower measuring sensitivity from the top, the distance between the tumor and bottom array 45 decreases resulting in higher measuring sensitivity from the bottom.

From the illustrations of FIGS. 11, 11A, and 12, it can be seen that the use of two pressure sensing arrays on opposite sides of the supported tissue block 10 provides an opportunity for better detection of tumors farther from the tissue block surface.

FIGS. 13A, and 13B illustrate a tumor in tissue located on the chest adjacent to ribs, and FIGS. 13B and 13C illustrate that shifting of the pressure sensor while contacting the tissue accentuates sensitivity of detection for the tumor.

In FIG. 13A, a rib cage 64 is illustrated schematically as having two ribs 66 shown in cross-section and held adjacent to each other with normal connective tissue. A quantity of tissue, such as breast tissue, is indicated at 68 and is positioned between the ribs and an outer surface of the tissue, against which a pressure plate 70 is placed, which has a pressure array 72 thereunder. Force is applied as indicated by the arrow 74 in FIG. 13A. A tumor 76 is located adjacent to and midway between the ribs 66. The distance between the centers of the ribs is indicated as (a), and the width of the ribs is indicated as (1). The height of each rib above the general support plane of the tissue is indicated by (S). The profile of pressure sensed by an array 72 is indicated at the top of FIG. 13A, with the maximum pressure detected corresponding to a position directly above the tumor 76.

In a laterally shifted position as shown in FIG. 13B, the pressure plate 70 has been shifted relative to the ribs 66. This tends to move the tumor 76 closer to one of the ribs, as shown. The tumor is now in a position where it is very near or substantially over a rib. This changed positioning of the tumor is reflected by the substantial increase in the peak of pressure profile illustrated at the top of FIG. 13B. In this case, a change in the pressure profile because of the lateral shift is represented as $\Delta P^* = P^* - P$. The lateral shift of the pressure plate 70 and pressure sensor 72 can be measured from a starting value. Although a lateral shift occurs in the X direction, the amount of shift will be indicated by "Z" in FIG. 13C. The increase of pressure sensitivity ($\Delta P^*/P$) is marked on the vertical axis, and the horizontal axis indicates an X dimension, which has a zero point at the peak pressure in FIG. 13B.

The graph of FIG. 13C calculated with the use of the mathematical approach described above illustrates the change in pressure profile ($\Delta P^*/P$) (after a lateral shift of the pressure plate 70) as a function of the distance X laterally away from the center of the pressure profile peak for $P^*(x)$. Plot 78 illustrates this relationship for a lateral shift of 7 mm of the pressure plate relative to the stationary rib cage (the difference shown between FIGS. 13A and 13B), and plot 80 corresponds to a lateral shift of 18 mm.

In this example, the distance between the center of the ribs (a) is 25 mm and (1), which is the width of the rib, is 20 mm. The other dimensional parameters are illustrated at FIG. 13C. The graphs indicate that a greater pressure measuring sensitivity is achieved in detecting a tumor in a breast (or other tissue) when the pressure plate is shifted laterally while in contact with the tissue. This is particularly true when the underlying tissue includes a bony structure such as ribs which are adjacent the tumor and over which the tumor will be moved during the shift.

In particular, the form of the invention shown in FIGS. 13A, 13B and 13C is especially useful for imaging of breast tissue with tumors situated close to the chest. When a tumor is close to a rib (see FIG. 13A) the approach described above and shown in FIGS. 1–12 as well as ordinary probe techniques, such as palpating or conventional ultrasound, cannot detect the presence of the tumor. However, when the pressure sensing plate 70, having pressure sensor 72 thereon is rolled transversely to the ribs (i.e., the lateral shift) the tumor can be detected easily because of an increased resolution created by rolling the tissue. Indeed, when the tumor is moved near a rib, the rib acts much like the piston/probe 24 shown in FIGS. 10 thereby accentuating the peak of the pressure profile corresponding to the location of the tumor or inclusion.

The function $P^*(x)$ is shifted laterally reflecting that the peak and baseline of the pressure profile shift. This indicates that there is a harder portion of tissue between the ribs and the surface being pressed upon. If lumps are discovered in this manner, mammography or ultrasound can be utilized for analyzing the internal structures in the region of interest.

Figure 14:
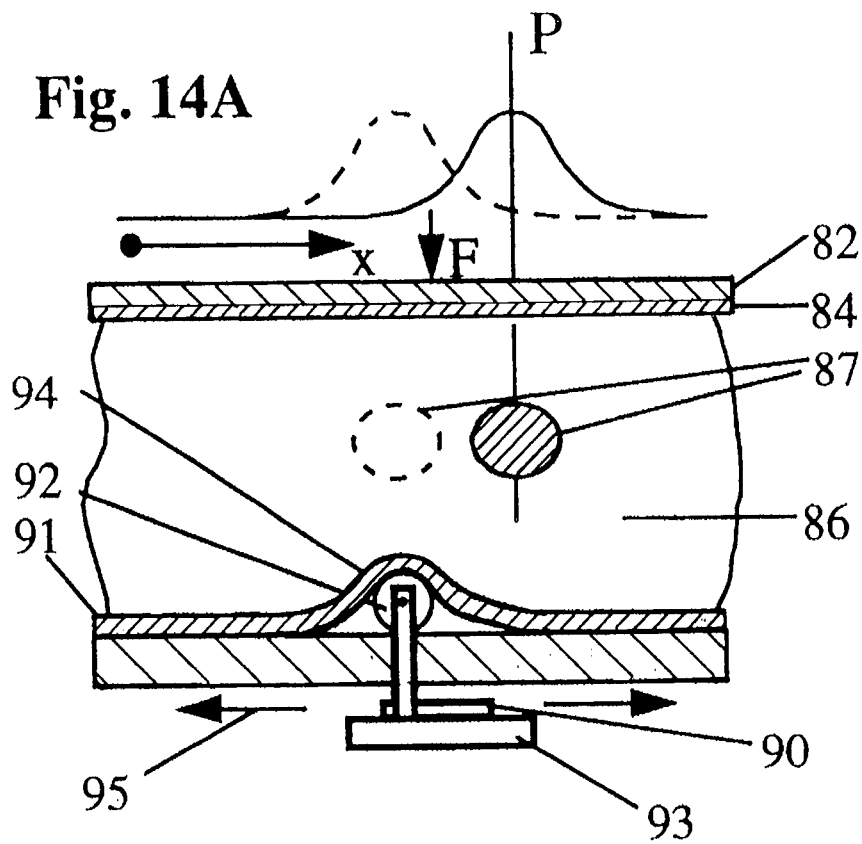
FIG. 14 illustrates a section of tissue being held against a support plate wherein a roller can be rolled along a pad directly applying deformation forces to the section of tissue.

In FIG. 14, a device is shown schematically wherein a roller is moved along a section of tissue, and analysis of the differing pressure patterns is made while the roller is being so moved. As shown, a support plate 82 has a number of force sensors 84 thereon in a desired array, and the support plate 82 which also can be backed by a movable force-applying member, is acting against tissue 86. A tumor 87 is located in this tissue.

The lower support is a flexible or semi-rigid sheet 91 against which a roller 92 is pressed through the use of a support carriage 90 mounted on a suitable track 93 for movement in direction laterally as indicated by the double arrows 95. The roller 92 will thus roll along the tissue and cause a raised area 94 of the pad or support 91 to exert a greater deformation of the tissue 86 in a localized area immediately above the roller.

As it rolls along, the tumor 87 will tend to shift from the dotted line position shown at 87, and the stress relationship (as graphed in FIG. 14A) will also shift as the tumor shifts, giving an indication that there is some type of a dislocation in the tissue or different hardness tissue that will shift when the roller is rolled. Again an examination of the stress relationship can be used for determining presence of a tumor, evaluating their hardness and making judgments about its character.

Figure 15:
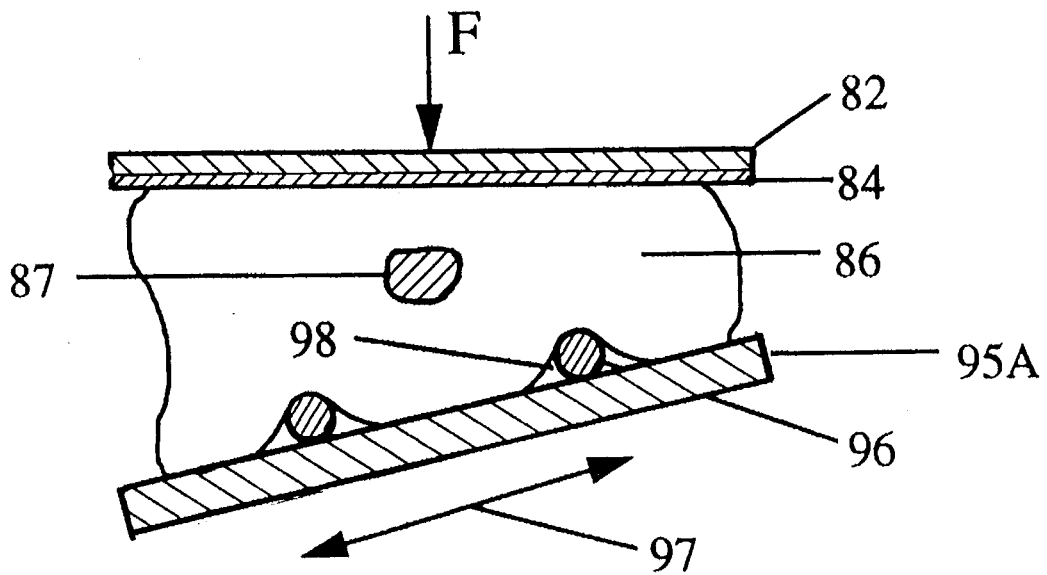
FIG. 15 is illustrative of a deformation device which includes two round rods that provide pressure at known spaced apart pressure lines.

FIG. 15 is a slightly modified form of the invention from that shown in FIG. 14, and includes a support plate 82 having pressure sensors 84 thereon, against which a tissue 86 is pressed. The exertion of force can be merely reaction, with the lower plate shown at 95A being capable of being moved toward the support plate 82 as well as moved in directions indicated by the arrow 97. A pair of rods that are indicated generally at 96 and 98 can be used for applying localized increased loads or increased deformation of the supporting tissue 86 to increase (to a certain extent) the ability to detect the presence of a tumor 87 in such tissue and decrease the error in calculating relative elasticity of the tumor due to the higher gradients of mechanical stresses in the tumor due to higher vicinity of the rollers or rods.

Figure 16:
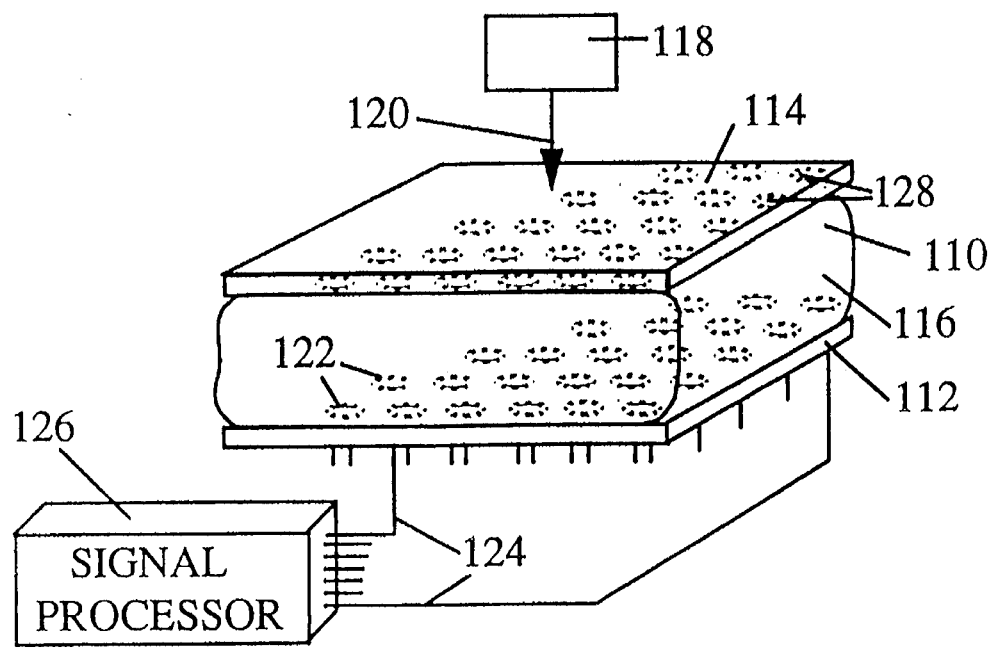
FIG. 16 is a schematic representational view of force-applying plates similar to that shown in FIG. 5 or FIG. 11 having an array of sensors thereon on at least one of the plates.

In FIG. 16 a simplified structure for applying deformation to living tissue wherein a quantity of tissue indicated generally at 110 is placed against a support member 112, and a pressure plate 114 is applied to an opposite side of the tissue. Tissue 110 could be breast tissue or could be muscle tissue from a forearm or upper arm, or the like. The edges of the tissue are shown as being defined by boundaries which comprise skin 116. The ends of the tissue could be joined with covering tissue such as skin or joined to other tissue, and could still connected to the human body. The section illustrated is merely intended to be illustrative of the principles involved.

A force-generating device 118 such as a load frame or compression loading frame, which is servo-controlled to provide a known amount of force indicated by the load arrow 120, will be applied to the tissue. The force generator device is capable of being relaxed as desired.

The support plate 112 has an array of individual pressure sensors 122, each of which will provide an individual signal along a line 124 to signal processing equipment 126. The equipment 126 can provide signals to suitable control systems such as in a computer or right back to the operator, so that the operator can adjust the pressure levels to achieve the desired pressure or force across the surface of the support pad 112 which altogether will provide obtaining pressure profiles over the surface of the of the tissue and calculate three-dimensional distribution of internal structures and their relative elasticities. Suitable pressure sensors indicated at 128 also can be carried on the plate 114 in order to increase resolution in detecting deeply situated tumors and evaluating their elasticity, as it was illustrated in FIGS. 11 and 11A.

Thus, FIG. 16 represents a direct force application and a pressure or force readout system that gives the ability to analyze internal structure variations and calculate elasticities of these structures using the data on pressure variations across an array. The pressure sensor array can be on both sides of the tissue.

Figure 17:
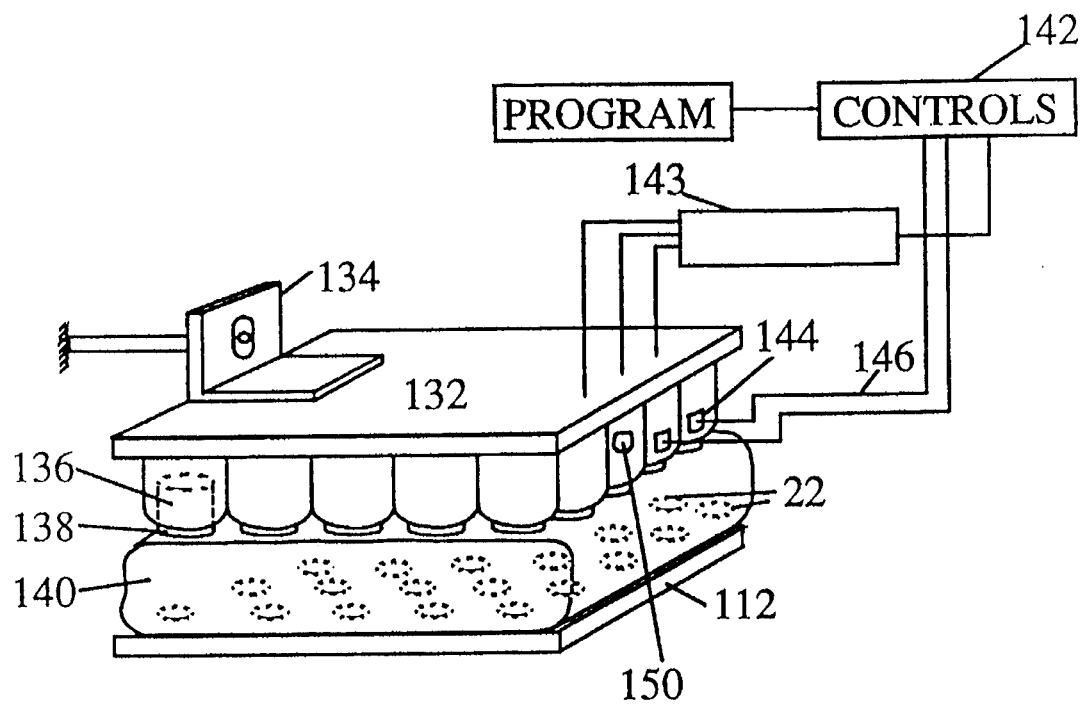
FIG. 17 is a schematic representation of a multiplicity of individual actuators compressing a portion of tissue against a reaction plate having an array of pressure or force sensors.

FIG. 17 illustrates a variation of the device of FIG. 16, and can include the same type of a backing plate 112, but in this instance the plate 114 and load member 118 are replaced by a backing plate 132 which can be adjustably fixed in spaced relation to the support plate 112, for example, by an adjustable bracket 134. The plate 132 has a number of individual fluid pressure actuators 136 mounted thereon in an array, and as shown, they are closely spaced. Each of the actuators is formed with a piston on the interior of a cylinder, and each piston has an outer rod portion 138 that has an end surface engaging tissue (indicated at 140) which is supported on the plate 112. The individual actuators 136 have controls 142 controlling suitable servovalves 143 to, in turn, control the fluid pressure in each of the actuators and thus to control the force applied in a local area by the end of the rod. A force feedback sensor indicated at 144 is provided to determine the force exerted by each actuator. Sensor 144 in turn provides a feedback signal along a line 146 to the controls 142 to indicate whether or not a pre-programmed force from a program for operation of each actuator is being met. These control systems for actuators are closed loop servosystems. Separate channels are used for each actuator and the pressure will be adjusted to equal the desired pressure. Closed loop servosystems generally use hydraulic actuators so that precise piston position, as well as the load can be obtained. The position of the rod ends 138, which form flat surfaces bearing on the tissue, can be sensed relative to the base plate 132 by using position sensors that can be internal of the actuators, that is, internally located within the cylinders, to sense the position of the respective pistons relative to the base plate 132. Such a sensor is illustrated schematically at 150 and will provide feedback signals to the controller 142 as well. The control of actuator position and/or force permits simulation of palpation by varying the force on each actuator to achieve the desired compression or displacement of underlying tissue.

FIG. 18 is a schematic representation of a further embodiment of the invention which includes actuators on the top and bottom of the tissue being examined. The actuators shown at 136 are the same as those of the device of FIG. 17, and can be programmed and controlled as shown in FIG. 17. The rod end 138A shown on the top of the tissue in FIG. 18 is extended more fully to provide a greater displacement to the tissue 140 than in the form of the invention shown in FIG. 17. The ends 138A of the rods can be formed to have a plurality of individual resistance stress gauge sensors, or some type of a force deflectable diaphragm sensor to sense forces in a localized area on the end of the rod, or to sense total force being exerted by the respective rod. FIG. 18A illustrates such an arrangement, where individual force sensors 160 are on the end of the rod 138A to sense forces in a localized area.

The second array of actuators 162 is mounted on a support plate 164 that in turn is formed and supported on a suitable base that is fixed relative to the support member 134 for plate 132. The actuators 162 have rod ends 166 that are operated with an internal piston, and can have force sensors 160 on the end as shown in FIG. 18A, as well as internal pressure sensors for determining the total force being exerted by each piston on the tissue 140. Displacement sensors also are utilized with the rods 166 to determine the position of the end of the rod relative to the base plate 164. The force and displacement sensors on the actuator provide feedback signals for control, while sensors 160 indicate variation in reaction forces in regions of tissue being displaced.

By using multiple channel controls, with one control signal to each of the actuators from a control system 168, the actuators can be controlled to extend some of the rods 138 a greater amount relative to others. Also, the controls can cause some to extend a greater amount on the bottom of the tissue, as illustrated. Actuators 162A and 136B, at the bottom and top, illustrate probing to change conditions for examination of elasticity of the tissue in the manner described above. Examination can take place also by the use of a suitable imaging apparatus illustrated generally at 170. The imaging apparatus 170 to evaluate changes of strain profiles during loading of tissue can be selected from known devices, such as MRI or ultrasonic imaging devices.

FIG. 19 shows a modification of the actuator construction, and is similar to FIG. 17. This embodiment includes a base plate 112 for supporting tissue 140, and a reaction plate 132 that is suitably supported on a support bracket 134. The individual actuators 180 are mounted onto the plate 132 in a conventional manner, and have outer cylindrical housings 182. The housings 182 have internal pistons that actuate rods 184 with smaller diameter end portions 188. The pressure in the interior cylinder is controlled through a suitable servovalve 192, respectively, to control the force indicated by the arrow 196 on the piston. If desired, the portions 188 can be separate pistons nested in the main piston 184. Suitable known controls 198 are provided for controlling the servovalves (one for each actuator) and for receiving feedback signals along lines from pressure sensors 186 that sense pressure in each of the respective actuator chambers, and displacement sensors 187 which provide displacement feedback signals.

The feedback signals relating to displacement from sensors 187 indicate the position of the respective piston rod 184 and smaller end portion 188 relative to the base of the associated cylinder housing 182. Thus, the controls 198, which are conventional servovalve feedback error signal controls, can regulate the position of each of the piston rods individually, as well as the force being exerted by the pistons, and relate that force to the piston rod position. The actuators can be operated to all be at the same position, or selectively at differing positions to provide for differing strain pattern distributions on tissue 140 that can be sensed by a suitable scanner such as an ultrasound scanner 199 or an MRI scanner.

FIGS. 20A, 20B, and 20C and corresponding pressure pattern graphs at 20A-1, 20B-1 and 20C-1, show the effects of modifying the locations and directions of force, and the movement of a tumor during differing force direction applications. FIGS. 20A, 20B and 20C show a support plate 200, which is shown in a fixed, generally horizontal position in each of the figures. The plate 200 has an array of pressure sensors 201 thereon for sensing the pressure exerted toward the plate 200 on a section of tissue 202. A tumor 202A is shown in this tissue, and it can be determined that the tumor will shift from a rest position when loaded with a pivoting plate such as that shown at 203.

The pivoting plate can be mounted on a central axis or pin 203A and a torque to pivot the plate is created to tilt the plate first in one direction as shown in FIG. 20A, then to hold it steady as shown in FIG. 20B, and then to tilt in the other direction is shown in FIG. 20C. The shifting of the peak of the surface pressure distribution caused by the shifting of tumor 202A can be observed, as shown in 20A-1, 20B-1 and 20C-1. Pressure or force changes are sensed by the sensors 201, and an analysis of the elasticity of the tumor 202A, and its relative size can be made from the information contained in the graphical representations of FIGS. 20A-1, 20B-1, and 20C-1.

A schematic representation is shown in FIG. 20B of a typical pivoting support and drive. The support includes a loading support base 204 that can be adjusted to provide for different total loads on the tissue through the use of actuators 204A. The actuators 204A can be adjusted to bring plate 203 closer to or farther away from the backing plate 200, so that at a centered position of the pivoting plate 203, in particular, the total force applied to the tissue could be changed. The tilting of the support plate 203 can be carried out through the use of a lever 204B that is drivably mounted on the support pins 203A. The lever 204B is operated with an actuator 204C that in turn is supported on the loading plate 204. In this manner, the total load on the tissue can be changed and the plate pivoted to provide for differing angular loading conditions as desired for determination of the presence of, and characteristics of the tumor 202A.

The graphs 20A-1, 20A-2 and 20A-3 show shifting positions of pressure peaks $P_{max}$ when the pivoting plate causes a shifting of the tumor. This aids in determining presence of a tumor, as well as its characteristics.

Essentially the same type of loading arrangement is present in FIGS. 21A, 21B and 21C, but in this case, both the plates engaging the tissue may pivot relative to each other. Support plate 200A has pressure sensors 201 thereon, as previously explained, but it is in turn supported for pivotal movement relative to its support 200B, and can be pivoted through the use of an operator as shown in FIG. 20B, and can have adjustments as to its deformation of the tissue 202. The lower plate 203 can be mounted just as shown in FIG. 20B. The different loading directions ensure a variety of load conditions for enhanced analysis.

In FIG. 21B, a modification of the lower plate is shown, and it includes three separate small pivoting plate sections 205A, 205B and 205C which can be individually pivotally to create variations in force across the width of the tissue 202 that is being examined.

Figure 22:
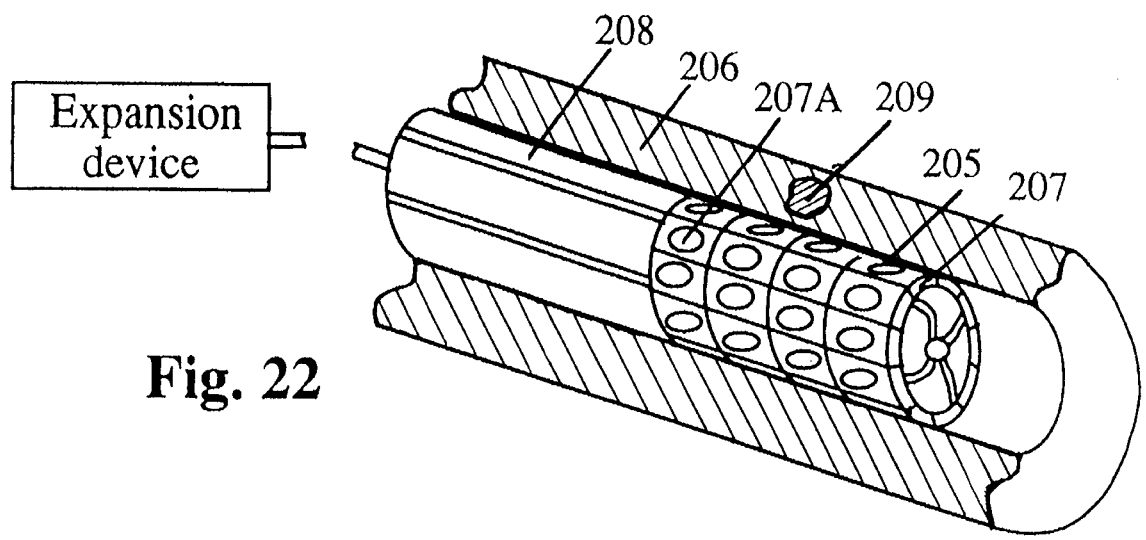
FIG. 22 is a schematic representation of a deformation device for intracavity use such as e.g. in a rectum and made according to the present invention.
Figure 23:
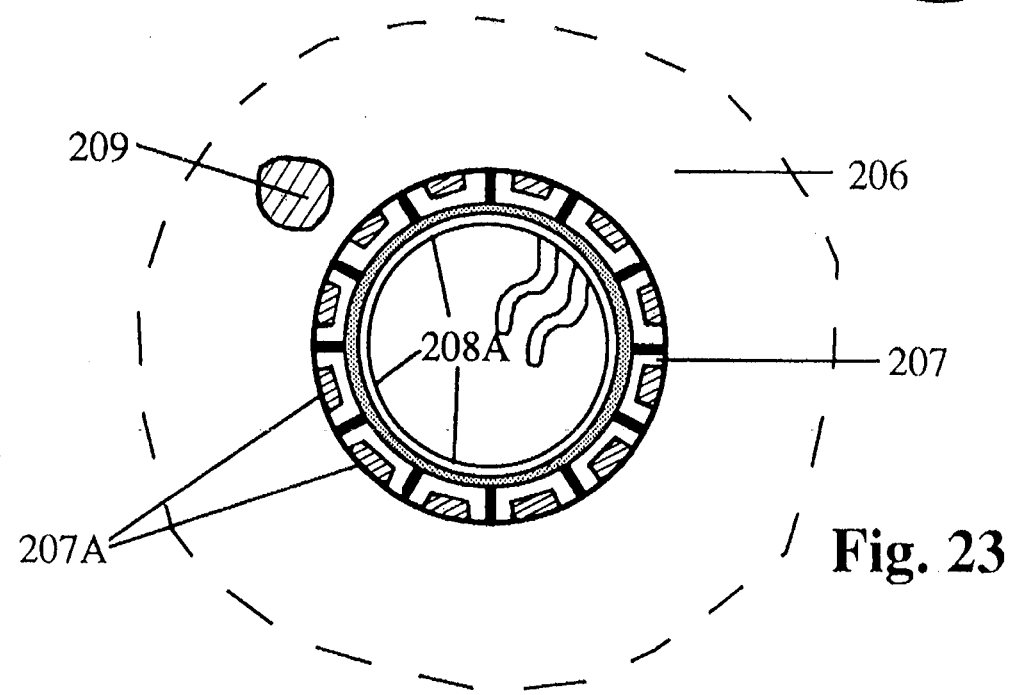
FIG. 23 is a cross-sectional view of the device shown in FIG. 22.
Figure 24:
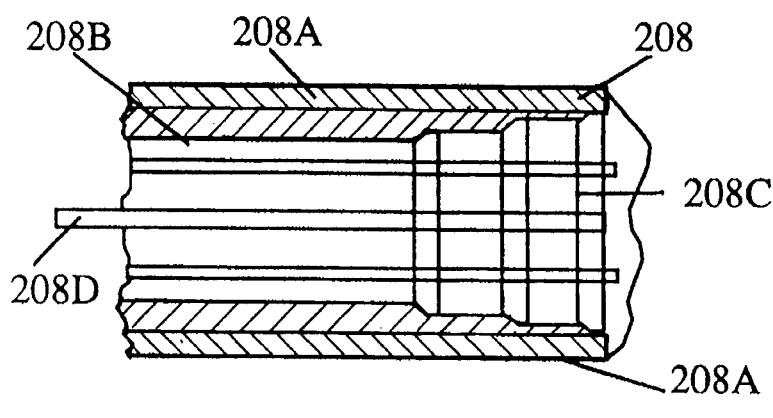
FIG. 24 is a schematic longitudinal sectional view of the device shown in FIG. 23.

In FIGS. 22, 23 and 24, a perspective view of a bodily conduit such as e.g. rectum is schematically shown and a device for deforming the bodily conduit wall tissue and sensing forces on internal wall structures is illustrated. The system includes a center probe or core 208 that has an array of pressure sensors 207 positioned annularly around it, along a desired length. These pressure sensors 207 can be mounted on a band of material that wraps over the expandable probe and supports with pressure or force sensors formed or supported onto the exterior of the layer of material. The pressure array sold by Tekscan Incorporated, 451 D Street, Boston, Mass., U.S.A., can be used. Polyamide films also have been used with strain gauges formed on the surface.

The supporting band for the sensors can be a thin steelband wrapped over the probe and capable of expanding when the probe is expanded. The band can have a longitudinal gap that separates as the probe expands. The band and/or the probe resist inward forces without deflecting when the probe is expanded while the pressure sensors sense pressure in localized areas.

Individual sensing blocks which are indicated at 207A on the drawings are provided. The pressure sensor array 207 is illustrated as being thicker than that which is normally used, but if desired, the sensor array can have a thickness so that the pressure sensor regions 207A can be made as deflecting diaphragms and utilized for sensing individual forces that are exerted radially inwardly along an annular wall of a bodily conduit 216, such as a rectum. The probe or core 208, as shown, is tubular and has a central passageway 208A, with a wall 208B that can be expanded after positioning it in the lumen, either by applying internal pressure or by mechanically expanding the diameter a known amount.

As can be seen in FIG. 23, which is a cross-sectional view, the wall of the conduit 206 is engaged by the pressure sensing array 207. The conduit wall can be stretched a known amount after the pressure sensing array 207 and the probe 208 are inserted. The probe is expandable at least a known amount so the pressure pattern can be determined when a known displacement of the vessel wall has occurred. For example, a radially segmented probe of substantially rigid sections as shown at 208A in FIG. 24 can be used. The segments 208A are retained together annularly and can be collapsed inwardly for insertion into the conduit and then expanded a known amount by use of a cam or wedge plug on the interior.

In FIG. 24, a schematic representation of a cam and plug type expander is shown. Each segment 208A can have a stepped cam-like interior surface formed. These cams are shown at 208B and cause a decrease in internal diameter toward the remote end of the probe. A plug 208C is mounted in the interior of the probe 208 and can be slid longitudinally with a control rod 208D after the probe is inserted in the conduit. The segments 208A will expand radially outwardly. The expansion can be done in steps so that initial contact with the conduit wall 206 can be made (as recorded by the pressure sensors) and then a known expansion or displacement of the conduit wall can be made. The pressure profile around the conduit can be determined.

A pressure containing bag or interior covering can be used on the interior of the probe or core to pressurize the probe from the interior and provide expansion and loading against the conduit wall when a steel band is used to support the pressure sensors from local inward deflection. A tumor or lesion indicated at 209 on one side of the conduit wall will cause a localized different surface pressure reaction than normal tissue around the wall. Each of the individual sensors 207A forming the array is capable of sensing pressure or force in a localized area of the conduit wall. The probe 208 includes means for applying internal force to move the pressure sensors against the surface of the bodily conduit, and thus create a variation in forces being sensed by the sensors. The pressure pattern across the array of sensors 207A (as a function of pressure or displacement of the probe wall) will indicate temporal and spatial features of conduit wall elasticity. The pressure profile will be analyzed as previously explained, for indicated differences in the elasticity of the conduit wall 206 and an inclusion (e.g. a prostate tumor) 209.

The pressure signals can be quantified by a recorded history of the pressure matrix of a conduit wall and a computerized analysis determination can be made to provide diagnostic information. Other conditions also can be evaluated by using the pressure sensors 207A such as muscle condition, which will be reflected by pressure patterns obtained during different muscle conditions, such as contraction and relaxation. The structure and viscoelastic properties of underlying tissues can be visualized and analyzed.

Suitable signal carrying wires can be mounted through the center of the probe and lead to exterior circuitry. Each of the individual sensors also can be expanded by injecting fluid into the interior when such sensors are formed as closed elastic chambers. Increased radial pressure can be exerted by inflating the tube or probe 208 when it is made of elastic material to expand it outwardly due to internal pressure. Again, the analysis can be made as previously explained, and by varying the deformation of the conduit wall 206, the differences in resistance to deformation of the tumor 209 will be seen as a change in pressure in that region. Thus, not only can deformation force be applied from the exterior of tissue as in earlier embodiments of the present invention (e.g. embodiment of FIG. 16), but it also can be applied from the interior of tissue structures (e.g. within a lumen of a bodily conduit) such as with the device described in connection with FIGS. 22–24.

Figure 25:
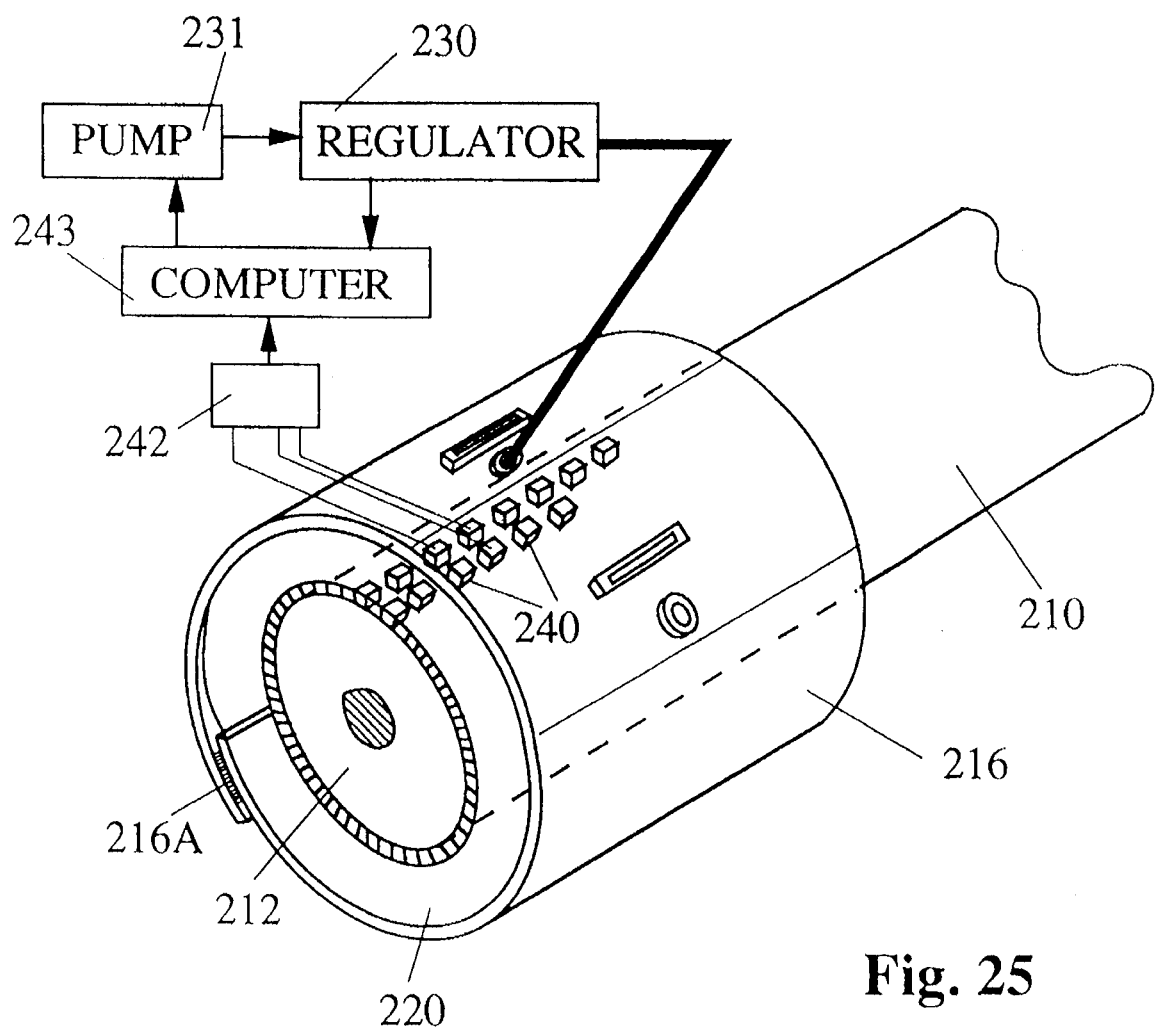
FIG. 25 is a perspective view of a cuff having pressure sensors thereon, and pressure-applying means made according to the present invention.
Figure 26:
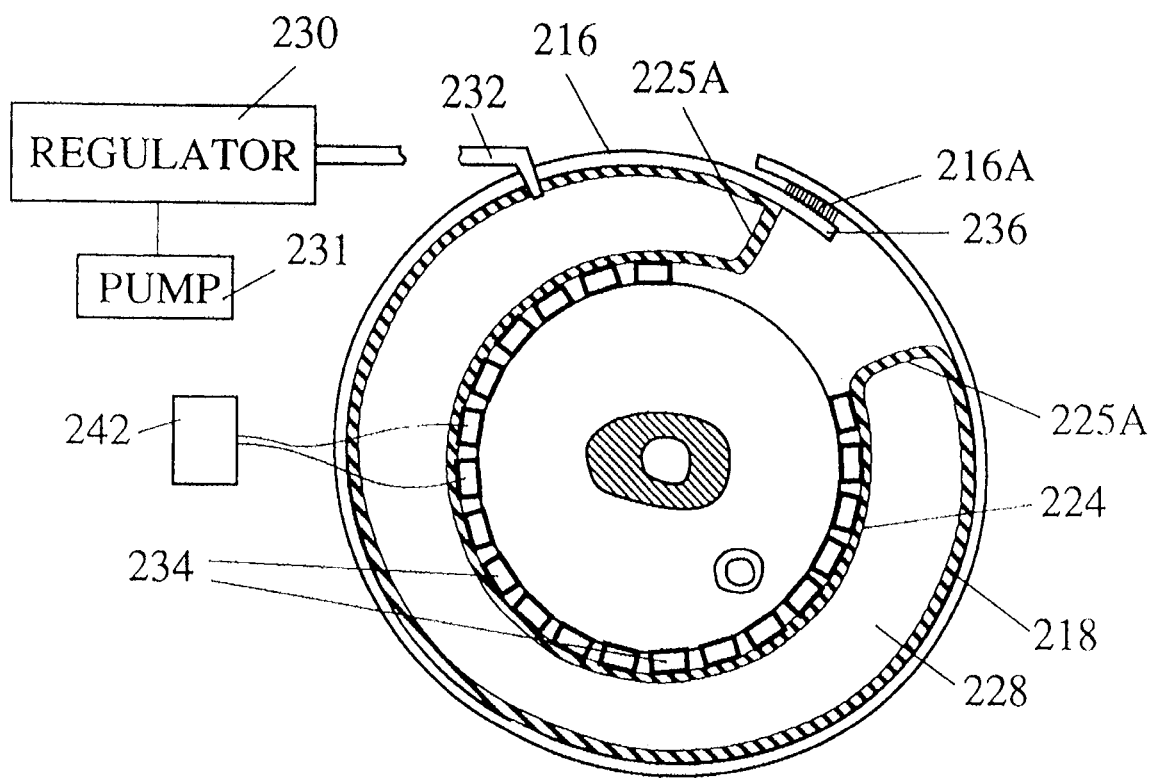
FIG. 26 is a sectional view of the device of FIG. 25.

Another embodiment of the present invention in which deformation can be applied from the exterior of a tissue body is shown in FIGS. 25 and 26. In FIG. 25, a limb of a human, such as an arm indicated at 210 is shown. The underlying tissue is indicated at 212 below the skin surface. Blood vessels are adjacent the skin, as is normal. The limb 10 is encircled with a cuff-like assembly 214, which can be fastened in place, and which is made to include inflatable chambers. The cuff assembly includes an outer wrap 216, as shown, which completely covers the outer surface 218 as shown in FIG. 26 of an inner inflatable chamber 228. Alternatively, wrap 216 could be a series of spaced straps that encompass the periphery of the chamber outer surface 218. As shown in FIGS. 25 and 26, the chamber 28 has end walls 220 and 222, which define, in conjunction with an inner wall 224 and an outer air-tight wall 226, which is sealed to inner wall 224 at its edges 225A and 225B, the interior chamber 228 that can be filled with a suitable pressurized fluid such as air, provided through an adjustable regulator 230 from a pressure source 31 through a connecting line 232. The inner wall 224 is made of a suitable radial force resisting material to which individual pressure sensors indicated at 234 can be adhered. The wall 224 can be suitable plastic (or a thin wall steel band) that is rigid enough to resist forces exerted by a vessel or muscle through the skin surface on the pressure sensors, and will reduce in circumference enough to be forced against the skin from pressure in chamber 228, while generally conforming to the overall curved shape of the limb. The wrap 216 is sufficiently strong to resist outward forces as chamber 228 is pressurized. The pressure sensors 234 are designed to sense pressure in localized areas, and as shown the array of pressure sensors extends substantially around the limb, except for the place where a longitudinal gap 236 (FIG. 26) is provided between the edges 225A and 225B. The gap permits the wall 224 to reduce in circumferential size as it is forced inwardly under pressure in the chamber 228.

The overwrap 216 can be formed of a suitable non-stretchable material if desired and fastened together where the overwrap overlaps, which is that region 216A, with suitable fasteners such as hook-and-loop fasteners sold under the trademark VELCRO, or any other suitable fasteners.

The pressure sensors 234 can be of any desired design, such as small sensors that have deflecting diaphragms with strain gauges on the diaphragms, or capacitive sensors that are miniature in size. These sensors are quite sensitive to determining changes in pressure. For example, one can use sensors such as those incorporated into a Tekscan Industrial Sensing System (for pressure distribution measurement) available from Tekscan, Inc. of Boston, Mass. These sensors are grid-based sensors having a 44 by 44 grid and available in different spatial resolution (e.g., 0.050", 0.075", 0.100") and different sensitivities.

The sensors can be arranged in an array comprising rows along the length or longitudinal axis of the cuff as shown in FIG. 25 at 240. Each of the sensors is individually instrumented, to provide signals to suitable signal conditioning equipment 242, and then each pressure signal can be provided to a diagnostic computer 243. By having individual channels for sensing the individual pressures at each of the sensors 234, a representation of the change in the amount of blood pressure in vessels under the cuff can be determined. The sequence of pressure sensed in each row of sensors extending along a blood vessel will indicate a blood pressure propagation wave, the amplitude of the wave, the timing or frequency of the succeeding waves, all their temporal and spatial features and changes that occur at different loadings on wall 224.

As shown in my co-pending patent application Ser. No. 07/823,155, the pattern of the stresses detected by the sensors of the array can be related to the strain in the underlying tissue, its structure and mechanical properties. By increasing the pressure in the interior chamber 228 (by adjusting the regulator 230 so that the pressure in the chamber 228 will change) the force of wall 224 against the skin also will change, allowing one to obtain such stress and strain information, and evaluate anatomical structure and viscoelastic properties of underlying tissues.

The array of pressure sensors can be selected in size as desired. The length of the array extending along the longitudinal axis of the wrist may be five to ten centimeters and may include about five sensors extending along the longitudinal axis of the wrist and ten to twelve sensors extending about a periphery of the wrist. Of course, the number of sensors used depends upon the size of each sensor (not all sensors need be the same size), the condition being evaluated (e.g., blood pressure, muscle elasticity), and the preference of the investigator.

Figure 27:
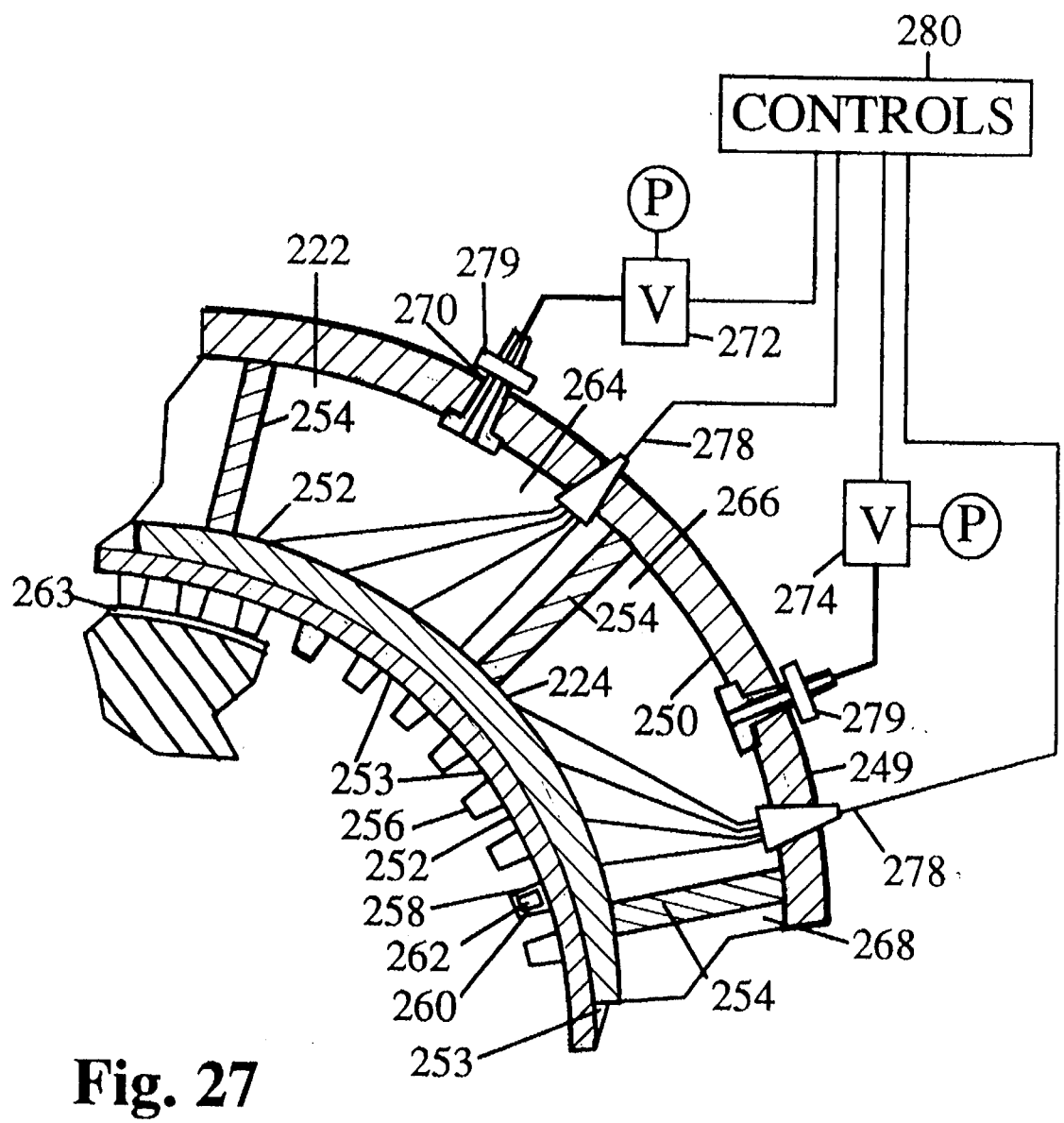
FIG. 27 is an enlarged fragmentary sectional view of a modified form of the invention, illustrating pressure sensors mounted on the interior thereof.

In FIG. 27, a modified form of the invention is shown, and in this case a cuff 249 has a pressure bag or container and an outer wall 250 joined to an inner wall 252 with a suitable number of longitudinal dividers 254. End walls at the opposite ends of the chamber are sealed so that the chamber of the cuff holds fluid under pressure, as previously explained. The inner wall 252 of the chamber bears against a segmented wall 253, formed much like longitudinal strips extending along the length of the cuff. The wall segments 253 each carry a plurality of pressure sensors 256 thereon. These pressure sensors 256 can be adhered to the wall 253, and may include deflecting members 258, supported on a rim-type edge of a housing 260 that defines an interior cavity 262. The deflecting member 258 deflects and acts as a diaphragm when subjected to pressure against the skin indicated at 263 surrounded by the cuff.

Longitudinal members 254 divide the cuff into a plurality of individual longitudinally-extending chambers 264, 266 and 268 as shown, and each of these chambers is above one of the segments of wall 253. The chambers can each have a suitable inlet valve 270 that is controlled through an individual fluid pressure valve 272 and 274, as shown, so that the individual pressures in the chambers 264, 266 and 268 can be changed. This will permit one to vary the internal pressure and thus the force exerted on the skin along a wall segment 253, at selected positions around the circumference of the cuff, for obtaining different types of imaging from the pressures or forces sensed by the individual pressure sensors 256.

Each of the pressure sensors 256 has wires or leads 278 to carry signals from the deflecting diaphragm. These leads 278 extend outwardly through the outer wall 250 through a sealed connection 279 to prevent pressure leaks and are connected to additional suitable leads leading to controls indicated at 280. The controls 280 can be used for controlling the valves 272 and 274, and for recording, using, and maintaining the various pressure signals that are obtained from each of the individual pressure sensors.

The cuff is attached easily and can be used much like an ordinary blood pressure measuring cuff (e.g. sphygmomanometer cuff). The cuff carries individual pressure sensors for sensing pressures on localized areas of the skin (that is surrounded by the cuff) to obtain blood pressure propagation wave pattern having temporal and spatial characteristics. This pattern can be analyzed to indicate information about the circulating system of the patient being analyzed.

Figure 28:
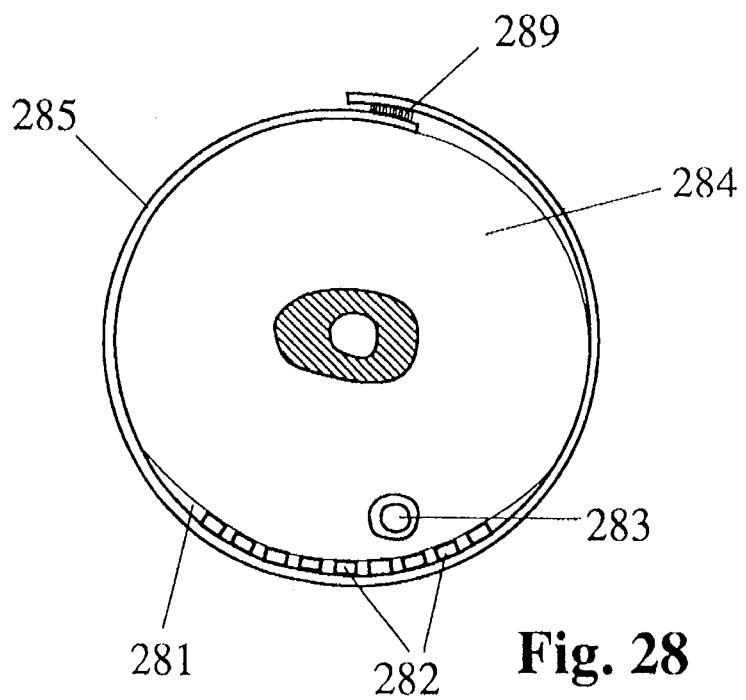
FIG. 28 is a sectional view of a limb with a pad type pressure array held in place against a limb.

In FIG. 28, another modified form of the invention is illustrated. In this form, an array of pressure sensors are mounted on an individual pad, and held in place with a suitable overwrap. The pad indicated at 281 can have a plurality of individual sensors 282 thereon, which are positioned adjacent the blood vessel 283 on an arm 284. The pad 281 can be constructed similarly to that shown in the previous figures, and in this case if desired the pad can be made in a rigid shell that conforms to the shape of the arm, and the band 285 can be used for applying differing pressures to the pad. Also, an inflatable bag can be placed between the band 285 and the pad 281 so that the bag can be inflated to exert different pressures on the pad. The band 285 is non-stretchable to react the forces and can be held in place at an overlapped portion 89 of the cuff through the use of suitable fasteners.

The blood flowing in the vessel 283 will create changes in pressure patterns which can be used to obtain an objective evaluation of circulatory conditions.

In general, all forms of the invention allow one to register temporal and spatial orientations of blood pressure flow under differing loading to obtain a multiparameter description of the state of the circulatory system. Such data accumulated over time in parallel together with diagnostic information provided by experts on pulse diagnostics (and confirmed by conventional methods) are used to form the computerized analyzation system for correlative evaluation of the particular bodily condition present in the patient.

The cuff, as shown, also can be used for determining pressure pattern changes due to other responses below the skin, such as determining functional state and physiological responses of the muscles in investigated area of limb.

The cuff can be much shorter than shown. The cuff includes a desired means for permitting it to be fastened in place surrounding a portion of a limb for analyzing the mechanical properties and structure of tissue under the cuff by measuring pressure pattern changes while regulating and changing the pressure or force exerted on the skin. Individual sections of the cuff can be controlled by providing multiple individual inflatable chambers instead of a single inflatable chamber to permit non-uniform forces to be exerted on the limb.

The structure provides the ability to quickly apply the pressure sensing array and then vary the pressure conveniently. The ease of use of the invention leads to wide adaptability. Individual pressure sensors permit an array of sensors to analyze conditions in localized areas of the tissue surrounded by the cuff.

Figure 29:
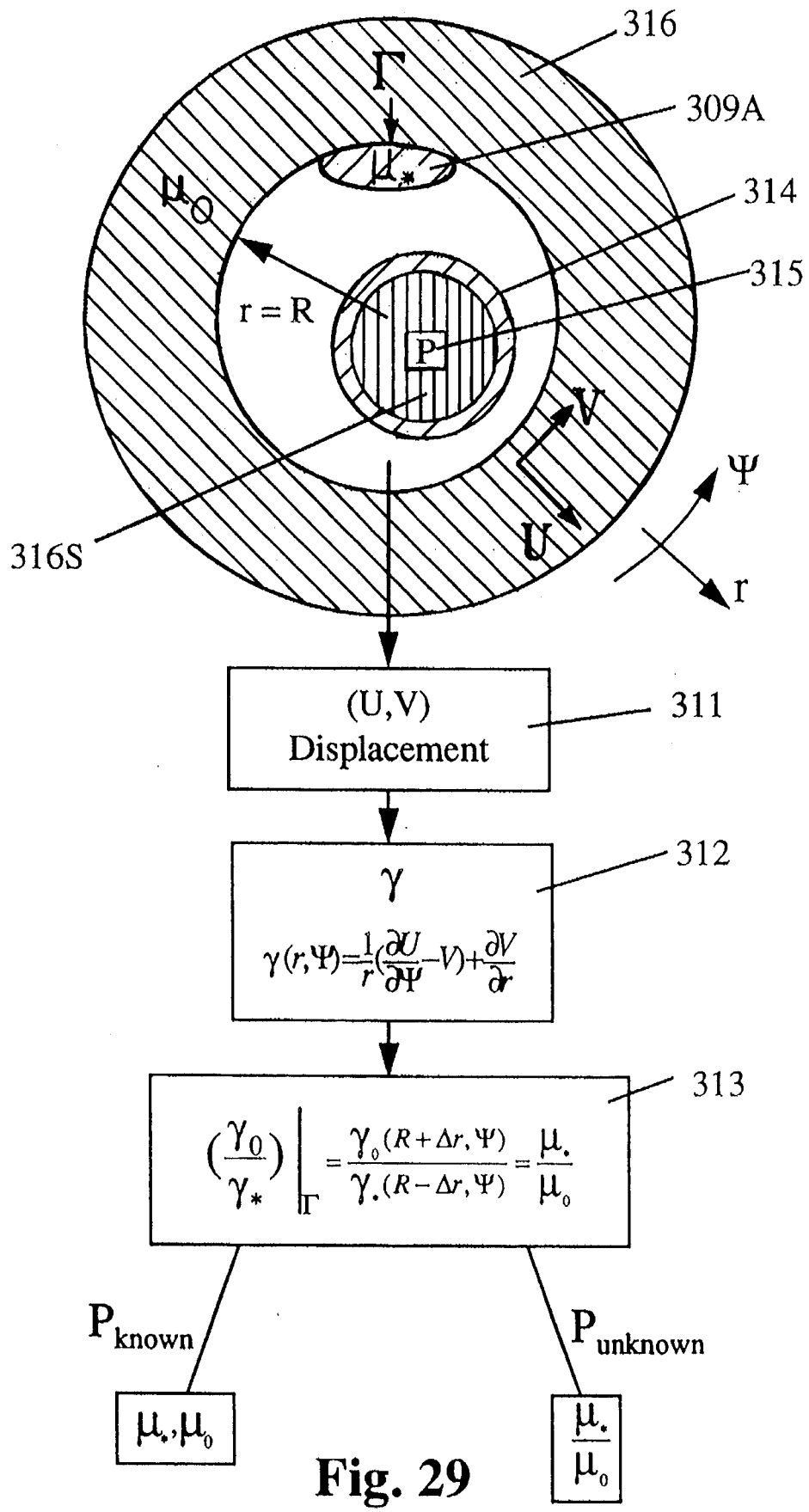
FIG. 29 is a schematic representation of a cross-sectional view of a blood vessel with a plaque and including a box diagram for determining the ratio of shear moduli of the plaque and vessel based on the calculating shear component of strain on the boundary between the plaque and the vessel.

The variations in deformation needed for analyzing tissue for areas of differing elasticity may be the result of blood pressure changes in a blood vessel such as shown in FIG. 29. A phased array ultrasonic scanner can be carried on the interior of an endovascular probe and provide imaging of the lumen wall during blood pressure variations.

Several embodiments of the present invention have been presented thus far for facilitating the manipulation of tissue in order to enhance analyzation of images of the internal structure and ultimately for calculating elastic moduli of various regions within the tissue. FIG. 29 illustrates one method of evaluating mechanical properties of the internal structure of a tissue body. The method is based on evaluating the strain on the individual tissue particles before and during compression of the tissue (compression by blood pressure cycling) by observing differences in images of the tissue obtained before and during tissue compression. FIG. 29 presents the method as applied to a bodily conduit wherein a radial coordinate system is used for tracking movement of the tissue particles of the tissue body.

FIG. 29 shows a two dimensional (i.e., cross-sectional) image of a vessel 316 having a plaque 309A formed on a wall of the vessel. A scanner 316S is schematically illustrated as being located in a catheter 314 positioned in the lumen of the vessel 316. The symbol Γ designates a boundary between the plaque 309A, which has a shear modulus designated as $\mu_*$, and the vessel tissue 316, which has a shear modulus designated by $\mu_o$. The following description in connection with FIG. 25 is intended to be merely illustrative of the principles involved in evaluating the elasticity of internal structures of a tissue body and is discussed as a simplified two-dimensional approach. In a general case to evaluate elasticity of internal structures it is necessary to make a number of cross-section images of tissue at different longitudinal positions along the vessel, then make a three-dimensional reconstruction and compare the strains of the three-dimensionally reconstructed structures under various loading conditions using the mathematics described above.

As illustrated by the box diagram flow chart in FIG. 29, a method of determining the relative shear modulus between the plaque 309A and the vessel 316 can be performed in the following manner. First, a scanner 316S is used to produce a two-dimensional image of a cross-section of the vessel wall and plaque, such as that cross-section shown in FIG. 29. By analyzing the image, a plurality of tissue particles are identified in the image of the vessel and plaque which have a horizontal and a vertical dimension, or any two dimensions which are perpendicular to each other.

Because the vessel 316 has blood flowing through its lumen under pressure as a result of cardiac pulsation, the wall of the vessel 316 will expand and contract in accordance with the rise and lowering of the blood pressure through the vessel. In this method, the first image just discussed would be obtained when the vessel wall is contracted i.e., when the blood pressure is at its lowest in a cardiac pulsation cycle.

Next, another image of the cross-section of the vessel 316 is obtained when the vessel wall is expanded, i.e., at the peak of the blood pressure cardiac pulsation cycle. By comparing the two images of the vessel wall at the differing blood pressure levels, one can determine a local displacement for each tissue particle in the image of the vessel and plaque. The components of displacement are designated by the vector directions u and v as shown in FIG. 29.

Because the vessel is circular as seen in a cross-sectional view, the components of displacement u,v can be expressed as components of displacement in a radial direction (r) and in azimuthal direction ($\psi$).

Accordingly, the method includes determining the components of displacement for each tissue particle in the vessel and plaque and relating the displacements in terms of the components r and $\psi$. Next, a shear component of the deformation tensor is obtained by relating the displacement in the u,v directions to the r, $\psi$ directions as shown by the equation in box 312 in FIG. 29. This shear component of the strain or deformation tensor is represented by the symbol $\gamma$ as a function of a point (r, $\psi$). This shear component $\gamma$ can be obtained for each tissue particle in the vessel and plaque, however, obtaining the shear component for each tissue particle is not necessary. Instead, only the shear components on either side of the boundary Γ are of interest. Accordingly, we can restrict an analysis of the shear component of the tissue particles to a comparison of the shear component of a tissue particle of the vessel 316 at the boundary Γ to the shear component of a tissue particle of the plaque 309A at the boundary Γ which is adjacent to the identified vessel tissue particle. For example, one could determine the shear component for a tissue particle in the vessel 316 at the boundary Γ using the equation in box 312 where the shear component for that tissue particle is a function of (R+Δr, $\psi$). Similarly, a shear component of a tissue particle of the plaque 309A at the boundary Γ, which is adjacent the vessel tissue particle at (R+Δr, $\psi$) can be determined through the equation in box 312 and the shear component of this plaque tissue particle is calculated for a point (R−Δr, $\psi$). By relating the shear component $\gamma$ (R+Δr, $\psi$) to the shear component $\gamma$ (R−Δr, $\psi$) in terms of a ratio as shown in box 313, one obtains a value which corresponds to a ratio ($\mu_*/\mu_o$) of the shear modulus ($\mu^*$) relative to the shear modulus ($\mu_o$). This ratio ($\mu_*/\mu_o$) indicates the relative shear modulus between the plaque 309 and the vessel 316.

If the internal pressure P within the lumen of the vessel 316 is measured by a pressure sensor 315 carried in catheter 314 as shown in FIG. 29, the exact values of $\mu_*$ and $\mu_o$ can be obtained by solving the general equations for non-compressible media discussed and illustrated previously. However, if the internal pressure P is unknown, the relative modulus of elasticity of the vessel and the plaque can only be evaluated in terms of a numerical value of the ratio ($\mu_*/\mu_o$) that was determined by comparing the shear component of adjacent tissue particles on opposite sides of the boundary Γ as represented by the equations in box 313.

Combined systems can be utilized including pressure sensors that determine surface conditions, and scanners such as MRI, x-ray or ultrasound scanners which provide information about deformations and corresponding strain profiles of internal structures under various loading conditions. The pressure sensing arrays can indicate stress profiles on the surface and the conventional scanners give information about the changes in geometry of any internal structures and corresponding strain pattern. Thus the calculation of elasticities of internal tissues will be performed with higher resolution and, additionally, regions of interest in the images produced by an imaging device can be characterized in the terms of relative elasticity or hardness. This will increase diagnostic capability of the existing imaging methods in tumor diagnostics.

Figure 30:
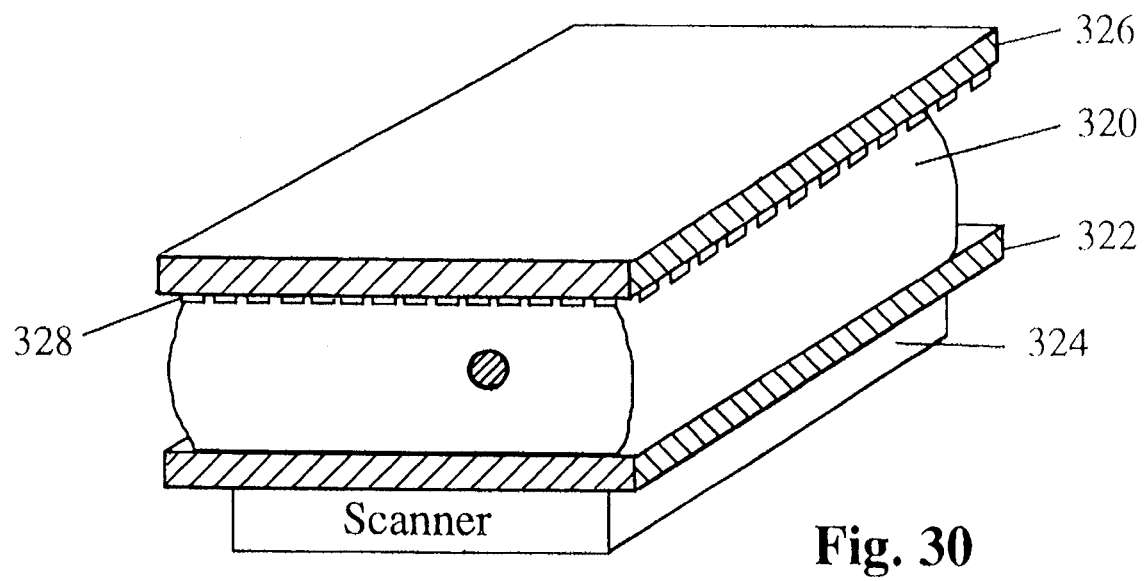
FIG. 30 is a schematic representation of a combined system deformation device in which a pressure sensor array located on top of the tissue and an ultrasonic scanner is located below the tissue on a side opposite from the pressure sensor array.
Figure 31:
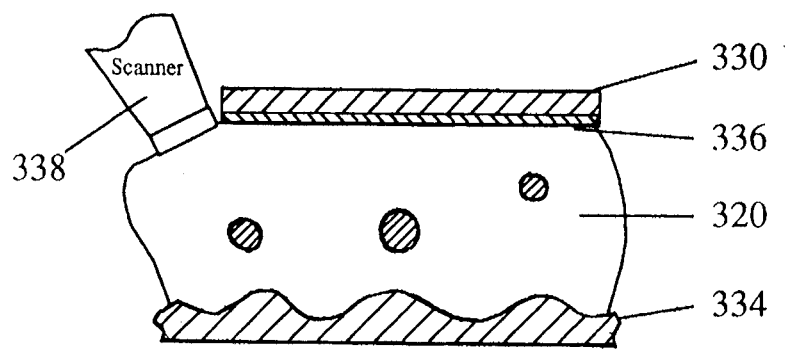
FIG. 31 is a cross-sectional view schematically depicting a pressure sensor array positioned on top of a tissue block with an ultrasonic scanner is disposed on a side of the tissue with the tissue supported by an irregular surface.

In FIGS. 30 and 31, a combined system is illustrated. In FIG. 30, a mass of tissue indicated at 320 is supported on a suitable support 322, which has a scanner 324 mounted thereon on a bottom side, or from an opposite side from the tissue. The tissue is compressed with a support plate 326 that has a plurality of individual pressure sensors in an array indicated generally at 328. The pressure array at the surface as shown provides a pressure distribution depending on the structure and elasticities of internal tissues. The pressure sensing array provides the data for structure and elasticity evaluation as it is described in the co-pending application Ser. No. 07/823,155. The scanner 324 (which can be an ultrasound scanner, a magnetic resonance imager, or a CAT scanner) identifies the geometry of the internal tissues and can be used for detection of boundaries between tissue of different elasticity and obtaining the strain pattern so that the inverse problem can be solved easier.

FIG. 31 is a modification of the device in FIG. 30 and includes a pressure plate 330 acting on tissue 320, which is supported on a support plate 334 in the model shown, which is simulating soft tissue to which access can be provided from one side and on the opposite side supported by skeletal elements, such as the bone structure. In this instance, the support plate can have an irregular surface, representing a bony or skeletal structure underlying investigated soft tissues. This results in a different pressure profile being measured from the pressure sensors 336 (on the bottom of the plate 330). A scanner 338, which is positioned alongside the tissue and angled relative to the tissue, can be used for imaging the changes in the internal geometry of the tissue 320 under different loading conditions to obtain the internal strain profiles. Again, the scanner can be of any desired form, but by analyzing both the stress pattern on the pressure sensors 336 and the internal strain patterns from the scanner, the condition of any inclusion in the tissue can be determined. This information includes the elasticity information and can include positional and dimensional information about the inclusion.

Figure 32:
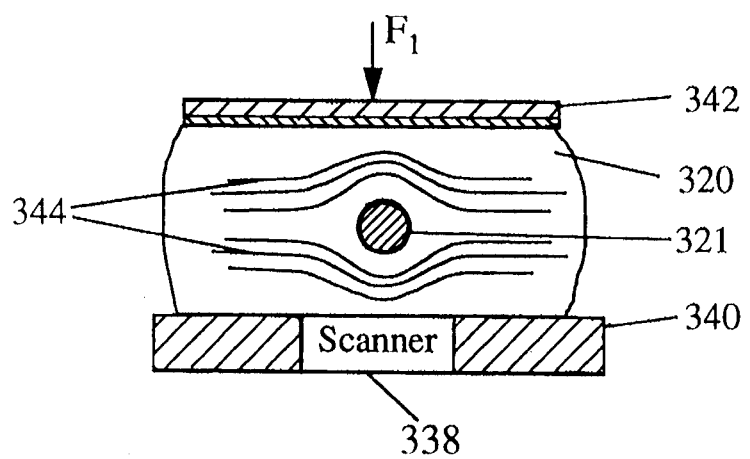
FIG. 32 is a cross-sectional view schematically depicting the strain profiles resulting from compression of a tissue block with a tumor therein and the effect on the tissue layers.

In FIG. 32, a representation of strain pattern or other profile in a compressed tissue 320 is shown with an inclusion 321 (e.g., cross section of bone, tumor, or fibrous tissue) therein. The plate 342 can be moved in vertical direction as indicated by the arrow $F_1$. The tissue 320 is supported on a suitable support 340. The strain profiles of tissue are depicted (indicated at 344) internal of the tissue 320 and above, below, or in both sides of the inclusion 321. These strain profiles would appear on the image produced by a scanner 338 and relative deformation of this lines after loading the tissue will depend on the mechanical structure of tissue.

If the inclusion has a complex structure, i.e., has a variety of tissue hardness or has a complex shape which is not uniform, then the known displacements of the nearest layers or the other structures give the possibility to determine more exactly the properties of this complex inclusion.

FIGS. 33, 34A, 34B and 34C illustrate that analysis of the changes in dimension of portions of tissue in vector directions can be used for determining the presence of a tumor and its mechanical properties. This technique can be applied even to dimensional changes that are on the surface remote from the inclusion.

Figure 33:
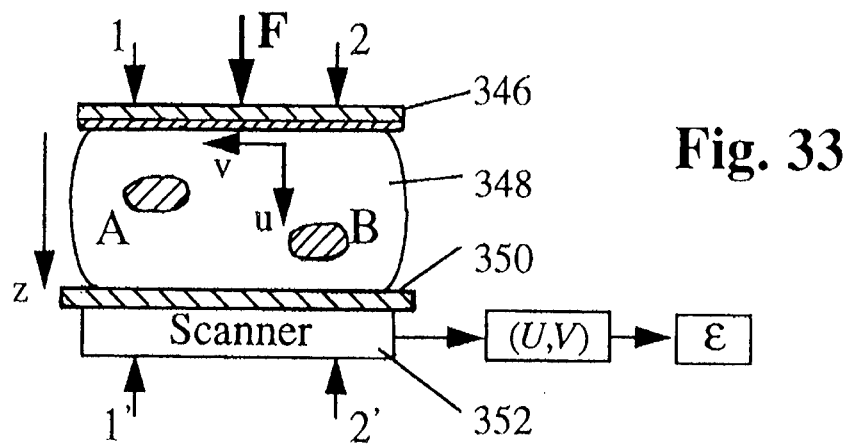
FIG. 33 is a schematic representation and cross-section depicting a block of tissue with two tumors therein being compressed with a scanner adjacent the tissue for monitoring tissue displacement.

In FIG. 33, a plate 346 is positioned to compress tissue 348 against a support plate 350. A scanner 352 is positioned on the opposite side of the support plate from the tissue.

The following description is again intended to illustrate the principles involved in a simplified two-dimensional as with the discussions about FIG. 29 to evaluate the relative deformation it is necessary to take several images of tissue cross-sections and make a three-dimensional reconstruction to compare the deformation of the tissue along the third dimension (length) of the occlusion, using the mathematical analysis described previously.

Figure 34A:
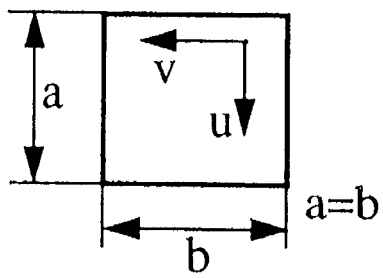
FIG. 34A is a schematic representation of a portion of tissue before compression with certain strain parameters illustrated.
Figure 34B:
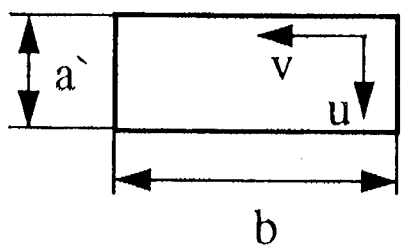
FIG. 34B is a schematic representation of a portion of tissue during compression with certain strain parameters illustrated.

When force is applied, as indicated by the arrow (F) on the plate 346, individual particles or portions of tissue will change in any two dimensional plane. The components of displacement in such plane denoted as u and v. FIG. 34A illustrates a particle of uncompressed tissue with dimensions a and b that are equal. Under a compressive load (as shown by the arrows (R) in FIG. 34B), the particle will compress in the u (e.g. vertical) to dimension $a_1$ and expand in the v direction (e.g. horizontal) to dimension $b_1$. The actual volume of the inclusion does not change, but the dimensions of the particles in the vector directions (u,v) shift. The changes in the shape of a given tissue particle before and during compression can be determined through comparing images (obtained by a scanner) of the internal structure of the tissue before and during compression. Monitoring the relative changes of tissue particle dimensions can be accomplished through various methods e.g. by speckle tracking technique in the case of ultrasonic imaging. Known speckle tracking techniques are discussed in the following publications: J. Meunier and M. Bertrand, *Ultrasonic Speckle Motion Inherent to Tissue Motion: Theory and Simulation*, Proceedings of the 1989 IEEE Ultrasonics Symposium 0090- 5607-89, pp. 865 868 (1989); and M. Bertrand, J. Meunier, M. Doucent and G. Ferland, *Ultrasonic Biomechanical Strain Gauge Based on Speckle Tracking*, Proceedings of the 1989 IEEE Ultrasonics Symposium 0090- 5607-89, pp. 859 864 (1989).

In the case of MRI, the detection of strain patterns in the compressed tissue can be evaluated by so-called "tagged imaging". See e.g. E. A. Zerhouni et al., *Human Heart Tagging With MR Imaging A Method for Noninvasive Assessment of Myocardial Motion*, Radiology Vol. 169, 169 172 (1988) and J. G. Pipe et al., *Method for Measuring Three-Dimensional Motion With Tagged MR Imaging*, Radiology Vol. 181, 591 595 (1991). The imaging analysis of the deformation of the tissue particle can provide a strain characteristic denoted $\epsilon$ and equal to the ratio of the ($a_1$) (vertical) and ($b_1$) (horizontal) dimension.

Figure 34C:
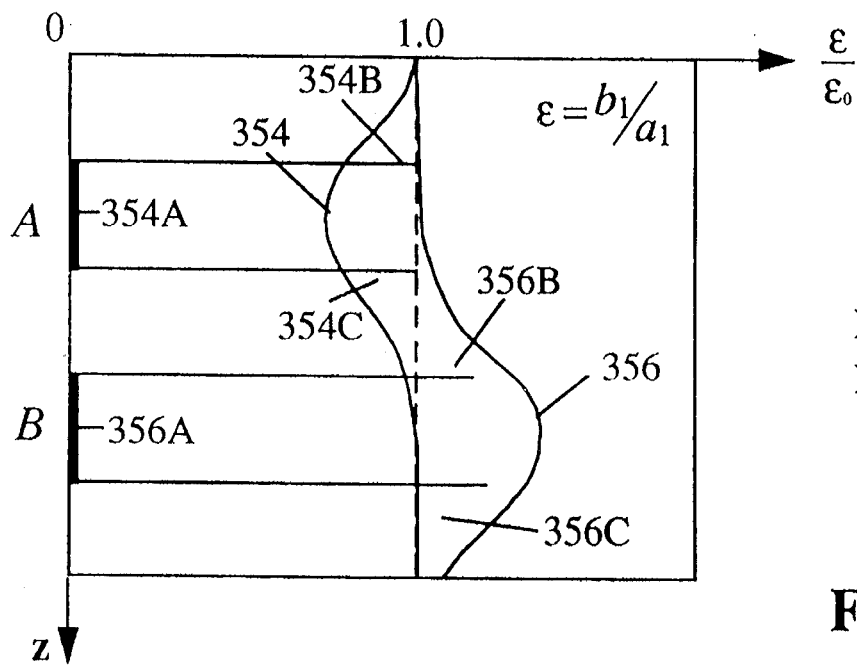
FIG. 34C is a diagram illustrating a profile of a strain ratio along a vertical Z axis to illustrate relative hardness of tumors like that shown in FIG. 33.

The strain characteristic $\epsilon = b_1/a_1$, which can be obtained for each tissue particle based on experimental displacements (i.e., the change in tissue particle dimensions) by the just described image analysis technique (represented by $(u,v)^{exp}$ in FIG. 23). FIG. 34C illustrates a ratio of strain characteristic of an inclusion within the tissue ($\epsilon$) to the strain characteristic of normal tissue ($\epsilon_o$) as shown in FIG. 33 (during compression) as a function of distance (Z) from the top array 346. The strain ratio ($\epsilon/\epsilon_o$) is measured along the horizontal axis and position along the Z axis is measured in the tissue corresponding to a vertical line extending from the top of the tissue through inclusion A and to the bottom of tissue 248 (See FIG. 33). Along axis 1 1 and at a region corresponding to the position of inclusion A (indicated by 354A) within the tissue, the strain profile shows that the strain characteristic of tissue particles of the inclusion ($\epsilon_A$) is less than strain characteristic of tissue particles of normal tissue ($\epsilon_o$), as indicated by the curve 354 peaking to the left. Because the strain characteristic $\epsilon$ is related to the modulus of elasticity, this relationship between the strain characteristics $\epsilon_A$ and $\epsilon_o$ means that inclusion A has modulus of elasticity ($E_A$) higher than that of normal tissue ($E_o$), and therefore inclusion A must be harder than normal tissue. Of course, a similar relationship exists between the modulus of elasticity and strain characteristic for inclusion B except that the strain characteristic for inclusion B ($\epsilon_B$) is more than the strain characteristic of normal tissue ($\epsilon_o$) as shown by line 356 for the area indicated by 356A (corresponding to the position of inclusion B along the line 2 2 in FIG. 33). This indicates that inclusion B is softer than the surrounding normal tissue.

Moreover, the projection shows that in the region adjacent the perimeter of the inclusion, the strain of surrounding tissue is affected so that the behavior of the tissue near the tumor is affected by the presence of the tumor. The strain characteristic for these regions adjacent the perimeter of the inclusion A are shown at 354B and 354C and similar regions are shown for inclusion B at 356B and 356C. Accordingly, to identify the presence and approximate location of an inclusion within a tissue portion, one can compare the strain characteristic between adjacent tissue particles to identify regions within the tissue portion that have tissue particles with a strain characteristic significantly different than the strain characteristic of tissue particles throughout the remaining tissue portion. The regions 354B and 354C and regions 356B and 356C of FIG. 34C correspond to transitions between tissue particles of an inclusion and tissue particles of surrounding normal tissue. The transition approximately defines a region of tissue particles having a strain characteristic (e.g. the strain characteristic $\epsilon_A$ for tissue particles of inclusion A) that is significantly different from the strain characteristics of the tissue particles for the surrounding remainder of the tissue portion (e.g. the strain characteristic $\epsilon_o$ for the tissue particles of normal tissue).

In addition to merely identifying a region of different elasticity within the tissue portion, one can determine the relative moduli of elasticity between the region of different tissue elasticity (e.g. tumor) and the surrounding tissue. This can be achieved by calculating a ratio of the strain characteristic value of the different elasticity region to the strain characteristic value of surrounding tissue. This ratio is proportional to a ratio of the modulus of elasticity of the inclusion (i.e., different elasticity region) to the modulus of elasticity of the surrounding tissue. Accordingly, by relating a strain characteristic value to a modulus of elasticity, one can determine in order of magnitude, the relative difference (greater or lesser) between the modulus of elasticity of an inclusion (e.g. $E_A$ or $E_B$) and the modulus of elasticity of the surrounding tissue ($E_o$).

This information based on monitoring strain variations aids in determining the relative tissue elasticity through imaging by being able to define the changes in dimensions of portions of tissue by tracking points visible in the image projected. Other types of analysis can be carried out to determine elasticity by establishing grids of points as is done by tagged MR imaging technique and analyzing a number of points across the plane of the tissue. The original markers inside the living tissue also can be used.

This method of identifying a region of different elasticity within a tissue portion by determining strain characteristic values of compressed tissue particles is not confined in its application to the configuration shown in FIG. 33. For example, the scanner need not be positioned on a top or bottom of a plate supporting the tissue. The method also can be applied in the configurations like that shown in FIG. 31 (or FIGS. 38A and 38B) in which the scanner for producing images of the tissue is positioned on a side of the tissue at an angle to the axis of compression of the tissue. Images produced by this "side" scanning are equally suitable for analysis to determine the displacements of tissue particles in terms of "horizontal" and "vertical" dimensions (i.e., the u,v directions). Of course, if necessary, the orientation of the u,v vectors can be rotated to make the analysis more convenient.

At present, this method is illustrated in FIG. 33 for analyzing a two-dimensional image of the internal structure of the tissue. Of course, the scanner in FIG. 33, as well as the scanner shown in FIGS. 29–39, can be moved in the third dimension as desired so that the method can be applied to as many two-dimensional images of the tissue along the third dimension as is necessary to make a three-dimensional reconstruction, determine the boundary of the inclusion in three dimensions under various loading conditions and then solve general equations for the linear theory of elasticity and evaluate elastic moduli of inclusion and surrounding tissues. Moreover, this method can be applied to any of the configurations discussed in which a scanner is used to image the strain profiles in the internal structure of the tissue to determine elasticity within the tissue, i.e., it can be used in conjunction with FIGS. 29–32 and those to be discussed in FIGS. 35–38 and 41–42.

The method of evaluating inclusions as illustrated in FIGS. 33, and 34A–34C is advantageous where it is particularly difficult (in the case of very complex inclusion-having a very non-uniform surface) to determine the exact boundary of the inclusion. The method conveniently yields information sufficient to determine the presence, location, approximate boundary, and relative modulus of elasticity of a region of tissue having different elasticity than the surrounding tissue.

Figure 35:
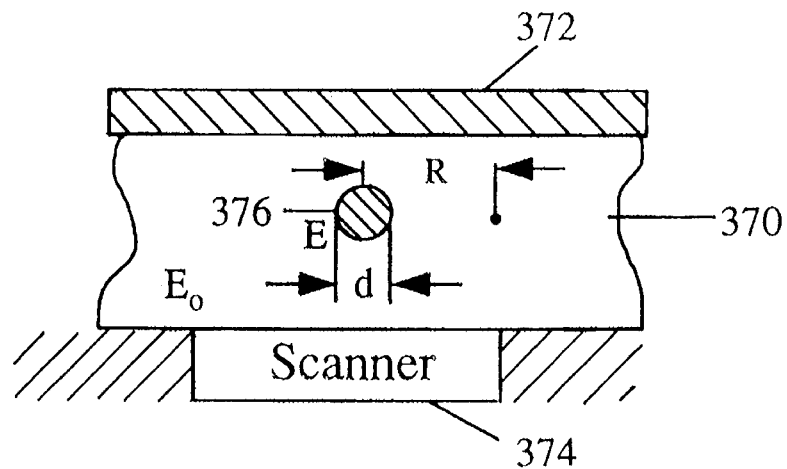
FIG. 35 is a schematic representation and cross-section of a tissue block with a compressional plate thereon and a scanner device located therebelow.
Figure 36:
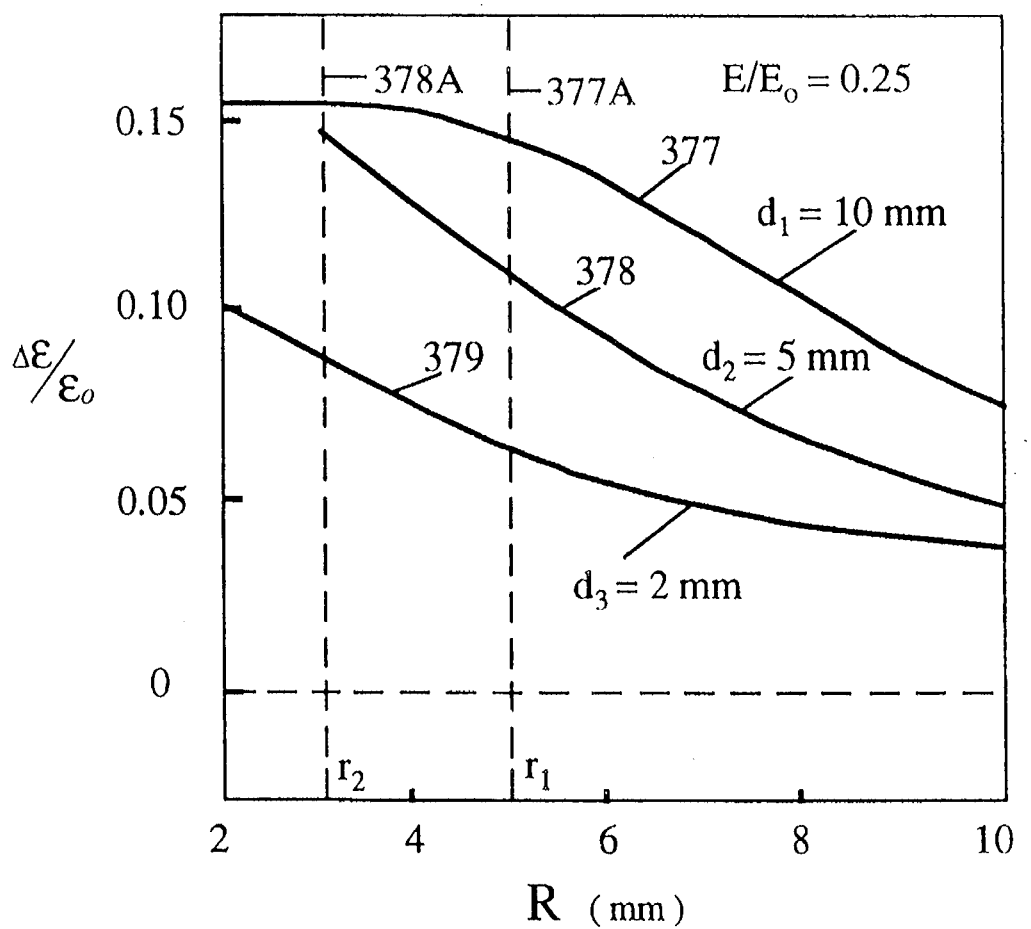
FIG. 36 is a graphical representation of the deformation of tissue surrounding the tumor relative to normal tissue located away from the tumor as a function of the distance from the center of the tumor.

FIGS. 35 and 36 illustrate the behavior of tissue near an inclusion when imaging and identifying boundaries of internal structures of the tissue and the ability to find a lump or tumor upon compression because of distortion or disturbances of tissue adjacent to the tumor. This illustration is based on the use of data which can be obtained by any technique enabling one to detect displacements of a given point of internal tissue, such as speckle tracking in the case of ultrasonic imaging or "tagged imaging" using MRI as noted in the literature mentioned above.

FIG. 35 shows a portion of tissue 370 that is compressed with plate 372 with a scanner 374 provided for imaging the tissue. An inclusion 376 has dimensions as shown, and a modulus of elasticity E, with the surrounding tissue having the modulus of elasticity $E_o$. The quantity R illustrated in FIG. 35 is the distance from the center of the inclusion. In FIG. 36, the ratio of moduli of elasticity between the inclusion and surrounding tissue is taken as 0.25 ($E/E_o = 0.25$). The relative deformation is represented by the ratio $(\Delta\epsilon/\epsilon_o)$—which is the change in strain ($\Delta\epsilon=\epsilon-\epsilon_o$) divided by the strain occurring in normal tissue during compression. The quantity ($\Delta\epsilon/\epsilon_o$) is plotted on the vertical scale, and R is shown on the horizontal scale. The plot 377 illustrates the relationship between the ratio of strain ($\Delta\epsilon/\epsilon_o$) as a function of distance R when the diameter of the inclusion is 10 millimeters. The vertical line 377A shows the boundary of the inclusion, that is $r_1$ (R=5 mm). The plot or curve 378 shows a linear strain/distance relationship except when the inclusion has a diameter of five millimeters (R=2.5 mm). In that case, the vertical line 378A represents the boundary of the inclusion or the outer edge of the inclusion, when R=2.5 mm ($r_2$). The curve or plot 379 corresponds to an inclusion having a diameter of two millimeters. As previously discussed, the ratio of the change of points between those parallel to the direction of compression force and those perpendicular to the direction of compression force (i.e., a, b, respectively in FIGS. 34A and 34B) provides for an indication of the relative modulus of elasticity of the inclusion/surrounding tissue and makes the inclusions visible in an imaging analysis.

This graph illustrates that the presence of a small tumor can be detected by analyzing tissue deformation beyond the edges of the tumor. Again, the graph of FIG. 36 indicates that as the distance increases between the points being tracked and the tumor the observer loses definition of the tumor boundary but yet can get enough information to indicate the presence of some type of an inclusion. This imaging shown in FIG. 35 utilizing the analysis presented in FIG. 36 can be performed in three dimensional form for early detection of very small tumors.

Figure 37:
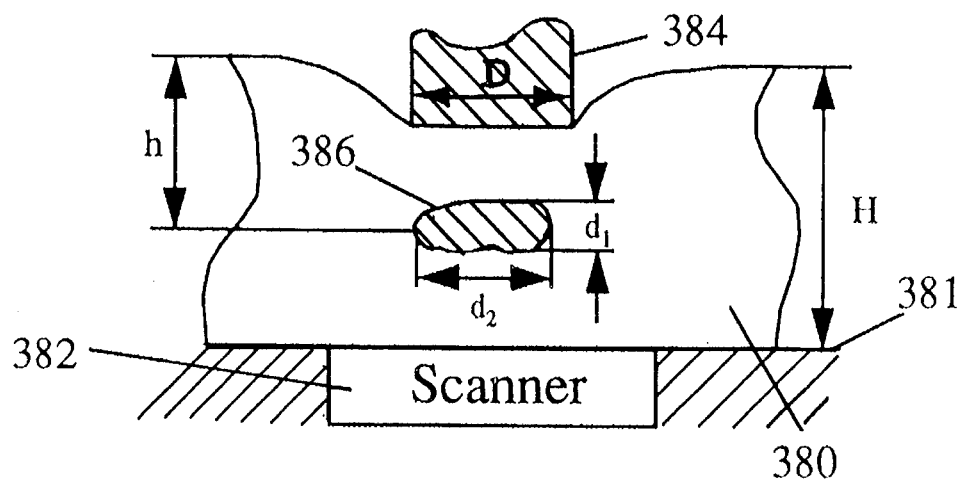
FIG. 37 is schematic representation and cross-section of a tissue block with tumor therein compressed by a piston with a scanner supporting tissue.
Figure 37A:
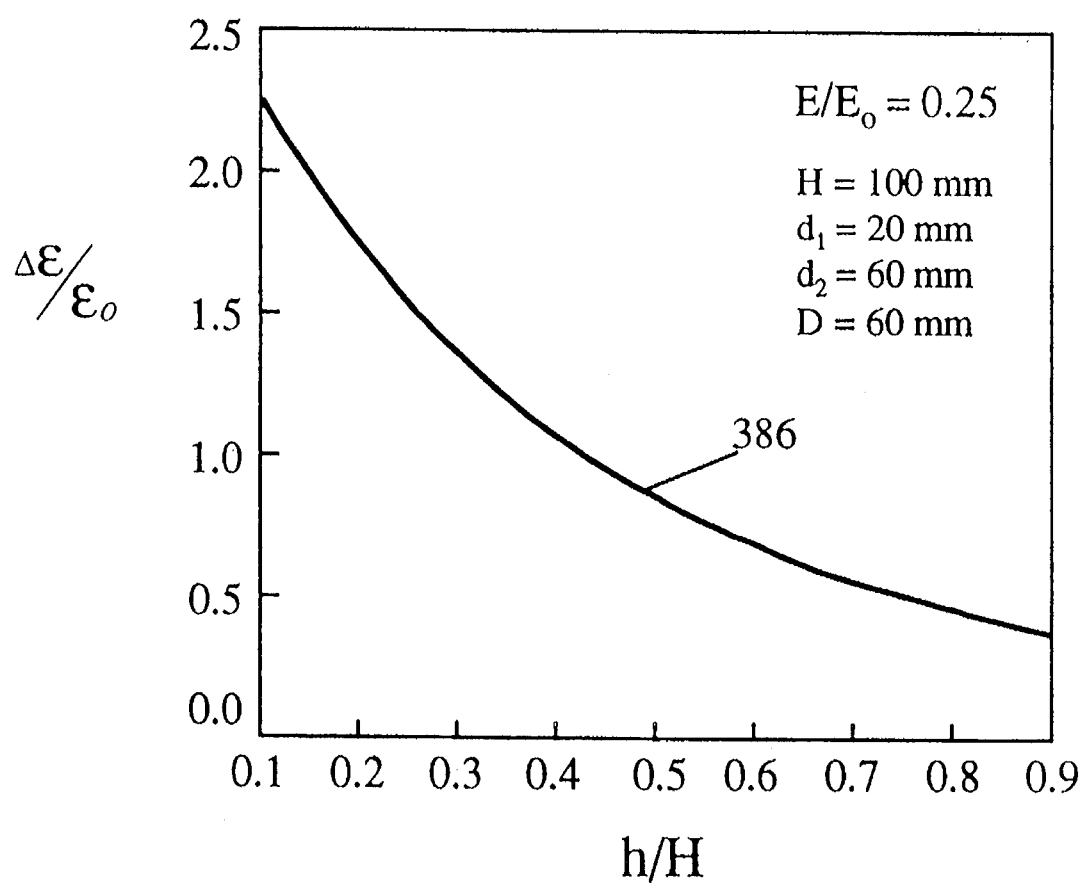
FIG. 37A is a graphical representation of the deformation of tumorous tissue relative to surrounding tissue as a function of the relative distance of the tumor from the upper tissue surface.

FIGS. 37 and 37A illustrate quantitatively the depth sensitivity of relative deformation.

$$\Delta\epsilon/\epsilon_0 = \frac{(\epsilon - \epsilon_o)}{\epsilon_o}$$

In FIG. 37, a tissue mass 380 is supported on a support 381 with a scanner 382 below the support for imaging the internal structure of the tissue 380. A piston or probe 384, which has a diameter D, presses on the outer surface and compresses the tissue above a tumor 386 (or other inclusion). The tumor has a dimension in the Z or vertical direction of $d_1$, and a horizontal or transverse dimension of $d_2$. The tissue has an uncompressed height of H, and the distance from the top of the tissue mass to the center of the tumor in the Z or vertical direction is recorded as h. Example dimensions for the piston, the tumor and H are provided in the graph of FIG. 37A. A ratio of the moduli of elasticity of 0.25 between the tumor and surrounding tissue is assumed.

The graph curve 386 shows the effect that the distance from the probe 384 to the tumor has on the measured relative deformation ($\Delta\epsilon/\epsilon_o$) between the tumor and normal tissue. The ratio of (h/H) is plotted on the horizontal scale and ratio of ($\Delta\epsilon/\epsilon_o$) is plotted on the vertical scale. The curve 386 shows that as the tumor is closer to the probe, the change in strain of the tumor relative to the strain of the surrounding tissue is greater when the distance of the tumor from the piston 384 is less.

It has also been determined that the sensitivity of detecting and imaging an inclusion can be changed by varying the angle of the scanner. Additionally, changing the angle of force applied to the tissue relative to a scanner can produce different results such as increased sensitivity. As shown schematically in FIG. 38A, tissue 390 is supported on a pivoting plate 392, (similar to that shown in FIG. 21) as it is being compressed. Compression on the tissue acting on the tumor 394 while pivot plate 392 is tilted at an angle will cause an image resulting from a scanner 396 that is different than an image resulting from straight compression along the Z or vertical axis. The effect of an angular application of force also is related to (or analogous to) the action as shown in FIG. 38B where compression remains in a vertical plane while the scanner axis is disposed at various angles relative to the compression axis. This can be done by moving the scanner along various locations on the surface of the tissue.

In FIG. 38B, tissue 400 is supported on a support 401 which could be also an internal skeletal structure, and is compressed with a probe or piston 402 along the vertical axis. A scanner indicated at 404 for imaging the internal structure of the tissue is positioned at an angle relative to the vertical axis that is shown as theta ($\Theta$). The scanner has a scanning axis that intersects the tumor 406.

The effect of compression on such a tumor is shown in FIG. 38C where the dotted line representation shows the configuration of the tumor after compression, and the solid line representation shows the tumor prior to compression. The line $A_1$–$B_1$ is the Z axis or the direction of force application (also indicated by the arrows) and the line $A_2$–$B_2$ is the scanning axis. The angle theta ($\Theta$) is the angle between the compression axis and the scanning axis.

FIG. 38D is a graphical representation of this embodiment (where the ratio of the moduli of elasticity $E/E_o$=0.25), in which the strain characteristic $\epsilon$ is plotted on the vertical scale, and the angle ($\epsilon/\pi$) is plotted on the horizontal scale. Line 407 in FIG. 38D illustrates that the strain determined for normal tissue ($\epsilon_o$) varies little as the scanning axis is rotated relative to and away from the compression axis as maximum measured by the angle ($\Theta/\pi$). However, line 408 in FIG. 38D shows that the strain determined for an inclusion ($\epsilon$) varies greatly depending on the angle $\Theta$ of rotation of the scanning axis relative to the compression axis. The graph illustrates that the measured strain for the inclusion occurs when the scanning axis coincides with the compression axis but that significant levels of strain for an inclusion are measurable as the scanning axis rotates up to $\Theta/\pi$ 0.25. Accordingly, one can increase the resolution of defining of the inclusion by rotating the scanning axis relative to the compression axis because additional information about the deformation is available from an off-axis orientation. Similarly, rotating the compression axis relative to the scanning axis would have a similar effect.

The effects shown on FIGS. 35–38 are enhanced proportionally with increasing the range of deformations.

FIGS. 39 and 40 describe evaluation of boundaries between portions of tissue differing in elastic modulus and estimating the signs of changes of elasticity of tissue along chosen lines in the image of the compound tissue. FIG. 39, is an illustration of tissue compressed where a scanner can be moved linearly transversely to the direction of compression. In this figure, tissue 410 is supported on a support plate 411 and is loaded with a compressing plate 412, using a known force generator to compress the tissue 410 a desired amount. A scanner 414 is slidably mounted for movement in the direction as indicated by the arrows 415 along a Z axis (as illustrated in the vector diagram adjacent the drawing). Moving the scanner in this way corresponds to movement of the scanner in the third dimension as discussed in conjunction with FIG. 33.

A tumor 416 having Young's modulus of elasticity of $E_1$ is positioned in the tissue, and the vector representation for particles of the tissue is three dimensional, including vector directions v, u and w. By displacing the scanner linearly transversely, three-dimensional information about the tumor and tissue are provided in terms of elasticity modulus by evaluating a series of two-dimensional images of the distortion of particular particles under compression. Even in the case when a tumor cannot be seen directly on the image of tissue, analysis of the distortion of the tissue at various points on a cross-section (i.e., two-dimensional image) of the tissue indicates a boundary between normal tissue and an inclusion.

The block diagram (accompanying the illustration of the apparatus) on FIG. 39 illustrates another method of identifying a region of different elasticity within a tissue portion. This method is based on the method discussed in conjunction with FIG. 33. In this method, similar to that discussed in conjunction with FIG. 29, images of the internal structure of the tissue before and during compression of the tissue are compared. By a speckle tracking technique or similar method, one can define two-dimensional individual tissue particles within the tissue and determine the change in the dimensions of each tissue particle by comparing the before compression and during compression images. The change in dimensions can be expressed as ratio of a horizontal dimension ($b_1$) to a vertical dimension ($a_1$) to yield a strain characteristic value $\epsilon$ equal to ($b_1/a_1$) for each tissue particle. This determination is represented by the box 413 indicating calculating the local displacement of each tissue particle and box 415 representing an experimentally determined profile or strain function of the strain characteristic value for each tissue particle. Thus far, this method is the same as the method as was discussed in connection with FIGS. 33, 34A, 34B and 34C.

For any value of (x), the experimental stress-strain factor $\chi$ can then be determined along a measurement axis at the point (y) by calculating a ratio of the experimental strain characteristic at the point (i.e., tissue particle) (y+$\Delta$y) over the experimental strain characteristic at the point (i.e., tissue particle) (y–$\Delta$y). Thus, using the displacements obtained from tracking of the original y position and the change in the y position under compression, and utilizing the established strain $\epsilon$ profile or function, the stress-strain factor $\chi$ for each adjacent pair of tissue particles along the y measurement axis can be determined as indicated in box 417. The boundary of an inclusion (or tumor 416) can be determined based on the stress-strain factor $\chi$, as indicated in box 418.

To do so, one identifies a profile of adjacent tissue particles that have a stress-strain factor $\chi$ (i.e., a calculated strain characteristic ratio) equal to non-unity. A non-unity stress-strain factor (ratio) indicates adjacent tissue particles experiencing different amounts of strain thereby indicating different moduli of elasticity for the adjacent tissue particles. Accordingly, identifying a profile of adjacent tissue particles with non-unity stress-strain factors indicates the boundary between a region having different elasticity (e.g. inclusion) than the remaining surrounding tissue portion (e.g. normal tissue). Once the profile is determined, a ratio can be calculated for a strain value of a tissue particle, the inclusion region over a strain value of the surrounding normal tissue and this ratio will yield a stress-strain factor $\chi^{*exp}$ that allows one to determine the relative elasticity of the inclusion and surrounding tissue, because of the strong correlation between the strain characteristic value and the modulus of elasticity for a given tissue particle. For example, this relative elasticity can be expressed as a ratio of the modulus of elasticity ($E_1$) for the inclusion to the modulus of elasticity ($E_o$) for the surrounding tissue (See box 419 in FIG. 39).

Figure 40A:
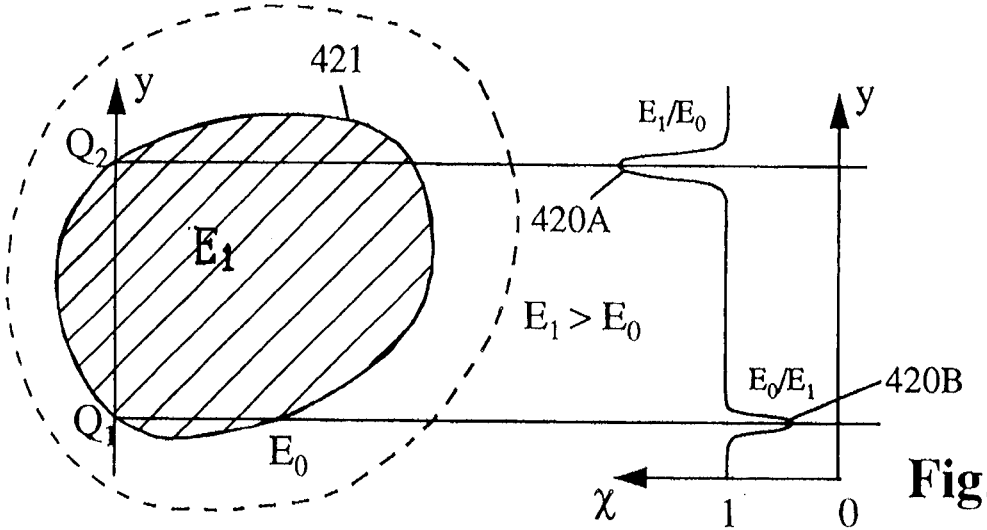
FIG. 40A is a graphical representation of a ratio of modulus of elasticities corresponding to boundaries of an inclusion along a Y axis.
Figure 40B:
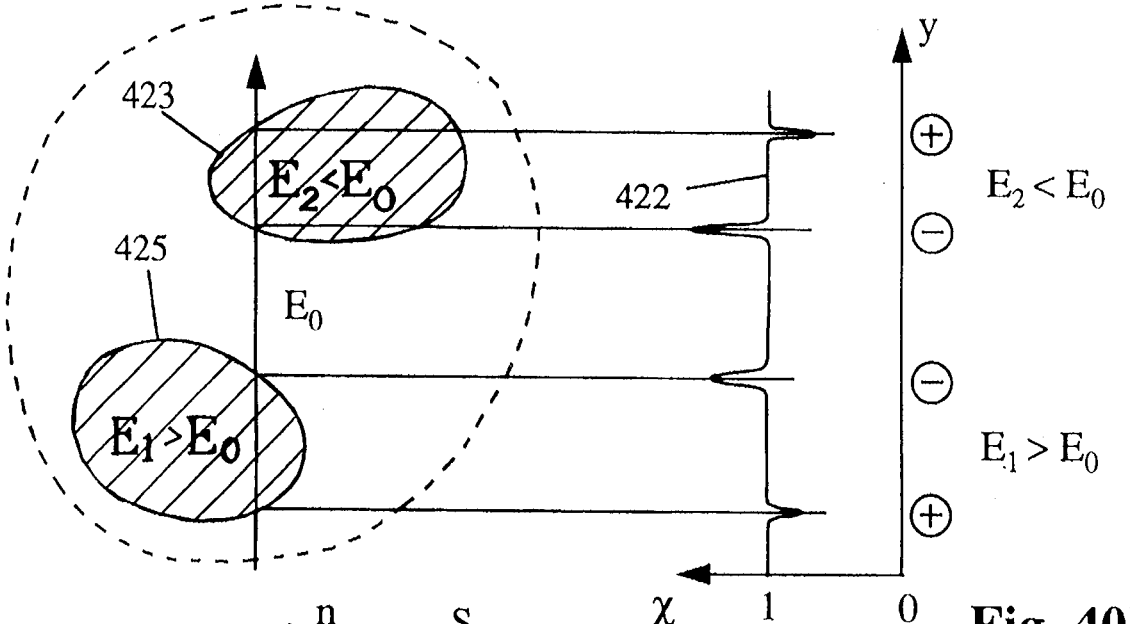
FIG. 40B is a graphical representation of a ratio of modulus of elasticities corresponding to inclusion boundaries along a Y axis for a hard tumor and a soft tumor.
Figure 40C:
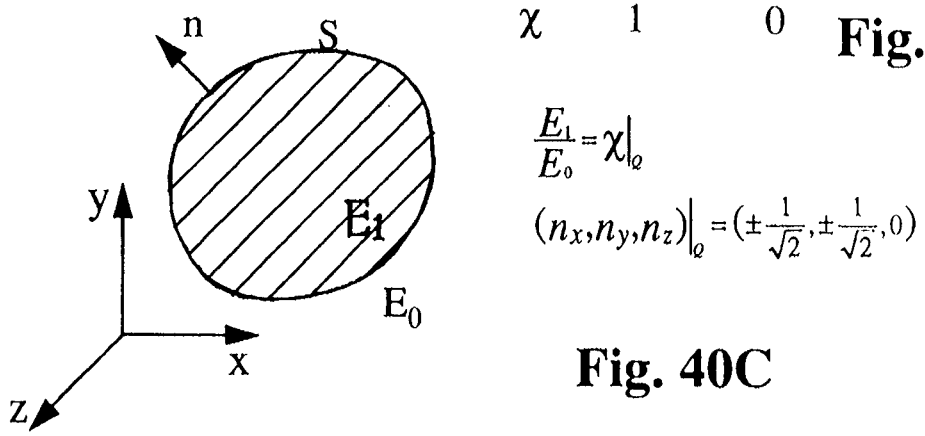
FIG. 40C is a graphical representation depicting a tumor in a three dimensional coordinate system.

In FIGS. 40, 40B and 40C, graphical representations are shown for different conditions of relative elastic moduli and illustrate ways of evaluating boundary transitions. In FIG. 40A, the stress-strain factor $\chi$ is plotted on a horizontal axis, the graph line 420 illustrates transitions in terms of a ratio of modulus of elasticity between surrounding tissue and a tumor 421, where a change in elasticity modulus occurs along the Y axis at points $Q_2$ and $Q_1$. In this case, the elasticity modulus ($E_1$) of the inclusion or tumor 421 is greater than that of the surrounding tissue ($E_o$). Thus, when going from softer to harder tissue the ratios of modulus of elasticity of neighboring points becomes smaller than unity at the interface, that is, the base line 420 in FIG. 40A will have left-ward deflection at 420A and when crossing the interface from harder to softer tissue the ratio becomes greater than unity and the base line 420 will have a right-ward deflection 420B.

This procedure can be carried out using the apparatus of FIGS. 30 and 31. The determination of the pressure pattern simultaneously with the calculation of ratios increases the precision of evaluating the elasticity of structures of interest in the imaging. The stress evaluation can be correlated to the plot of ratios to add in resolving the inverse problem.

FIG. 40B illustrates the case with two inclusions utilizing graph line 422 to reveal transitions between tissues with differing elasticities. The modulus of elasticity $E_2$ of the inclusion or tumor 423 is less than that of surrounding tissue (represented as $E_0$). The second inclusion 425 shown in FIG. 40B is of the same condition as that shown in FIG. 40A, where the modulus of elasticity of the tumor is larger than that of the surrounding tissue. FIG. 40A and 40B represent a graphical analysis determination of the boundaries between surrounding tissue ($E_0$) and an inclusion or tumor ($E_1$). This step corresponds to box 418 in FIG. 39.

FIG. 40C represents the manner of determining of the relative modulus of elasticity of the tumor, as it is schematically shown in Box 419, FIG. 39. The value $\chi_*$ is the value of $\chi$, calculated at the specific point Q of the inclusion's boundary, in which the normal vector n has a component as indicated on FIG. 40C.

Figure 41:
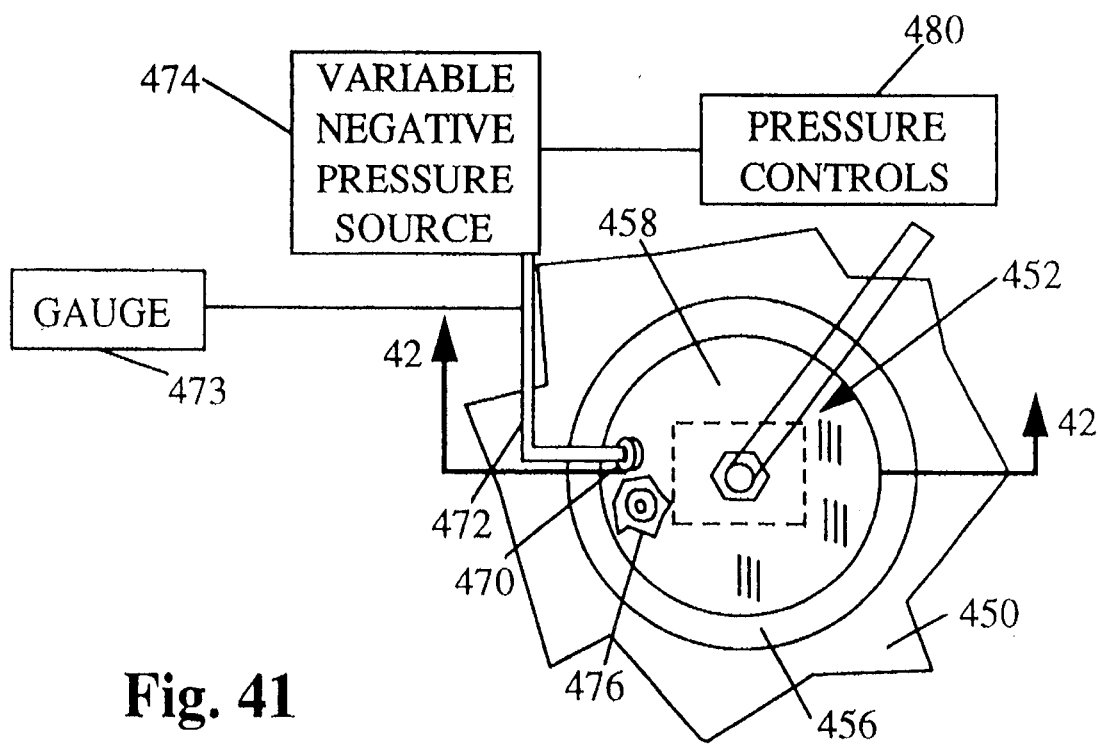
FIG. 41 is a top plan view of a section of human tissue having a deformation device utilizing suction and made according to the present invention in place thereon.
Figure 42:
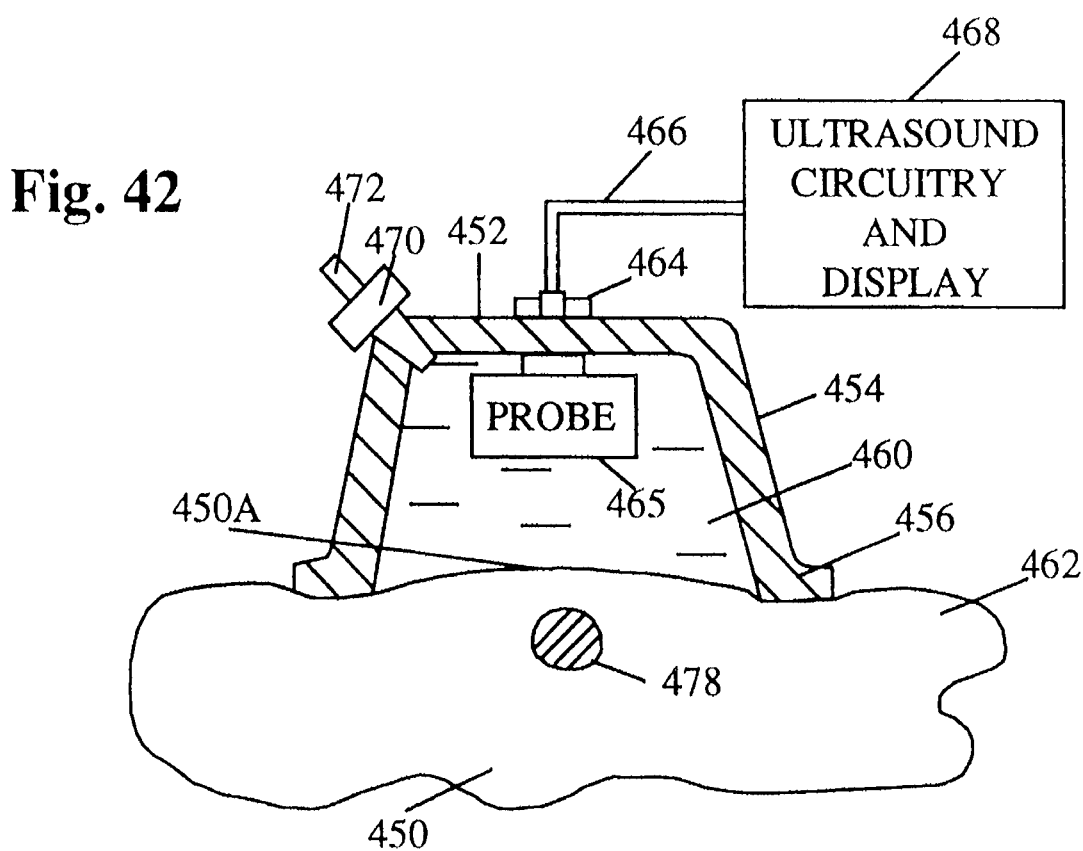
FIG. 42 is a sectional view of the device shown in FIG. 41 as seen on line 42—42.

FIGS. 41 and 42 present one more example of evaluation of elasticity of inclusions by deforming tissue using a different technique of deformation. The technique of deformation presented in FIGS. 41 and 42 provides better possibilities for taking advantage of the above described approaches to evaluation of tissue inclusion hardness in the case where access to the tissue is possible from only one surface.

In FIG. 42, a section of tissue indicated generally at 450 can be tissue covered by skin of a human, such as that of a forearm, leg, or other portion of the anatomy, and is shown only schematically. To analyze the elasticity of the tissue 450, and variations in elasticity as reflected in strain in tissue as outlined previously, the tissue is deformed and imaged while the tissue is deformed.

As seen in FIG. 41 and 42, a suction apparatus indicated generally at 452 comprises a dome-shaped cup member 454 having a flange or peripheral rim 456, and a dome-shaped center portion 458 that forms an interior chamber or cavity 460 when the flange 456 is placed against exterior skin or epidermis 462.

The chamber 460 includes a phased array ultrasonic sensor transducer or probe 465 of conventional design. A suitable connector 464 is used for carrying leads 466 to an ultrasonic imaging circuitry 468 for control and display.

A fitting 470 is used to connect a line 472 leading from a variable negative pressure source 474 (FIG. 42) through the chamber 460, to permit reducing the pressure in the chamber 460. A filling valve 476 (FIG. 42) is openable to permit filling a suitable liquid media into the chamber 460 that provides a coupling between the ultrasonic transducer 465 and the epidermis 462, and thus to the underlying tissue.

As shown, the tissue 450 has a representative tumor 478 therein, relatively close to the epidermis. Tumor 478 has a different elasticity or elasticity modulus than the surrounding tissue 450. By providing a negative pressure from the variable negative pressure source 474 on the interior chamber 460 (and after at least partially filling the chamber with the coupling fluid), the tissue under the cup will bulge up, or in other words, deform into a bulge indicated generally at 450A in FIG. 42. This bulge causes deformation of tissue, and also causes the tumor 478 to move. The tumor 478 is of different elasticity than the surrounding tissue, so the amount of deformation is different, and the difference in elasticity will be represented on the image on the ultrasonic display 468 when the ultrasonic probe 465 is operated in a conventional manner.

The differences in elasticity can be calculated in the manner presented above based on the difference in strain in the tissue as represented in the image generated by the ultrasonic sensing head. Analysis of the condition of the tissue, the size of the tumor, and other characteristics of the tumor can be made.

The negative pressure source can be varied by controls 480, which are used to dynamically vary the negative pressure to cause changes in deformation of the tissue, or to maintain the negative pressure and thus the deformation at steady state. The steady state value of the negative pressure can be changed if desired. The controls can be made to interface with the ultrasonic images and go through a sequence of pressure variation or patterns. The controls can be computer controls or manual controls. A suction gauge 473 also is provided for reference. The probe 465 is preferably a phased array ultrasonic probe using known circuitry. A wide variety of such imaging devices are available.

Tissue deformation under the negative pressure produced by the suction cup can thus be obtained to permit analysis by other imaging modalities such as x-ray or MRI devices.

If desired, suitable sealing agents that aid in sealing the rim 456 to the surface of the skin can be utilized, such as petroleum jelly or other sealants that are presently in use for attaching cups to the skin surface.

Although the present invention has been described with reference to preferred embodiments, workers skilled in the art will recognize that changes may be made in form and detail without departing from the spirit and scope of the invention.

What is claimed is:

1. A method of identifying a region within a tissue portion having a different elasticity than the surrounding tissue of the tissue portion comprising:

causing a deformation of the tissue portion to create stress and strain in the tissue portion;

determining at least one property of at least one of the created stress and strain in the tissue portion when the tissue portion is deformed to yield a pattern of the at least one property of the created stress and strain in the tissue portion; and evaluating the pattern of the at least one property in the tissue portion by the further steps of:

defining a model of the tissue portion with homogeneous tissue and with given boundary conditions for the tissue portion;

calculating the pattern of the at least one property for the defined model;

comparing the pattern obtained in the determining step and the calculated pattern to obtain the difference between the patterns, this difference indicating the presence and location of a differing elasticity region of tissue within the tissue portion; and calculating elasticity characteristics of the tissue portion by varying a spatial distribution of modulus of elasticity in the defined model to minimize the difference between the pattern from the determining step and that calculated for the defined model thereby solving an inverse mechanical problem and obtaining spatial distribution of elasticity modulus in the tissue portion.

2. The method of claim 1 wherein the determining step further comprises:

determining a resistance pressure pattern sensed at locations along a surface of the tissue portion when the tissue portion is deformed to yield the pattern of the stress on the tissue portion.

3. The method of claim 2 wherein the pressure determining step further comprises:

measuring the resistance pressure at a plurality of locations on each of at least two accessible surfaces of the tissue portion to yield a pressure pattern for each accessible surface.

4. The method of claim 1 wherein the determining step further comprises:

determining strain in the tissue portion by comparing images of an internal structure of the tissue portion before and after deformation to yield the pattern of strain in the tissue portion.

5. The method according to claim 1 wherein the determining step includes the step of motion tagging of internal tissue particles to yield the pattern of strain in the tissue portion.

6. The method of claim 5 the determining step further comprising:

imaging the tissue portion and evaluating an image of an internal structure of the tissue portion before and after deformation of the tissue portion to identify boundaries of regions of tissue comprising the tissue portion by determining the ratios of strain characteristic values for regions of the tissue portion having different elasticity.

7. The method of claim 6 wherein changes in modulus of elasticity of the tissue portion along selected reference planes is determined by imaging tissue particles and tagging tissue particles and determining shifting of particles after deformation.

8. The method of claim 5 wherein the step of calculating the pattern forming part of the evaluating step further comprises:

calculating a strain value for each tagged tissue particle along an axis of measurement of the tissue portion;

calculating a ratio of the calculated strain value of a first tissue particle relative to the calculated strain value of a second tissue particle adjacent to the first tissue particle but spaced therefrom along the measurement axis, the ratio being calculated for each pair of adjacent tissue particles along the measurement axis;

identifying a profile of ratios of strain value of adjacent tissue particles having a calculated strain value ratio equal to non-unity, the profile of ratios indicating the boundary between a different elasticity region and the remaining tissue of the tissue portion.

9. The method of claim 8 wherein the axis of measurement is substantially parallel to an axis of force used for causing deformation of the tissue portion.

10. The method of claim 8 wherein the axis of measurement is at a non-parallel angle to an axis of force causing deformation of the tissue portion.

11. The method of claim 8 including the step of determining a pressure resisting deformation at a plurality of locations on a surface of the tissue portion to yield a pattern of stress on the tissue portion.

12. The method of claim 1 wherein the determining step further comprises:

determining changes in both of the properties of stress and strain in the tissue portion when the tissue portion is deformed by measuring pressure at locations on a surface portion to provide the stress pattern, and imaging internal tissue structure after deformation to provide the pattern of stress and the pattern of strain in the tissue portion.

13. The method of claim 1 wherein the deformation causing step further comprises:

causing an additional local deformation in a second surface of the tissue portion opposite the first surface, the second deformation occurring over a substantially smaller area than a region of the first mentioned deformation by probing to additionally compress parts of the tissue portion.

14. The method of claim 1 wherein the deformation causing step further comprises:

causing shear deformation in the tissue portion by laterally shifting one part of the tissue portion relative to another part of the tissue portion on a support structure.

15. The method of claim 14, wherein said support structure is internal skeletal structure.

16. The method of claim 15 wherein the internal skeletal structure is a rib cage and the one part of the tissue portion is adjacent a surface of the tissue overlying the rib cage and is shifted in direction along the rib cage.

17. The method of claim 1 wherein the deformation causing step further comprises:

tilting a support member for the tissue portion while deformation is being caused in the tissue portion.

18. The method of claim 1 wherein the deformation causing step further comprises:

supporting the tissue portion on a surface of a support member while providing a force on a surface of the tissue portion urging the tissue portion toward the support member;

tilting the support member in first and second directions about an axis transverse to the direction of force provided while measuring pressure applied at a plurality of locations on the surface of the tissue portion.

19. The method of claim 1 wherein the tissue portion is a tubular conduit of tissue and the deformation includes expanding the tubular conduit.

20. The method of claim 19 wherein the tubular conduit is of size to receive an expandable probe, and said determining step includes sensing pressure at a plurality of locations on an interior surface of the tubular conduit.

21. The method of claim 19 wherein the tubular conduit is a blood vessel, and the determining step includes providing a tissue imaging device on an interior of the blood vessel.

22. The method of claim 1, wherein the step of causing a deformation of the tissue portion comprises muscle activity affecting and deforming the tissue portion.

23. The method of claim 1 wherein the step of calculating the pattern forming part of the evaluating step further comprises:

calculating deformation induced changes of a ratio for each of a plurality of tissue particles of a horizontal dimension of each tissue particle over a vertical dimension of the same tissue particle to yield a strain characteristic value for each tissue particle;

comparing strain characteristic values of the plurality of tissue particles to identify any region of such tissue particles having strain characteristic values substantially different than the strain characteristic values of tissue particles of a remaining part of the tissue portion, the region corresponding to the location and approximate boundary of a different elasticity region of tissue in the tissue portion.

24. The method of claim 23 and further comprising:

determining the relative elasticity between the different elasticity tissue region and the remaining tissue portion by comparing the different elasticity region strain characteristic value to the remaining tissue portion strain characteristic value.

25. The method of claim 1 wherein said evaluating step includes the step of analyzing under a known condition of deformation changes in the pattern caused by natural mechanical activity of human tissue, to determine structural and dynamic features of human tissue.

26. An apparatus for determining variations in elasticity of bodily tissue comprising:

means for applying pressure to an accessible surface of said tissue to provide at least two conditions of compression loading of tissue to be examined;

means for measuring at least one of the parameters of stress and strain under the at least two different conditions of loading for establishing a pattern of at least one of the parameters in the tissue comprising members that have portions extendable to engage the tissue with a force, and wherein said members comprise a plurality of members in an array across a surface portion of the tissue; and means for evaluating an elasticity of the tissue from changes in the pattern of at least one of the parameters of stress and strain from at least two different conditions of loading.

27. The apparatus of claim 26 wherein the loading comprises compression loading of the tissue to be examined, and the means for measuring at least one parameter comprises means for determining a surface stress pattern on at least part of the accessible surface from the two different conditions of loading, and the means for evaluating the elasticity of the tissue from the surface stress pattern.

28. The apparatus of claim 27 wherein said means for determining the surface stress pattern comprises an array of pressure sensors for obtaining a surface stress pressure pattern of the compressed tissue.

29. The apparatus of claim 26 wherein the parameter measured is strain and the means for evaluating the elasticity of the tissue comprises means for imaging internal tissue structure at the different conditions of loading to evaluate internal strain patterns by detecting changes in boundaries between different internal tissue portions and means for evaluating the spatial distribution of the elasticity modulus from the strain pattern.

30. The apparatus of claim 29 wherein said means for imaging internal structure comprises means for ultrasonic imaging of the internal structure.

31. The apparatus of claim 29 wherein the means for imaging internal structure comprises a magnetic resonance imaging device.

32. The apparatus of claim 29 wherein said means for imaging internal structure comprises means for providing x-ray imaging of internal tissue.

33. The apparatus of claim 26 wherein the parameter measured is strain, and the means for evaluating the elasticity of tissue comprises means to evaluate internal strain patterns by tagging motion of compressed tissue particles and determining changes in locations of tagged tissue particles at the different conditions of loading.

34. The apparatus of claim 33 wherein said means for imaging internal structure comprises means for ultrasonic imaging of the internal structure.

35. The apparatus of claim 33 wherein the means for imaging internal structure comprises a magnetic resonance imaging device.

36. The apparatus of claim 26 wherein said portions of said members are individually actuatable to provide for a preselected pattern of displacement and forces across the surface portion of the tissue to be examined.

37. The apparatus of claim 36 wherein said members comprise fluid pressure actuated cylinders having first and second piston assemblies, said piston assemblies being substantially concentric, and one piston being annular and surrounding the other, and both pistons being individually actuatable to provide variations in pressures on the tissue portion.

38. The apparatus of claim 37 and means for individually actuating the fluid pressure actuated cylinders in a preselected sequence in localized areas across the portion of the tissue being analyzed to create areas of greater load and less load, and means for imaging the internal structure of the tissue during the individual loading sequence.

* * * * *